United States Patent
Nishi et al.

(10) Patent No.: US 11,214,809 B2
(45) Date of Patent: Jan. 4, 2022

(54) VECTOR CONTAINING CENTROMERE DNA SEQUENCE AND USE THEREOF

(71) Applicant: Kaneka Corporation, Osaka (JP)

(72) Inventors: Teruyuki Nishi, Hyogo (JP); Tozo Nishiyama, Hyogo (JP); Toru Watanabe, Hyogo (JP); Yuji Okubo, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 889 days.

(21) Appl. No.: 15/610,917

(22) Filed: Jun. 1, 2017

(65) Prior Publication Data

US 2017/0268013 A1 Sep. 21, 2017

Related U.S. Application Data

(63) Continuation of application No. PCT/JP2015/083977, filed on Dec. 3, 2015.

(30) Foreign Application Priority Data

Dec. 3, 2014 (JP) .............. JP2014-245429

(51) Int. Cl.
*C12N 15/81* (2006.01)
*C12N 15/52* (2006.01)
*C12P 21/02* (2006.01)
*C12P 21/00* (2006.01)
*C12N 15/09* (2006.01)
*C12N 7/00* (2006.01)
*C12N 15/00* (2006.01)

(52) U.S. Cl.
CPC ........... *C12N 15/815* (2013.01); *C12N 15/09* (2013.01); *C12P 21/00* (2013.01); *C12P 21/02* (2013.01); *C12N 7/00* (2013.01); *C12N 15/00* (2013.01)

(58) Field of Classification Search
None
See application file for complete search history.

(56) References Cited

U.S. PATENT DOCUMENTS

| 2014/0244228 A1 | 8/2014 | Lee et al. | |
| 2015/0140626 A1* | 5/2015 | Song | C12P 7/56 435/139 |
| 2017/0218033 A1* | 8/2017 | Zieler | C12N 15/70 |

OTHER PUBLICATIONS

Takahashi et al., Mol. Biol. Cell, 3:819-835 (Year: 1992).*
Sequence Alignment of SEQ ID No. 12 with FN392319. Search conducted on Feb. 23, 2021. 7 pages. (Year: 2021).*
De Shutter et al. Genome sequence of the recombinant protein production host Pichia pastoris. Published online May 24, 2009. Nature Biotechnology. vol. 27, No. 6, pp. 561-566. (Year: 2009).*
Nakamura et al. A Stable, Autonomously Replicating Plasmid Vector Containing Pichia pastoris Centromeric DNA. Posted online May 25, 2018. Applied and Environmental Microbiology. vol. 84, Iss. 15, e02882-17, pp. 1-16. (Year: 2018).*
N. Varoquaux et al. "Accurate identification of centromere locations in yeast genomes using Hi-C", Nucleic Acids Research, May 4, 2015, vol. 43, No. 11, pp. 5331-5339 (9 pages).
J. M. Cregg et al. "Pichia pastoris as a Host System for Transformations", Molecular and Cellular Biology, Dec. 1, 1985, vol. 5, No. 12, pp. 3376-3385 (10 pages).
A. Y. Coughlan et al. "Centromeres of the Yeast Komagataella phaffii (*Pichia pastoris*) Have a Simple Inverted-Repeat Structure", Genome Biology and Evolution, Aug. 1, 2016, vol. 8, No. 8, pp. 2482-2492 (11 pages).
L. Sturmberger et al. "Refined Pichia pastoris reference genome sequence", Journal of Biotechnology, Apr. 12, 2016, vol. 235, pp. 121-131 (11 pages).
I. Liachko et al. "GC-Rich DNA Elements Enable Replication Origin Activity in the Methylotrophic Yeast *Pichia pastoris*", Plos Genetics, Public Library of Science, Mar. 6, 2014, vol. 10, No. 3, pp. e1004169-1, 1-13 (13 pages).
Extended European Search Report issued in European Application No. 15865749.4, dated May 15, 2018 (8 pages).
Polizzi, C. et al., "The Chromatin Structure of Centromeres from Fission Yeast: Differentiation of the Central Core that Correlates with Function", The Journal of Cell Biology, vol. 112, No. 2, Jan. 1991, pp. 191-201 (11 pages).
Clarke, L., "Centromeres of budding and fission yeasts", Trends Genet., May 1990, vol. 6, No. 5, pp. 150-154 (5 pages).
International Search Report issued in PCT/JP2015/083977; dated Jan. 26, 2016 (4 pages).

* cited by examiner

*Primary Examiner* — Channing S Mahatan
(74) *Attorney, Agent, or Firm* — Osha Bergman Watanabe & Burton LLP

(57) ABSTRACT

A vector is provided that includes a nucleotide sequence selected from any one of (a) to (d). The selection of (a) to (d) includes: (a) the nucleotide sequence set forth in SEQ ID NO: 12, 15, 18, or 21, (b) the nucleotide sequence complementary to the nucleotide sequence set forth in SEQ ID NO: 12, 15, 18, or 21, where (a) and (b) hybridize under stringent conditions, (c) the nucleotide sequence having 90% or more sequence identity with the nucleotide sequence set forth in SEQ ID NO: 12, 15, 18, or 21, and (d) the nucleotide sequence set forth in SEQ ID NO: 12, 15, 18, or 21 in which a total of 1 to 50 nucleotides are substituted, deleted, or inserted.

19 Claims, No Drawings
Specification includes a Sequence Listing.

VECTOR CONTAINING CENTROMERE DNA SEQUENCE AND USE THEREOF

TECHNICAL FIELD

One or more embodiments of the present invention relate to a vector comprising a centromere DNA sequence from yeast and use thereof.

BACKGROUND

Recent development of the next-generation sequencers and the like have led to complete sequencing of genomes of many living organisms as well as human, which, in combination with the findings in other omics analyses, has enabled us to get insights into not only the nucleotide sequence but also the genome structure, the gene expression information, the epigenetic change, the protein expression information, the change of intracellular and extracellular metabolites, and the like. In order to artificially engineer these living organisms for the purpose of industrial use, genetic recombination by transformation, for example, genomic integration of a genetic fragment or the like or an autonomous replication vector has been developed for a long time and more recently approaches such as the large-scale genome editing, the genome shuffling, and the artificial chromosome have been pursued. However, the fragment may not be inserted at the intended site and the unexpected influence of greatly changing the genome structure in genome editing such as genomic integration. Moreover, while autonomous replication vectors are widely used in prokaryotes such as *Escherichia coli*, constructing autonomous replication vectors in eukaryotes such as yeast is complicated and most of autonomous replication vectors for eukaryotes are unstable because of containing no centromere DNA sequence.

Centromere DNA sequences of the budding yeast *Saccharomyces cerevisiae* were searched and a 125 bp DNA sequence was identified (Non Patent Literature 1). A long centromere DNA sequence has been also identified in the fission yeast *Schizosaccharomyces pombe* (Non Patent Literature 2). Autonomous replication vectors containing a centromere DNA sequence is not only used in a form of plasmid, but also used on trial in a form of artificial chromosome having a telomere DNA added thereto depending on the host. However, use of a centromere DNA sequence beyond its host is very difficult due to the difference of the proteins that participate in the chromosome segregation. Even in *Komagataella pastoris*, which has been used in industry for a long time, no centromere DNA sequence has been identified, while some autonomously replicating sequences have been reported.

CITATION LIST

Non Patent Literature

Non Patent Literature 1: Trends Genet. 1990; 6: 150-154
Non Patent Literature 2: J Cell Biol. 1991 January; 112(2): 191-201.

SUMMARY

One or more embodiments of the present invention provide a vector having improved stability in host cells. Such a vector is expected to be useful for various uses such as the host improvement for the purpose of industrial use.

The present inventors have identified a DNA sequence that constitutes the centromere of each of the 4 chromosomes in *Komagataella pastoris* by global analysis of the nucleotide sequence of chromosomal DNA of *Komagataella pastoris* and confirmed that vectors containing such a sequence or a part thereof is stably maintained in hosts.

More specifically, one or more embodiments of the present invention encompass the following:

(1)
A vector comprising a nucleotide sequence according to any one of the following (a) to (d):
(a) a nucleotide sequence set forth in SEQ ID NO: 12, 15, 18, or 21;
(b) a nucleotide sequence of a nucleic acid that hybridizes with a nucleic acid consisting of a nucleotide sequence complementary to a nucleotide sequence set forth in SEQ ID NO: 12, 15, 18, or 21, under stringent conditions;
(c) a nucleotide sequence having 85% or more sequence identity with a nucleotide sequence set forth in SEQ ID NO: 12, 15, 18, or 21;
(d) a nucleotide sequence set forth in SEQ ID NO: 12, 15, 18, or 21 in which one or more nucleotides are substituted, deleted, inserted, and/or added.

(2)
The vector according to (1), wherein nucleotide sequences located upstream and downstream of the nucleotide sequence according to any one of (a) to (d) comprise a pair of nucleotide sequences according to any one of the following (e) to (g):
(e) a pair of an upstream nucleotide sequence and a downstream nucleotide sequence that are complementary to each other;
(f) a pair of an upstream nucleotide sequence and a downstream nucleotide sequence that are of nucleic acids that hybridize with each other under stringent conditions;
(g) a pair of an upstream nucleotide sequence and a downstream nucleotide sequence, each of which has 85% or more sequence identity with the complementary nucleotide sequence of the other nucleotide sequence.

(3)
The vector according to (2), wherein the upstream and/or downstream nucleotide sequence according to any one of (e) to (g) has a GC content equal to or higher than 0.8 and equal to or lower than 1.2 when the GC content of the nucleotide sequence according to any one of (a) to (d) is defined as 1.

(4)
The vector according to (2) or (3), wherein the upstream and/or downstream nucleotide sequence in the pair of nucleotide sequences according to any one of (e) to (g) has a GC content equal to or lower than 41%.

(5)
The vector according to any one of (2) to (4), wherein at least one of the upstream and downstream nucleotide sequences in the pair of nucleotide sequences according to any one of (e) to (g) is a nucleotide sequence of yeast chromosomal DNA from the genus *Komagataella*.

(6)
The vector according to any one of (1) to (5), a part comprising at least one nucleotide sequence selected from the nucleotide sequence according to any one of (a) to (d) and the upstream and downstream nucleotide sequences according to any one of (e) to (g) has a binding capacity to a centromere protein (CENP).

(7)
The vector according to any one of (2) to (6), wherein the upstream and downstream nucleotide sequences in the pair of nucleotide sequences according to any one of (e) to (g) are each a nucleotide sequence of 2800 nucleotides or less.

(8)

The vector according to (7), wherein the upstream and downstream nucleotide sequences in the pair of nucleotide sequences according to any one of (e) to (g) are each a nucleotide sequence of 1900-2800 nucleotides.

(9)

The vector according to any one of (2) to (8), wherein the upstream or downstream nucleotide sequence in the pair of nucleotide sequences according to any one of (e) to (g) is a nucleotide sequence according to any one of the following (h) to (k):

(h) a nucleotide sequence set forth in SEQ ID NO: 13, 16, 19, or 22;

(i) a nucleotide sequence of a nucleic acid that hybridizes with a nucleic acid consisting of a nucleotide sequence complementary to a nucleotide sequence set forth in SEQ ID NO: 13, 16, 19, or 22, under stringent conditions;

(j) a nucleotide sequence having 85% or more sequence identity with a nucleotide sequence set forth in SEQ ID NO: 13, 16, 19 or 22;

(k) a nucleotide sequence set forth in SEQ ID NO: 13, 16, 19 or 22 in which one or more nucleotides are substituted, deleted, inserted, and/or added.

(10)

The vector according to any one of (2) to (8), wherein the upstream or downstream nucleotide sequence in the pair of nucleotide sequences according to any one of (e) to (g) is a nucleotide sequence according to any one of the following (l) to (o):

(l) a nucleotide sequence set forth in SEQ ID NO: 14, 17, 20, or 23;

(m) a nucleotide sequence of a nucleic acid that hybridizes with a nucleic acid consisting of a nucleotide sequence complementary to a nucleotide sequence set forth in SEQ ID NO: 14, 17, 20, or 23, under stringent conditions:

(n) a nucleotide sequence having 85% or more sequence identity with a nucleotide sequence set forth in SEQ ID NO: 14, 17, 20, or 23;

(o) a nucleotide sequence set forth in SEQ ID NO: 14, 17, 20, or 23 in which one or more nucleotides are substituted, deleted, inserted, and/or added.

(11)

The vector according to any one of (2) to (8), wherein the upstream and downstream nucleotide sequences in the pair of nucleotide sequences according to any one of (e) to (g) comprise a pair of nucleotide sequences according to any one of the following (p) to (s), (p) a pair of an upstream nucleotide sequence set forth in SEQ ID NO: 13 and a downstream nucleotide sequence set forth in SEQ ID NO: 14;

(q) a pair of an upstream nucleotide sequence set forth in SEQ ID NO: 16 and a downstream nucleotide sequence set forth in SEQ ID NO: 17;

(r) a pair of an upstream nucleotide sequence set forth in SEQ ID NO: 19 and a downstream nucleotide sequence set forth in SEQ ID NO: 20;

(s) a pair of an upstream nucleotide sequence set forth in SEQ ID NO: 22 and a downstream nucleotide sequence set forth in SEQ ID NO: 23.

(12)

The vector according to any one of (1) to (11), wherein the vector comprises a nucleotide sequence according to any one of the following (t) to (w):

(t) a nucleotide sequence set forth in SEQ ID NO: 41, 42, 85, or 86;

(u) a nucleotide sequence of a nucleic acid that hybridizes with a nucleic acid consisting of a nucleotide sequence complementary to a nucleotide sequence set forth in SEQ ID NO: 41, 42, 85, or 86, under stringent conditions;

(v) a nucleotide sequence having 85% or more sequence identity with a nucleotide sequence set forth in SEQ ID NO: 41, 42, 85, or 86;

(w) a nucleotide sequence set forth in SEQ ID NO: 41, 42, 85, or 86 in which one or more nucleotides are substituted, deleted, inserted, and/or added.

(13)

The vector according to any one of (1) to (12), further comprising an autonomous replication sequence (ARS).

(14)

The vector according to (1), comprising at least one of a nucleotide sequence according to any of (h) to (o) described above, more preferably, a nucleotide sequence according to any of (h) and (l) described above in the upstream (5' terminal side) and or the downstream (3' terminal side) of the nucleotide sequence according to any one of (a) to (d) described above.

(15)

The vector according to any one of (1) to (14), wherein the vector is an autonomous replication vector.

(16)

The vector according to (15), wherein the autonomous replication vector further comprises an autonomous replication sequence (ARS) and/or a centromere DNA sequence derived from a biological species different from a biological species from which the nucleotide sequence according to any one of (a) to (d) is derived.

(17)

A vector comprising a nucleotide sequence according to any one of the following (t) to (w):

(t) a nucleotide sequence set forth in SEQ ID NO: 41, 42, 85, or 86;

(u) a nucleotide sequence of a nucleic acid that hybridizes with a nucleic acid consisting of a nucleotide sequence complementary to a nucleotide sequence set forth in SEQ ID NO: 41, 42, 85, or 86, under stringent conditions;

(v) a nucleotide sequence having 85% or more sequence identity with a nucleotide sequence set forth in SEQ ID NO: 41, 42, 85, or 86;

(w) a nucleotide sequence set forth in SEQ ID NO: 41, 42, 85, or 86 in which one or more nucleotides are substituted, deleted, inserted, and/or added.

(18)

A vector comprising a nucleotide sequence according to any one of the following (h) to (k):

(h) a nucleotide sequence set forth in SEQ ID NO: 13, 16, 19, or 22, (i) a nucleotide sequence of a nucleic acid that hybridizes with a nucleic acid consisting of a nucleotide sequence complementary to a nucleotide sequence set forth in SEQ ID NO: 13, 16, 19 or 22, under stringent conditions:

(j) a nucleotide sequence having 85% or more sequence identity with a nucleotide sequence set forth in SEQ ID NO: 13, 16, 19 or 22;

(k) a nucleotide sequence set forth in SEQ ID NO: 13, 16, 19 or 22 in which one or more nucleotides are substituted, deleted, inserted, and/or added.

(19)

A vector comprising a nucleotide sequence according to any one of the following (l) to (o):

(l) a nucleotide sequence set forth in SEQ ID NO: 14, 17, 20, or 23;

(m) a nucleotide sequence of a nucleic acid that hybridizes with a nucleic acid consisting of a nucleotide sequence complementary to a nucleotide sequence set forth in SEQ ID NO: 14, 17, 20, or 23, under stringent conditions;

(n) a nucleotide sequence having 85% or more sequence identity with a nucleotide sequence set forth in SEQ ID NO: 14, 17, 20, or 23;

(o) a nucleotide sequence set forth in SEQ ID NO: 14, 17, 20, or 23 in which one or more nucleotides are substituted, deleted, inserted, and/or added.

(20)

The vector according to any one of (17) to (19), wherein the vector does not comprise any nucleotide sequence according to any of the following (a) to (d):

(a) a nucleotide sequence set forth in SEQ ID NO: 12, 15, 18, or 21;

(b) a nucleotide sequence of a nucleic acid that hybridizes with a nucleic acid consisting of a nucleotide sequence complementary to a nucleotide sequence set forth in SEQ ID NO: 12, 15, 18, or 21, under stringent conditions;

(c) a nucleotide sequence having 85% or more sequence identity with a nucleotide sequence set forth in SEQ ID NO: 12, 15, 18, or 21;

(d) a nucleotide sequence set forth in SEQ ID NO: 12, 15, 18, or 21 in which one or more nucleotides are substituted, deleted, inserted, and/or added.

(21)

The vector according to any one of (17) to (19), wherein the vector is not any vector according to any of (1) to (16).

(22)

A vector comprising a nucleotide sequence set forth in any of SEQ ID NOs: 1-4.

(23)

A method for transforming a cell, comprising the step of introducing a vector according to any one of (1) to (22) into a cell.

(24)

A transformant obtained by transforming a cell with a vector according to any one of (1) to (23).

(25)

The method for transformation according to (23) or the transformant according to (24), wherein the cell is yeast or *Escherichia coli*.

(26)

The method for transformation or transformant according to (25), wherein the cell is a methylotrophic yeast.

(27)

The method for transformation or transformant according to (26), wherein the methylotrophic yeast is a yeast of the genus *Komagataella* or the genus *Ogataea*.

In one or more embodiments of the present invention, hybridization of 2 nucleic acids under stringent conditions means for example, as follows. For example, a nucleic acid Y can be said to be "a nucleic acid that hybridizes with a nucleic acid X under stringent conditions" or a nucleic acid X and a nucleic acid Y can be said to "hybridize with each other under stringent conditions" when the nucleic acid Y can be acquired as a nucleic acid bound onto a filter by hybridizing with the nucleic acid Y with the nucleic acid X immobilized on a filter at 65° C. in the presence of 0.7 to 1.0 M NaCl and then washing the filter at 65° C. with SSC solution of 2 times concentration (the composition of SSC solution of 1 time concentration is 150 mM sodium chloride and 15 mM sodium citrate). In one or more embodiments, the nucleic acid Y is a nucleic acid that can be acquired as a nucleic acid bound onto the filter by washing the filter preferably at 65° C. with SSC solution of 0.5 times concentration, more preferably at 65° C. with SSC solution of 0.2 times concentration, or further preferably at 65° C. with SSC solution of 0.1 times concentration. The nucleic acid X to be used as a standard may be a nucleic acid X derived from a colony or a plaque.

In one or more embodiments of the present invention, the sequence identity of nucleotide sequences can be determined by using a method well known to those skilled in the art, a sequence analysis software, or the like. Examples include the blastn program of BLAST algorithm and the fasta program of FASTA algorithm. In one or more embodiments of the present invention, the "sequence identity" of a nucleotide sequence to be evaluated with a nucleotide sequence Z is a value expressed in % that represents the frequency of appearance of the same nucleotide at the same position in the nucleotide sequence including gaps when the nucleotide sequence Z and the nucleotide sequence to be evaluated are aligned and gaps are introduced as needed so as to maximize the number of matched nucleotide.

In one or more embodiments of the present invention, "one or more" relating to substitution, deletion, insertion, and/or addition of nucleotides refers, for example, in the nucleotide sequence according to (d) described above, to 1-500, 1-400, 1-300, 1-200, 1-190, 1-160, 1-130, 1-100, 1-75, 1-50, 1-25, 1-20, 1-15, 1-10, 1-7, 1-5, 1-4, 1-3, or 1 or 2 in a nucleotide sequence set forth in SEQ ID NO: 12, 15, 18, or 21.

Meanwhile, in the nucleotide sequence according to (k) or the nucleotide sequence according to (o) described above, it refers to, for example, 1-1500, 1-1000, 1-500, 1-400, 1-395, 1-380, 1-350, 1-325, 1-300, 1-295, 1-250, 1-225, 1-200, 1-175, 1-150, 1-125, 1-100, 1-75, 1-50, 1-25, 1-20, 1-15, 1-10, 1-7, 1-5, 1-4, 1-3, or 1 or 2 in a nucleotide sequence set forth in SEQ ID NO: 13, 14, 16, 17, 19, 20, 22, or 23.

Meanwhile, in the nucleotide sequence according to (w) described above, it refers to for example, 1-100, 1-90, 1-80, 1-70, 1-60, 1-50, 1-40, 1-30, 1-25, 1-20, 1-15, 1-10, 1-7, 1-5, 1-4, 1-3, or 1 or 2 in a nucleotide sequence set forth in SEQ ID NO: 41 or 85. Moreover, in the nucleotide sequence according to (w) described above, it refers to, for example, 1-210, 1-200, 1-190, 1-180, 1-170, 1-160, 1-150, 1-140, 1-130, 1-120, 1-110, 1-100, 1-90, 1-80, 1-70, 1-60, 1-50, 1-40, 1-30, 1-25, 1-20, 1-15, 1-10, 1-7, 1-5, 1-4, 1-3, or 1 or 2 in a nucleotide sequence set forth in SEQ ID NO: 42 or 86.

In one or more embodiments of the present invention, "nucleic acid" may be also referred to as the "polynucleotide", refers to DNA or RNA, and typically to DNA.

This description encompasses the contents disclosed in JP Patent Application No. 2014-245429, from which the present application claims priority.

The vector according to one or more embodiments of the present invention can be stably maintained in hosts. Furthermore, the vector according to one or more embodiments of the present invention can be amplified in hosts. Therefore, depending on the purpose of industrial use such as the production of a target compound, a target compound can be efficiently produced by transforming a host cell with a target compound-producing vector comprising the vector according to one or more embodiments of the present invention and further a nucleotide sequence encoding the target compound incorporated into the vector according to one or more embodiments of the present invention.

DESCRIPTION OF EMBODIMENTS

One or more embodiments of the present invention are described in detail with reference to preferred embodiments below.

1. Vector Containing Centromere DNA Sequence

The present inventors have found by a global analysis of the nucleotide sequences of the 4 chromosomal DNAs in *Komagataella pastoris* (The European Molecular Biology Laboratory (EMBL) ACCESSION No. FR839628 to FR839631, J. Biotechnol. 154 (4), 312-320 (2011)) that the nucleotide sequences set forth in SEQ ID NO: 1, 2, 3, and 4 are separately present in the 4 chromosomal DNAs, respectively, in *Komagataella pastoris*.

The present inventors have further found that the nucleotide sequences set forth in SEQ ID NOs: 1, 2, 3, and 4 have the following characteristic structures.

The nucleotide sequence set forth in SEQ ID NO: 1 has a structure in which the nucleotide sequence set forth in SEQ ID NO: 13 is linked to upstream (5' terminal side) of the nucleotide sequence set forth in SEQ ID NO: 12 and the nucleotide sequence set forth in SEQ ID NO: 14 complementary to the nucleotide sequence set forth in SEQ ID NO: 13 is linked to downstream (3' terminal side) of the nucleotide sequence set forth in SEQ ID NO: 12.

The nucleotide sequence set forth in SEQ ID NO: 2 has a structure in which the nucleotide sequence set forth in SEQ ID NO: 16 is linked to upstream (5' terminal side) of the nucleotide sequence set forth in SEQ ID NO: 15 and the nucleotide sequence set forth in SEQ ID NO: 17 complementary to the nucleotide sequence set forth in SEQ ID NO: 16 is linked to downstream (3' terminal side) of the nucleotide sequence set forth in SEQ ID NO: 15.

The nucleotide sequence set forth in SEQ ID NO: 3 has a structure in which the nucleotide sequence set forth in SEQ ID NO: 19 is linked to upstream (5' terminal side) of the nucleotide sequence set forth in SEQ ID NO: 18 and the nucleotide sequence set forth in SEQ ID NO: 20 complementary to the nucleotide sequence set forth in SEQ ID NO: 19 is linked to downstream (3' terminal side) of the nucleotide sequence set forth in SEQ ID NO: 18.

The nucleotide sequence set forth in SEQ ID NO. 4 has a structure in which the nucleotide sequence set forth in SEQ ID NO: 22 is linked to upstream (5' terminal side) of the nucleotide sequence set forth in SEQ ID NO: 21 and the nucleotide sequence set forth in SEQ ID NO: 23 complementary to the nucleotide sequence set forth in SEQ ID NO: 22 is linked to downstream (3' terminal side) of the nucleotide sequence set forth in SEQ ID NO: 21.

The present inventors have completed the vector according to one or more embodiments of the present invention based on the findings described above and the experimental results described in Examples.

1.1. Characteristics of Vector According to One or More Embodiments of the Present Invention In one aspect, the vector according to one or more embodiments of the present invention comprises at least a nucleotide sequence according to any one of the following (a) to (d):

(a) a nucleotide sequence set forth in SEQ ID NO: 12, 15, 18, or 21;

(b) a nucleotide sequence of a nucleic acid that hybridizes with a nucleic acid consisting of a nucleotide sequence complementary to a nucleotide sequence set forth in SEQ ID NO: 12, 15, 18, or 21, under stringent conditions:

(c) a nucleotide sequence having 85% or more, preferably 90% or more, more preferably 95% or more, further preferably 97% or more, or most preferably 99% or more sequence identity with a nucleotide sequence set forth in SEQ ID NO: 12, 15, 18, or 21;

(d) a nucleotide sequence set forth in SEQ ID NO: 12, 15, 18, or 21 in which one or more nucleotides are substituted, deleted, inserted, and/or added.

In one or more embodiments, the vector comprises a nucleotide sequence according to any one of the following (t) to (w):

(t) a nucleotide sequence set forth in SEQ ID NO: 41 or 42 or a nucleotide sequence set forth in SEQ ID NO: 85 or 86, which is a complementary sequence to a nucleotide sequence set forth in SEQ ID NO: 41 or 42, preferably a nucleotide sequence set forth in SEQ ID NO: 41 or 42;

(u) a nucleotide sequence of a nucleic acid that hybridizes with a nucleic acid consisting of a nucleotide sequence complementary to a nucleotide sequence set forth in SEQ ID NO: 41, 42, 85, or 86, or preferably SEQ ID NO: 41 or 42, under stringent conditions:

(v) a nucleotide sequence having 85% or more, preferably 90% or more, more preferably 95% or more, further preferably 97% or more, or most preferably 99% or more sequence identity with a nucleotide sequence set forth in SEQ ID NO: 41, 42, 85, or 86 or preferably SEQ ID NO: 41 or 42;

(w) a nucleotide sequence set forth in SEQ ID NO: 41, 42, 85, or 86 or preferably SEQ ID NO: 41 or 42 in which one or more nucleotides are substituted, deleted, inserted, and/or added.

The vector relating to this aspect may be preferably used as a vector having an autonomous replication capability.

In one or more embodiments, examples of the nucleotide sequence according to (w) include SEQ ID NO: 41 or 85 or (u) or (v) described above (when the nucleotide sequence set forth in SEQ ID NO: 41, 42, 85, or 86 is a nucleotide sequence set forth in SEQ ID NO: 41 or 85), preferably SEQ ID NO: 41 or (u) or (v) described above (when the nucleotide sequence set forth in SEQ ID NO: 41, 42, 85, or 86 is the nucleotide sequence set forth in SEQ ID NO: 41), and particularly preferably the nucleotide subsequence consisting of consecutive in nucleotides starting from the nucleotide at position N in the nucleotide sequence set forth in SEQ ID NO: 41 (wherein m is an integer equal to or higher than 5 nucleotides, or preferably 10 nucleotides and equal to or lower than (11−N+1) nucleotides and N is an integer of 1-107 or preferably 1-102). For example, m may be one of 5, 6, 7, 8, 9, 10, 11, 12, . . . and (111−N+1) and N may be one of 1, 2, 3, 4, . . . and 107. Similarly, examples of the nucleotide sequence according to (w) include SEQ ID NO: 42 or 86 or (u) or (v) described above (when the nucleotide sequence set forth in SEQ ID NO: 41, 42, 85, or 86 is a nucleotide sequence set forth in SEQ ID NO: 42 or 86), preferably SEQ ID NO: 42 or (u) or (v) described above (when the nucleotide sequence set forth in SEQ ID NO: 41, 42, 85, or 86 is the nucleotide sequence set forth in SEQ ID NO: 42), and particularly preferably the nucleotide subsequence consisting of consecutive m' nucleotides starting from the nucleotide at position N' in the nucleotide sequence set forth in SEQ ID NO: 42 (wherein m' is an integer equal to or higher than 5 nucleotides, or preferably 10 nucleotides and equal to or lower than (218−N'+1) nucleotides and N' is an integer of 1-214 or preferably 1-209). For example, m' may be one of 5, 6, 7, 8, 9, 10, 11, 12, . . . and (218−N'+1) and N' may be one of 1, 2, 3, 4, . . . and 214.

In one or more embodiments, the vector comprises a nucleotide sequence according to one of the following (h) to (k):

(h) a nucleotide sequence set forth in SEQ ID NO: 13, 16, 19, or 22;

(i) a nucleotide sequence of a nucleic acid that hybridizes with a nucleic acid consisting of a nucleotide sequence complementary to a nucleotide sequence set forth in SEQ ID NO: 13, 16, 19, or 22, under stringent conditions;

(j) a nucleotide sequence having 85% or more, preferably 90% or more, more preferably 95% or more, further preferably 97% or more, or most preferably 99% or more sequence identity with a nucleotide sequence set forth in SEQ ID NO: 13, 16, 19, or 22;

(k) a nucleotide sequence set forth in SEQ ID NO: 13, 16, 19, or 22 in which one or more nucleotides are substituted, deleted, inserted, and/or added.

The vector relating to this aspect may be preferably used as a vector having an autonomous replication capability.

Furthermore, in another aspect, the vector according to one or more embodiments of the present invention comprises a nucleotide sequence according to one of the following (l) to (o):

(l) a nucleotide sequence set forth in SEQ ID NO: 14, 17, 20, or 23;

(m) a nucleotide sequence of a nucleic acid that hybridizes with a nucleic acid consisting of a nucleotide sequence complementary to a nucleotide sequence set forth in SEQ ID NO: 14, 17, 20, or 23, under stringent conditions;

(n) a nucleotide sequence having 85% or more, preferably 90% or more, more preferably 95% or more, further preferably 97% or more, or most preferably 99% or more sequence identity with a nucleotide sequence set forth in SEQ ID NO: 14, 17, 20, or 23; (o) a nucleotide sequence set forth in SEQ ID NO: 14, 17, 20, or 23 in which one or more nucleotides are substituted, deleted, inserted, and/or added.

The vector relating to this aspect may be preferably used as a vector having an autonomous replication capability.

The vector according to one or more embodiments of the present invention comprises preferably one, more preferably 2 of the following (Characteristic 1) to (Characteristic 2). (Characteristic 1) The vector according to one or more embodiments of the present invention, for example, the vector comprising a nucleotide sequence according to any one of (a) to (d) described above can be stably maintained in hosts. "Stably maintained" means that, when introduced into host cells, it is maintained in host cells even after subculture of the host cells. The vector according to one or more embodiments of the present invention can be stably maintained relative to vectors that do not comprise, for example, a nucleotide sequence according to any one of (a) to (d) described above. Whether a vector is stably maintained or not can be examined, for example, but without limitation, by introducing a reporter gene into the vector and measuring the change of expression strength of the reporter gene during the cell division, as described in Example 4. Alternatively, it can be examined by subculturing a host transformed with the vector containing a marker gene under non-selective conditions and then investigating the frequency of maintenance of the marker gene as described in Example 11 or 12.

According to the purpose of industrial use such as production of a target compound, host cells can be transformed with a target compound-producing vector comprising the vector according to one or more embodiments of the present invention and further comprising a nucleotide sequence encoding the target compound incorporated therein to produce the compound stably and efficiently.

The vector comprising at least a nucleotide sequence according any one of (a) to (d) described above is stably maintained in host cells as confirmed in the experiments of Example 4. It is considered that the nucleic acids consisting of a nucleotide sequence according to any one of (a) to (d) can be used as a centromere DNA that contributes to the stabilization of a chromosome in the cell cycle of host cells. (Characteristic 2) The vector according to one or more embodiments of the present invention is preferably an autonomous replication vector. If the vector according to one or more embodiments of the present invention is an autonomous replication vector, then it can be used for host improvement without changing the genome sequence or the genome structure of the host living organism.

In one or more embodiments of the present invention, the autonomous replication vector refers to a vector that is replicated independently of the chromosomes of the host and that is replicated in the host without being incorporated into a host chromosome.

In one or more embodiments, particularly preferred nucleotide sequences of (d) described above are (d1) nucleotide sequences set forth in SEQ ID NO: 12, 15, 18, or 21 in which 1-200, 1-190, 1-160, 1-130, 1-100, 1-75, 1-50, 1-25, 1-20, 1-15, 1-10, 1-7, 1-5, 1-4, 1-3, or 1 or 2 nucleotides are substituted, deleted, inserted, and/or added;

(d2) a nucleotide sequence set forth in SEQ ID NO: 12, 15, 18, or 21 in which total one or more nucleotides are added to the 5' and/or 3' terminal;

(d3) a nucleotide sequence set forth in SEQ ID NO: 12, 15, 18, or 21 in which total one or more consecutive nucleotides are deleted from the 5' and/or 3' terminal; or (d4) a nucleotide sequence that is a nucleotide subsequence of a nucleotide sequence according to (b) or (c) and that is set forth in SEQ ID NO: 12, 15, 18, or 21 in which one or more nucleotides are substituted, deleted, inserted, and/or added.

1.2. More Preferred Characteristics of Vector According to One or More Embodiments of the Present Invention More preferred embodiments of the vector according to one or more embodiments of the present invention are characterized in that nucleotide sequences located upstream (the 5' terminal side) and downstream (the 3' terminal side) of the nucleotide sequence according to any one of (a) to (d) comprise a pair of nucleotide sequences according to one of the following (e) to (g):

(e) a pair of an upstream nucleotide sequence and a downstream nucleotide sequence that are complementary to each other;

(f) a pair of an upstream nucleotide sequence and a downstream nucleotide sequence that are of nucleic acids that hybridize with each other under stringent conditions;

(g) a pair of an upstream nucleotide sequence and a downstream nucleotide sequence, each of which has 85% or more, preferably 90% or more, more preferably 95% or more, further preferably 97% or more, most preferably 99% or more sequence identity with the complementary nucleotide sequence of the other nucleotide sequence.

For the convenience of illustration, the upstream nucleotide sequence and the downstream nucleotide sequence in the pair of nucleotide sequences according to any one of (e) to (g) described above may be hereinafter referred to as "nucleotide sequence A" and "nucleotide sequence B", respectively.

In one or more embodiments, a particularly preferable pair of the nucleotide sequence A and the nucleotide sequence B is the pair of (e) described above.

A nucleotide sequence set forth in SEQ ID NO: 13, 14, 16, 17, 19, 20, 22, 23, 41, or 42, for example, SEQ ID NO: 16, 17, 19, 20, 41, or 42, particularly SEQ ID NO: 16, 19, 41, or 42, has been confirmed to contain an autonomous replication sequence (ARS) in *Komagataella pastoris*. Accordingly, at least one of the nucleotide sequences according to (h) to (o) described below is used as the nucleotide sequence A and/or the nucleotide sequence B, the vector according to one or more embodiments of the present invention may be used as an autonomous replication vector in a strain of yeast, for example, the genus *Komagataella*, preferably a strain of *Komagataella pastoris*.

The vector according to one or more embodiments of the present invention preferably comprises at least one of Characteristics 1 and 2 described above and Characteristics 3 described below, more preferably comprises at least Characteristics 1 and Characteristics 2, or particularly preferably comprises all of Characteristics 1-3.

(Characteristic 3) The vector according to one or more embodiments of the present invention preferably has a binding capacity to a centromere protein (CENP) and more preferably, a part comprising at least one nucleotide sequence selected from the nucleotide sequence according to any one of (a) to (d) described above and the upstream and downstream nucleotide sequences according to any one of (e) to (g) described above in the nucleic acid molecule constituting the vector according to one or more embodiments of the present invention has a binding capacity to a CENP. CENPs are a group of centromere-specific proteins contained in centromere regions of eukaryotic chromosomes. Since any of a nucleotide sequence according to any of (a) to (d) described above and a nucleotide sequence according to any one of (e) to (g) described above is a nucleotide sequence of a region constituting a centromere in chromosomal DNA of *Komagataella pastoris* or a nucleotide sequence equivalent thereto, the part comprising at least one nucleotide sequence selected from these nucleotide sequences in the vector according to one or more embodiments of the present invention is considered to have a binding capacity to a CENP. Among CENPs, CENP-A is a histone H3 variant specifically located in centromere regions and shared between human, yeast, and the like. Accordingly, the part in the vector according to one or more embodiments of the present invention preferably has a binding capacity to a CENP such as CENP-A in *Komagataella pastoris* and other yeasts and other eukaryotes. Specifically. Examples demonstrate that a part comprising a nucleotide sequence set forth in any one of SEQ ID NOs: 12-23 in the nucleic acid molecule constituting the vector according to one or more embodiments of the present invention has a binding capacity to a CENP.

In the vector according to one or more embodiments of the present invention, the nucleotide sequence A being located upstream of the nucleotide sequence according to any one of (a) to (d) described above refers to the nucleotide at the 3' terminal (referred to as the nucleotide 1) of the nucleotide sequence A being located upstream of the nucleotide at the 5' terminal (referred to as the nucleotide 2) of a nucleotide sequence according to any one of (a) to (d) described above and the nucleotides 1 and 2 may be contiguous or the nucleotides 1 and 2 may be separated with a nucleotide sequence of any number of nucleotides, for example, 1-1000, preferably 1-100, or more preferably 1-10 nucleotides.

In the vector according to one or more embodiments of the present invention, the nucleotide sequence B being located downstream of the nucleotide sequence according to any one of (a) to (d) described above refers to the nucleotide at the 3' terminal (referred to as the nucleotide 3) of the nucleotide sequence B being located upstream of the nucleotide at the 5' terminal (referred to as the nucleotide 4) of a nucleotide sequence according to any one of (a) to (d) described above and the nucleotides 3 and 4 may be contiguous or the nucleotides 3 and 4 may be separated with a nucleotide sequence of any number of nucleotides, for example, 1-1000, preferably 1-100, or more preferably 1-10 nucleotides.

In the vector according to one or more embodiments of the present invention, the lower limit and the upper limit of the GC content of the nucleotide sequence A and/or the nucleotide sequence B are preferably 0.8 and 1.2, respectively, when the GC content of the nucleotide sequence according to any one of (a) to (d) described above is defined as 1. Moreover, the GC content of the nucleotide sequence A and/or the nucleotide sequence B is preferably equal to or less than 41%.

In the vector according to one or more embodiments of the present invention, the numbers of nucleotides of the nucleotide sequence A and the nucleotide sequence B are not particularly limited and they are preferably each equal to or lower than 2800 nucleotides and more preferably each equal to or higher than 1900 nucleotides.

In the vector according to one or more embodiments of the present invention, at least one of the nucleotide sequence A and the nucleotide sequence B is preferably a nucleotide subsequence of chromosomal DNA of yeast of the genus *Komagataella*, for example, chromosomal DNA of *Komagataella pastoris*.

In the vector according to one or more embodiments of the present invention, preferably one of the nucleotide sequence A and the nucleotide sequence B or more preferably the nucleotide sequence A is a nucleotide sequence according to any one of the following (h) to (k):

(h) a nucleotide sequence set forth in SEQ ID NO: 13, 16, 19, or 22;

(i) a nucleotide sequence of a nucleic acid that hybridizes with a nucleic acid consisting of a nucleotide sequence complementary to a nucleotide sequence set forth in SEQ ID NO: 13, 16, 19, or 22, under stringent conditions;

(j) a nucleotide sequence having 85% or more, preferably 90% or more, more preferably 95% or more, further preferably 97% or more, or most preferably 99% or more sequence identity with a nucleotide sequence set forth in SEQ ID NO: 13, 16, 19, or 22;

(k) a nucleotide sequence set forth in SEQ ID NO: 13, 16, 19 or 22 in which one or more nucleotides are substituted, deleted, inserted, and/or added.

In one or more embodiments, the nucleotide sequences according to (h) to (k) are preferably nucleotide sequences that confer an autonomous replication capability to the vector according to one or more embodiments of the present invention. In each of the descriptions of the nucleotide sequences according to (h) to (k), the "nucleotide sequence set forth in SEQ ID NO: 13, 16, 19, or 22" is preferably the "nucleotide sequence set forth in SEQ ID NO: 16 or 19".

In one or more embodiments, particularly preferred nucleotide sequences according to (k) are (k1) a nucleotide sequence set forth in SEQ ID NO: 13, 16, 19, or 22 in which 1-400, 1-375, 1-350, 1-325, 1-295, 1-250, 1-225, 1-200, 1-175, 1-150, 1-125, 1-100, 1-75, 1-50, 1-25, 1-20, 1-15, 1-10, 1-7, 1-5, 1-4, 1-3, or 1 or 2 nucleotides are substituted, deleted, inserted, and/or added;

(k2) a nucleotide sequence set forth in SEQ ID NO: 13, 16, 19, or 22 in which total one or more nucleotides are added to the 5' and/or 3' terminal, in particular 5' terminal;

(k3) a nucleotide sequence set forth in SEQ ID NO: 13, 16, 19, or 22 in which total one or more consecutive nucleotides, for example, total one or more nucleotides are deleted consecutive from the 5' and/or 3' terminal; in particular consecutive from 5' terminal; or (k5) a nucleotide sequence that is a nucleotide subsequence of a nucleotide sequence according to (i) or (j) and that is set forth in SEQ ID NO: 13, 16, 19, or 22 in which one or more nucleotides are substituted, deleted, inserted, and/or added.

Examples of the sequence according to (k3) include (k4) a nucleotide subsequence of consecutive 1-5, 1-10, 1-25, 1-50, 1-75, 1-100, 1-125, 1-150, 1-175, 1-200, 1-225, 1-250, 1-275, 1-300, 1-350, 1-400, 1-450, or 1-500 nucleotides for example, consecutive from the 5' terminal and/or the 3' terminal in SEQ ID NO: 13, 16, 19, or 22. Examples of the sequence according to (k4) include, for example, a nucleotide subsequence of consecutive 1-5, 1-10, 1-25, 1-30, 1-40, 1-50, 1-60, 1-70, 1-80, 1-90, or 1-100 nucleotides in SEQ ID NO: 41 or consecutive 1-5, 1-10, 1-25, 1-30, 1-40, 1-50, 1-60, 1-70, 1-80, 1-90, 1-100 nucleotides, 1-110 nucleotides, 1-120 nucleotides, 1-130 nucleotides, 1-140 nucleotides, 1-150 nucleotides, 1-160 nucleotides, 1-170 nucleotides, 1-180 nucleotides, 1-190 nucleotides, 1-200 nucleotides, or 1-210 nucleotides in SEQ ID NO: 42 and particularly a nucleotide sequence set forth in SEQ ID NO: 41 or 42. In one or more embodiments, preferred examples of the sequence according to (k4) include a nucleotide subsequence of consecutive m nucleotides starting from the Nth nucleotide in the nucleotide sequence set forth in SEQ ID NO: 41 (wherein in is an integer equal to or higher than 5 nucleotides, or preferably 10 nucleotides and equal to or lower than (111−N+1) nucleotides and N is an integer of 1-107 or preferably 1-102). For example, m may be one of 5, 6, 7, 8, 9, 10, 11, 12, . . . and (111−N+1) and N may be one of 1, 2, 3, 4, . . . and 107. Similarly, examples of the nucleotide sequence according to (k4) include a nucleotide subsequence of consecutive m' nucleotides starting from the N'th nucleotide in the nucleotide sequence set forth in SEQ ID NO: 42 (wherein m' is an integer equal to or higher than 5 nucleotides, or preferably 10 nucleotides and equal to or lower than (218−N'+1) nucleotides and N' is an integer of 1-214 or preferably 1-209). For example, m' may be one of 5, 6, 7, 8, 9, 10, 11, 12, . . . and (218−N'+1) and N' may be one of 1, 2, 3, 4, . . . and 214.

Examples of the sequence according to (k5) include (k6) a nucleotide subsequence of consecutive 1-10, 1-25, 1-50, 1-75, 1-100, 1-125, 1-150, 1-175, 1-200, 1-225, 1-250, 1-275, 1-300, 1-350, 1-400, 1-450, or 1-500 nucleotides for example, consecutive from the 5' terminal and/or the 3' terminal in a nucleotide sequence according to (i) or (j) described above.

In one or more embodiments, if "SEQ ID NO: 12, 15, 18, or 21" in the nucleotide sequence according to any one of (a) to (d) is "SEQ ID NO: 12", then "SEQ ID NO: 13, 16, 19, or 22" in the nucleotide sequence according to any one of (h) to (k) is preferably "SEQ ID NO: 13", but not particularly limited.

In one or more embodiments, if "SEQ ID NO: 12, 15, 18, or 21" in the nucleotide sequence according to any one of (a) to (d) is "SEQ ID NO: 15", then "SEQ ID NO: 13, 16, 19, or 22" in the nucleotide sequence according to any one of (h) to (k) is preferably "SEQ ID NO: 16", but not particularly limited.

In one or more embodiments, if "SEQ ID NO: 12, 15, 18, or 21" in the nucleotide sequence according to any one of (a) to (d) is "SEQ ID NO: 18", then "SEQ ID NO: 13, 16, 19, or 22" in the nucleotide sequence according to any one of (h) to (k) is preferably "SEQ ID NO: 19", but not particularly limited.

In one or more embodiments, if "SEQ ID NO: 12, 15, 18, or 21" in the nucleotide sequence according to any one of (a) to (d) is "SEQ ID NO: 21", then "SEQ ID NO: 13, 16, 19, or 22" in the nucleotide sequence according to any one of (h) to (k) is preferably "SEQ ID NO: 22", but not particularly limited.

In the vector according to one or more embodiments of the present invention, preferably one of the nucleotide sequence A and the nucleotide sequence B or more preferably the nucleotide sequence B is a nucleotide sequence according to any one of the following (l) to (o):

(l) a nucleotide sequence set forth in SEQ ID NO: 14, 17, 20, or 23;

(m) a nucleotide sequence of a nucleic acid that hybridizes with a nucleic acid consisting of a nucleotide sequence complementary to a nucleotide sequence set forth in SEQ ID NO: 14, 17, 20, or 23, under stringent conditions;

(n) a nucleotide sequence having 85% or more, preferably 90% or more, more preferably 95% or more, further preferably 97% or more, or most preferably 99% or more sequence identity with a nucleotide sequence set forth in SEQ ID NO: 14, 17, 20, or 23;

(o) a nucleotide sequence set forth in SEQ ID NO: 14, 17, 20, or 23 in which one or more nucleotides are substituted, deleted, inserted, and/or added.

The nucleotide sequences according to (l) to (o) may be nucleotide sequences that confer an autonomous replication capability to the vector according to one or more embodiments of the present invention. In each of the descriptions of the nucleotide sequences according to (l) to (o) described above, the "nucleotide sequence set forth in SEQ ID NO: 14, 17, 20, or 23" is preferably the "nucleotide sequence set forth in SEQ ID NO: 17 or 20".

In one or more embodiments, particularly preferred nucleotide sequences according to (o) are (o1) a nucleotide sequence set forth in SEQ ID NO: 14, 17, 20, or 23 in which 1-400, 1-375, 1-350, 1-325, 1-295, 1-250, 1-225, 1-200, 1-175, 1-150, 1-125, 1-100, 1-75, 1-50, 1-25, 1-20, 1-15, 1-10, 1-7, 1-5, 1-4, 1-3, or 1 or 2 nucleotides are substituted, deleted, inserted, and/or added;

(o2) a nucleotide sequence set forth in SEQ ID NO: 14, 17, 20, or 23 in which total one or more nucleotides are added to the 5' and/or 3' terminal, in particular 3' terminal;

(o3) a nucleotide sequence set forth in SEQ ID NO: 14, 17, 20, or 23 in which total one or more nucleotides are deleted consecutive from the 5' and/or 3' terminal, in particular consecutive from the 3' terminal; or (o5) a nucleotide sequence that is a nucleotide subsequence of a nucleotide sequence according to (m) or (n) and that is set forth in SEQ ID NO: 14, 17, 20, or 23 in which one or more nucleotides are substituted, deleted, inserted, and/or added.

Examples of the sequence according to (o3) include (o4) a nucleotide subsequence of consecutive 1-5, 1-10, 1-25, 1-50, 1-75, 1-100, 1-125, 1-150, 1-175, 1-200, 1-225, 1-250, 1-275, 1-300, 1-350, 1-400, 1-450 or 1-500 nucleotides, for example, consecutive from the 5' terminal and/or the 3' terminal in SEQ ID NO: 14, 17, 20, or 23. Examples of the sequence according to (o4) include, for example, a nucleotide subsequence of consecutive 1-5, 1-10, 1-25, 1-30, 1-40, 1-50, 1-60, 1-70, 1-80, 1-90, or 1-100 nucleotides in SEQ ID NO: 85 or consecutive 1-5, 1-10, 1-25, 1-30, 1-40, 1-50, 1-60, 1-70, 1-80, 1-90, 1-100 nucleotides, 1-110 nucleotides, 1-120 nucleotides, 1-130 nucleotides, 1.140 nucleotides, 1-150 nucleotides, 1-160 nucleotides, 1-170 nucleotides, 1-180 nucleotides, 1-190 nucleotides, 1-200 nucleotides, or 1-210 nucleotides in SEQ ID NO: 86 and particularly a nucleotide sequence set forth in SEQ ID NO: 85 or 86. In one or more embodiments, preferred examples of the sequence according to (o4) include a nucleotide subsequence of consecutive m nucleotides starting from the Nth nucleotide in the nucleotide sequence set forth in SEQ ID NO: 85 (wherein m is an integer equal to or higher than 5 nucleotides, or preferably 10 nucleotides and equal to or lower than (111−N+1) nucleotides and N is an integer of 1-102). For example, m may be one of 5, 6, 7, 8, 9, 10, 11, 12, . . . and (111−N+1) and N may be one of 1, 2, 3, 4, . . . and 107. Similarly, examples of the nucleotide sequence according to (o4) include a nucleotide subsequence of consecutive m' nucleotides starting from the N'th nucleotide in the nucleotide sequence set forth in SEQ ID NO: 86 (wherein m' is an integer equal to or higher than 5 nucleotides, or preferably 10 nucleotides and equal to or lower than (218−N'+1) nucleotides and N' is an integer of 1-209). For example, m' may be one of 5, 6, 7, 8, 9, 10, 11, 12, . . . and (218−N'+1) and N' may be one of 1, 2, 3, 4, . . . and 214.

Examples of the sequence according to (o5) include (o6) a nucleotide subsequence of consecutive 1-5, 1-10, 1-25, 1-50, 1-75, 1-100, 1-125, 1-150, 1-175, 1-200, 1-225, 1-250, 1-275, 1-300, 1-350, 1-400, 1-450, or 1-500 nucleotides, for example, consecutive from the 5' terminal and/or the 3' terminal in a nucleotide sequence according to (m) or (n) described above.

In one or more embodiments, if "SEQ ID NO: 12, 15, 18, or 21" in the nucleotide sequence according to any one of (a) to (d) is "SEQ ID NO: 12", then "SEQ ID NO: 14, 17, 20, or 23" in the nucleotide sequence according to any one of (l) to (o) is preferably "SEQ ID NO: 14", but not particularly limited.

In one or more embodiments, if "SEQ ID NO: 12, 15, 18, or 21" in the nucleotide sequence according to any one of (a) to (d) is "SEQ ID NO: 15", then "SEQ ID NO: 14, 17, 20, or 23" in the nucleotide sequence according to any one of (l) to (o) is preferably "SEQ ID NO: 17", but not particularly limited.

In one or more embodiments, if "SEQ ID NO: 12, 15, 18, or 21" in the nucleotide sequence according to any one of (a) to (d) is "SEQ ID NO: 18", then "SEQ ID NO: 14, 17, 20, or 23" in the nucleotide sequence according to any one of (l) to (o) is preferably "SEQ ID NO: 20", but not particularly limited.

In one or more embodiments, if "SEQ ID NO: 12, 15, 18, or 21" in the nucleotide sequence according to any one of (a) to (d) is "SEQ ID NO: 21", then "SEQ ID NO: 14, 17, 20, or 23" in the nucleotide sequence according to any one of (l) to (o) is preferably "SEQ ID NO: 23", but not particularly limited.

In the vector according to one or more embodiments of the present invention, preferably one of the nucleotide sequence A and the nucleotide sequence B or more preferably the nucleotide sequence A is a nucleotide sequence according to any one of the following (t) to (w):

(t) SEQ ID NO: 41, 42, 85, or 86, preferably a nucleotide sequence set forth in SEQ ID NO: 41 or 42;

(u) a nucleotide sequence of a nucleic acid that hybridizes with a nucleic acid consisting of a nucleotide sequence complementary to a nucleotide sequence set forth in SEQ ID NO: 41, 42, 85, or 86, preferably a nucleotide sequence set forth in SEQ ID NO: 41 or 42, under stringent conditions;

(v) a nucleotide sequence having 85% or more, preferably 90% or more, more preferably 95% or more, further preferably 97% or more, or most preferably 99% or more sequence identity with a nucleotide sequence set forth in SEQ ID NO: 41, 42, 85, or 86 or preferably SEQ ID NO: 41 or 42;

(w) a nucleotide sequence set forth in SEQ ID NO: 41, 42, 85, or 86 or preferably SEQ ID NO: 41 or 42 in which one or more nucleotides are substituted, deleted, inserted, and/or added. The nucleotide sequences according to (t) to (w) may be contained as a whole sequence or subsequence of any of the sequences described above, for example, a nucleotide sequence according to any one of (a) to (d), an upstream and/or downstream nucleotide sequence constituting a pair of nucleotide sequences according to (e) to (g), a nucleotide sequence according to (h) to (o) described above or may be contained separately from these sequences.

In one or more embodiments, the nucleotide sequences according to (t) to (w) are preferably nucleotide sequences that confer an autonomous replication capability to the vector according to one or more embodiments of the present invention.

The nucleotide sequence according to (w) encompasses a nucleotide sequence that is a nucleotide subsequence of (u) or (v) described above and that is a nucleotide sequence set forth in SEQ ID NO: 41, 42, 85, or 86 in which one or more nucleotides are substituted, deleted, inserted, and/or added.

In one or more embodiments, examples of the nucleotide sequence according to (w) include SEQ ID NO: 41 or 85 or (u) or (v) described above (when the nucleotide sequence set forth in SEQ ID NO: 41, 42, 85, or 86 is a nucleotide sequence set forth in SEQ ID NO: 41 or 85), preferably SEQ ID NO: 41 or (u) or (v) described above (when the nucleotide sequence set forth in SEQ ID NO: 41, 42, 85, or 86 is the nucleotide sequence set forth in SEQ ID NO: 41), and particularly preferably the nucleotide subsequence consisting of consecutive m nucleotides starting from the nucleotide at position N in the nucleotide sequence set forth in SEQ ID NO: 41 (wherein m is an integer equal to or higher than 5 nucleotides, or preferably 10 nucleotides and equal to or lower than (111−N+1) nucleotides and N is an integer of 1-107 or preferably 1-102). For example, m may be one of 5, 6, 7, 8, 9, 10, 11, 12, . . . and (111−N+1) and N may be one of 1, 2, 3, 4, . . . and 107. Similarly, examples of the nucleotide sequence according to (w) include SEQ ID NO: 42 or 86 or (u) or (v) described above (when the nucleotide sequence set forth in SEQ ID NO: 41, 42, 85, or 86 is a nucleotide sequence set forth in SEQ ID NO: 42 or 86), preferably SEQ ID NO: 42 or (u) or (v) described above (when the nucleotide sequence set forth in SEQ ID NO: 41, 42, 85, or 86 is the nucleotide sequence set forth in SEQ ID NO: 42), and particularly preferably the nucleotide subsequence consisting of consecutive m' nucleotides starting from the nucleotide at position N' in the nucleotide sequence set forth in SEQ ID NO: 42 (wherein m' is an integer equal to or higher than 5 nucleotides, or preferably 10 nucleotides and equal to or lower than (218−N'+1) nucleotides and N' is an integer of 1-214 or preferably 1-209). For example, m' may be one of 5, 6, 7, 8, 9, 10, 11, 12, . . . and (218−N'+1) and N' may be one of 1, 2, 3, 4, . . . and 214.

In one or more embodiments, the nucleotide sequence B is preferably a nucleotide sequence complementary to the nucleotide sequence set forth in SEQ ID NO: 41 or 42;

a nucleotide sequence of a nucleic acid that hybridizes with a nucleic acid consisting of a nucleotide sequence set forth in SEQ ID NO: 41 or 42, under stringent conditions;

a nucleotide sequence having 85% or more, preferably 90% or more, more preferably 95% or more, further preferably 97% or more, or most preferably 99% or more sequence identity with a nucleotide sequence complementary to a nucleotide sequence set forth in SEQ ID NO: 41 or 42.

In one or more embodiments, particularly preferable combinations of the nucleotide sequence A and the nucleotide sequence B are a pair of nucleotide sequences according to the following (p) to (s):

(p) a pair of an upstream nucleotide sequence set forth in SEQ ID NO: 13 and a downstream nucleotide sequence set forth in SEQ ID NO: 14;

(q) a pair of an upstream nucleotide sequence set forth in SEQ ID NO: 16 and a downstream nucleotide sequence set forth in SEQ ID NO: 17 or a pair of an upstream nucleotide sequence comprising the sequence set forth in SEQ ID NO: 41 and a downstream nucleotide sequence complementary to a nucleotide sequence comprising the sequence set forth in SEQ ID NO: 41;

(r) a pair of an upstream nucleotide sequence set forth in SEQ ID NO: 19 and a downstream nucleotide sequence set forth in SEQ ID NO: 20 or a pair of an upstream nucleotide sequence comprising the sequence set forth in SEQ ID NO: 42 and a downstream nucleotide sequence complementary to a nucleotide sequence comprising the sequence set forth in SEQ ID NO: 42;

(s) a pair of an upstream nucleotide sequence set forth in SEQ ID NO: 22 and a downstream nucleotide sequence set forth in SEQ ID NO: 23.

In one or more embodiments, if "SEQ ID NO: 12, 15, 18, or 21" is "SEQ ID NO: 12" in the nucleotide sequence according to any one of (a) to (d), the nucleotide sequence A and the nucleotide sequence B are preferably the pair according to (p), but not particularly limited.

In one or more embodiments, if "SEQ ID NO: 12, 15, 18, or 21" is "SEQ ID NO: 15" in the nucleotide sequence according to any one of (a) to (d), the nucleotide sequence A and the nucleotide sequence B are preferably the pair according to (q), but not particularly limited.

In one or more embodiments, if "SEQ ID NO: 12, 15, 18, or 21" is "SEQ ID NO: 18" in the nucleotide sequence according to any one of (a) to (d), the nucleotide sequence A and the nucleotide sequence B are preferably the pair according to (r), but not particularly limited.

In one or more embodiments, if "SEQ ID NO: 12, 15, 18, or 21" is "SEQ ID NO: 21" in the nucleotide sequence according to any one of (a) to (d), the nucleotide sequence A and the nucleotide sequence B are preferably the pair according to (s), but not particularly limited.

1.3. Other Preferred Embodiments of Vector According to One or More Embodiments of the Present Invention A more preferred embodiment of the vector according to one or more embodiments of the present invention is a vector comprising at least one of nucleotide sequences according to (h) to (o) described above upstream (5' terminal side) and/or downstream (3' terminal side) of the nucleotide sequence according to any one of (a) to (d) described above.

In Examples, a nucleotide sequence set forth in SEQ ID NO: 13, 14, 16, 17, 19, 20, 22, 23, 41, or 42, for example, SEQ ID NO: 16, 17, 19, 20, 41, or 42, or particularly SEQ ID NO: 16, 19, 41, or 42 is confirmed to comprise an autonomous replication sequence (ARS) in *Komagataella pastoris*. Accordingly, the vector according to one or more embodiments of the present invention comprising at least one of the nucleotide sequences set forth in (h) to (o) that is the same as or equivalent to these nucleotide sequences can be used as an autonomous replication vector.

Since the nucleotide sequence according to any one of (a) to (d) and the nucleotide sequence according to any one of (h) to (o) are a nucleotide sequence of a region constituting a centromere in chromosomal DNA of *Komagataella pastoris* or a nucleotide sequence equivalent thereto, the part comprising at least one nucleotide sequence selected from these nucleotide sequences in the vector according to one or more embodiments of the present invention is considered to have a binding capacity to a CENP.

The vector according to one or more embodiments more preferably comprises at least one of nucleotide sequences according to (h) to (k) described above upstream of the nucleotide sequence according to any one of (a) to (d) described above.

The vector according to one or more embodiments more preferably comprises at least one of nucleotide sequences according to (l) to (o) described above downstream of the nucleotide sequence according to any one of (a) to (d) described above.

In the vector according to one or more embodiments, the nucleotide sequence according to any one of (a) to (d) described above and the nucleotide sequence according to any one of (h) to (o) may be directly linked or may be spaced with a nucleotide sequence of any number of nucleotides, for example, 1-1000, preferably 1-100, or more preferably 1-10.

In one or more embodiments, preferred embodiments of the nucleotide sequence according to any one of (h) to (o) described above are as described in 1.2 above.

1.4. Other Characteristics of Vector According to One or More Embodiments of the Present Invention The vector according to one or more embodiments of the present invention can be introduced into host cells and used to maintain the vector in host cells.

The vector according to one or more embodiments of the present invention may be a vector that can be used for use involving introduction into host cells and expression of a nucleic acid or a target gene in the transformed host cells and it is not necessary that the vector is actually used for such use.

In one or more embodiments of the present invention, the "vector" is a nucleic acid molecule comprising a nucleotide sequence X (a nucleotide sequence according to any one of (a) to (d) described above, an upstream and/or downstream nucleotide sequence constituting a pair of nucleotide sequences according to any one of (e) to (g) described above, a nucleotide sequence according to any one of (h) to (o) and (t) to (w) described above, or a nucleotide sequence in which two or more of these nucleotide sequences are linked (such nucleotide sequences include those linked via another nucleotide sequence of suitable length) described in detail in Sections 1.1, 1.2, and 1.3 above is referred to as the "nucleotide sequence X" for the sake of explanation) described above. The vector according to one or more embodiments of the present invention may also comprise a nucleotide sequence of an exogenous or endogenous gene in addition to the nucleotide sequence X. As used herein, the "exogenous gene" refers to a gene that the host cells do not have inherently and is incorporated in a vector artificially and the "endogenous gene" refers to a gene that the host cells have inherently in chromosomal DNA or cytoplasmic DNA and that is incorporated in the vector artificially for the purpose of conferring the function of the gene on the vector or for the purpose of achieving enhanced expression of the gene. The vector according to one or more embodiments of the present invention may further comprise, in addition to or instead of the nucleotide sequence of an exogenous or endogenous gene, a cloning site containing one or more restriction enzyme recognition sites, a nucleotide sequence of a selection marker gene (an auxotroph complementation gene, a drug-resistant gene, or the like), a nucleotide sequence of a reporter gene and/or an autonomous replication sequence (ARS) such as the replication origin in *Escherichia coli*. The cloning site may be located in a reporter gene and the presence of the function of the reporter gene may be thereby examined to determine the presence of the introduced gene in the cloning site. The vector according to one or more embodiments of the present invention may further comprise a regulatory sequence such as a promoter, a terminator, or the like; an overlap region to be used in the In-Fusion cloning system from Clontech Laboratories, Inc., or the Gibson Assembly system from New England Biolabs Inc. The vector according to one or more embodiments of the present invention may further comprise, depending on the host, a centromere DNA sequence and/or a telomere DNA sequence derived from a biological species different from a biological species from which the nucleotide sequence X is derived.

The exogenous or endogenous gene is a gene introduced for the purpose of producing a substance and typically a nucleic acid encoding a target polypeptide. The exogenous or endogenous gene may be included in the vector in which it is inserted in an expression cassette. The "expression cassette" refers to an expression system comprising an exogenous or endogenous gene and allowing it to be expressed as a polypeptide. The term "allow it to be expressed" refers to a state in which exogenous or endogenous gene contained in the expression cassette is under the control of an element necessary for the expression of the gene such that it can be expressed in the transformant. Examples of the element necessary for the expression of the gene include the following promoters and the following terminators.

Examples of the selection marker gene that can be included in the vector according to one or more embodiments of the present invention include, for example, drug-resistant genes such as ampicillin, Zeocin™, kanamycin, tetracycline, chloramphenicol, and the like. The vector according to one or more embodiments of the present invention may comprise 2 or more selection markers to enable selection with different agents. Examples of the reporter gene that may be contained in the vector according to one or more embodiments of the present invention include LacZ, luciferase, the green fluorescent protein (GFP), and the like. Examples of the promoter that may be contained in the vector according to one or more embodiments of the present invention include the GAP promoter (glyceraldehyde-3-phosphate dehydrogenase promoter) derived from yeast species, the AOX (alcohol oxidase) promoter, the MOX (methanol oxidase) promoter, the FMD (formate dehydrogenase) promoter, and the like. Examples of the terminator that may be contained in the vector according to one or more embodiments of the present invention include the AOX terminator derived from yeast species, the MOX terminator, the terminator of ADH1 (alcohol dehydrogenase 1), the GAL10 terminator, and the like.

In one or more embodiments of the present invention, the autonomous replication sequence (ARS) is a replication origin of a prokaryote (such as *Escherichia coli*, a bacterium, an actinomycete, an eubacterium, an archaeum, a cyanobacterium, or the like), a virus (such as a DNA virus, a RNA virus, or the like), or a eukaryote (such as a fungus, an alga, a protozoan, a yeast, a plant, an animal, a bird, a domestic fowl, a mammal, human, mouse, or the like), or preferably a eukaryote, for example, a yeast such as *Komagataella pastoris* and a region of the nucleotide sequence from which the replication start. The vector according to one or more embodiments of the present invention may comprise, for example, 2 or more autonomous replication sequences from different species. Examples of the autonomous replication sequence that may be contained in the vector according to one or more embodiments of the present invention include the nucleotide sequences according to (t) to (w) described above.

In one or more embodiments of the present invention, the centromere DNA sequence is a nucleotide sequence on which a structure called the centromere is formed and a spindle is bound. For example, it is in human a region where a long arm and a short arm of a chromosome meet and also called a centromere region since it is located almost in the center of the chromosome.

In one or more embodiments of the present invention, the telomere DNA sequence refers to a repetitive structure of a nucleotide sequence that is located usually in the terminal portion of chromosomal DNA and has the function of preventing the damage associated with the replication and maintaining the stability of chromosome during the cell division. Examples of a process for producing a YAC vector containing a telomere DNA include a technique (telomere truncation) involving introducing a cloned telomere DNA sequence by homologous recombination to shorten a chromosome (Itzhaki, Nature Genet. (USA), Vol. 2, p. 283-287, 1992).

Examples of the target polypeptide encoded by the exogenous or endogenous gene include proteins, fusion proteins, antibodies, cytokines, enzymes, and the like.

The vector according to one or more embodiments of the present invention may be a cyclic vector, a linear vector, a plasmid, an artificial chromosome, or the like.

In one or more embodiments of the present invention, the vector is a nucleic acid molecule constructed artificially. A nucleic acid molecule constituting the vector according to one or more embodiments of the present invention is usually DNA, preferably double-stranded DNA and may be cyclic or linear. The vector according to one or more embodiments of the present invention is usually constituted of a nucleic acid fragment comprising the nucleotide sequence X described above or a nucleic acid fragment consisting of the nucleotide sequence X described above linked at the both ends or an end, for example, via a restriction enzyme recognition site to one or more other functional nucleic acid fragment described above.

The scope of the "vector" in one or more embodiments of the present invention encompasses nucleic acid molecules not only in a form that already contains the cloning site, the nucleotide sequence of the selection marker gene, the nucleotide sequence of the reporter gene, the ARS, the regulatory sequence, the overlap region, nucleotide sequence of exogenous gene or the endogenous gene, the centromere DNA sequence, the telomere DNA sequence, or the like, but also in a form into which these sequences can be added (for example, a form that contains a cloning site containing one or more restriction enzyme recognition sites at which these sequence can be added).

The vector according to one or more embodiments of the present invention may be a genomically integrated vector or an autonomous replication vector, but is preferably an autonomous replication vector. The genomically integrated vector according to one or more embodiments of the present invention may be produced by incorporating the nucleotide sequence X described above into a genomically integrated vector.

The vector according to one or more embodiments of the present invention may be produced by incorporating the nucleotide sequence X described above into any vector. The vector into which the nucleotide sequence X is incorporated may be a vector without an autonomous replication sequence in a strain of yeast, for example, the genus *Komagataella*, preferably a strain of *Komagataella pastoris* or a vector having an autonomous replication sequence in yeast. Examples of the vector containing an autonomous replication sequence in yeast include YRp vectors or YCp vectors. A YRp vector refers to a vector having an ARS sequence in yeast and a YCp vector refers to a vector having a centromere sequence and an ARS sequence in yeast. Accordingly, by adding the nucleotide sequence X to a vector without an autonomous replication sequence in yeast, the vector can be changed into a YRp or YCp vector. Moreover, by adding the nucleotide sequence X to a YRp or YCp vector, autonomous replication and stabilization of the vector in other hosts can be promoted.

The vector into which the nucleotide sequence X described above is incorporated is not particularly limited, but examples thereof that can be used include YEp vectors, YRp vectors, YCp vectors, pPICHOLI (world wide web address: mobitec.com/cms/products/bio04_vector_sys/p_picholi_shuttle_vector), pHIP (Journal of General Microbiology (1992), 138, 2405-2416. Chromosomal targeting of replicating plasmids in the yeast *Hansenula polymorpha*), pHRP (see the document cited for pHIP), pHARS (Molecular and General Genetics MGG February 1986, Volume 202, Issue 2, pp 302-308, Transformation of the methylotrophic yeast *Hansenula polymorpha* by autonomous replication and integration vectors), *Escherichia coli*-derived plasmid vectors (such as pUC18, pUC19, pBR322, pBluescript, or pQE), *Bacillus subtilis*-derived plasmid vectors (such as pHY300PLK or pMTLBS72), and the like. The method of incorporating the sequence into these other vectors is not particularly limited but the incorporation is possible by employing a method involving inserting a nucleic acid fragment containing the nucleotide sequence X described above and containing restriction enzyme recognition sites at the both ends into a cloning site containing the corresponding restriction enzyme recognition sites in another vector, the In-Fusion cloning system from Clontech Laboratories, Inc., the Gibson Assembly system from New England Biolabs Inc., or the like.

An autonomous replication sequence (ARS) depending on the host can be incorporated into a vector to make the vector according to one or more embodiments of the present invention as an autonomous replication vector. However, if the nucleotide sequence X described above contains a sequence that functions as an autonomous replication sequence for the host, then any autonomous replication sequence is not necessary to be separately incorporated into the vector. In Examples of one or more embodiments of the present invention, nucleotide sequences set forth in any of SEQ ID NO: 12-23, 41, or 42, preferably SEQ ID NO: 16, 17, 19, 20, 41, or 42, or further preferably SEQ ID NO: 16, 19, 41, or 42 are confirmed to comprise an ARS in *Komagataella pastoris*, and a vector containing a nucleotide sequence set forth in any of SEQ ID NO: 12-23, 41, or 42, for example, SEQ ID NO: 16, 17, 19, 20, 41, or 42, particularly SEQ ID NO: 16, 19, 41, or 42 is at least experimentally confirmed to be available as an autonomous replication vector in yeasts including yeasts of the genus *Komagataella* such as *Komagataella pastoris*.

The vector according to one or more embodiments of the present invention exists preferably as an autonomous replication vector in host cells after transformation but it may be incorporated into a chromosome.

The vector according to one or more embodiments of the present invention may be in a form of artificial chromosome vector. A yeast artificial chromosome vector (YAC vector) generally comprises a centromere DNA sequence, a telomere DNA sequence, and an autonomous replication sequence (ARS).

In Examples, a nucleotide sequence set forth in SEQ ID NO: 12, 15, 18, or 21 or a nucleotide sequence in which one of SEQ ID NOs: 13 and 14 is added at least either upstream or downstream of the nucleotide sequence set forth in SEQ ID NO: 12, a nucleotide sequence in which one of SEQ ID NOs: 16 and 17 is added at least either upstream or downstream of the nucleotide sequence set forth in SEQ ID NO: 15, a nucleotide sequence in which one of SEQ ID NOs: 19 and 20 is added at least either upstream or downstream of the nucleotide sequence set forth in SEQ ID NO: 18, or a nucleotide sequence in which one of SEQ ID NOs: 22 and 23 is added at least either upstream or downstream of the nucleotide sequence set forth in SEQ ID NO: 21 is confirmed to function as a centromere DNA sequence and also as an ARS in yeasts including yeasts of the genus *Komagataella* such as *Komagataella pastoris*. Therefore, in an artificial chromosome vector, a YAC vector can be formed by using a nucleotide sequence according to any one of (a) to (d) or a nucleotide sequence in which at least one nucleotide sequence according to any of (h) to (o) described above is added to upstream and/or downstream of a nucleotide sequence according to any of (a) to (d) described above as a centromere DNA sequence and an ARS, incorporating a telomere DNA sequence into the vector at the both ends, and further incorporating a selection marker as needed.

The vector according to one or more embodiments of the present invention is preferably an autonomous replication vector that can autonomously replicate in host cells of various biological species. Such autonomous replication vectors include vectors comprising a nucleotide sequence according to any of (a) to (d) described above and further comprising an ARS and/or a centromere DNA sequence derived from a biological species different from a biological species from which the nucleotide sequence according to any one of (a) to (d) is derived. Specifically, examples of possible means to make the vector according to one or more embodiments of the present invention not only capable of autonomously replicating in *Komagataella pastoris*, but also capable of autonomously replicating in hosts of other species or other genera include cloning a centromere DNA sequence of human chromosome into a vector containing the nucleotide sequence X to use as a human artificial chromosome, cloning an ARS and a centromere DNA sequence of yeasts of the genus *Ogataea* into a vector containing the nucleotide sequence X to use as an autonomous replication vector for both genus species, cloning an ARS and a centromere DNA sequence of the budding yeast (*Saccharomyces cerevisiae*) and the fission yeast (*Schizosaccharomyces pombe*) to a vector containing the nucleotide sequence X to use as an autonomous replication vector for both genus species, and cloning genes encoding proteins constituting a centromere of *Komagataella pastoris* to a vector containing the nucleotide sequence X to use as an autonomous replication vector for other genus species. Moreover, it is also possible to combine with an autonomous replication vector of *Escherichia coli* as described in Examples.

The vector according to one or more embodiments of the present invention can be stably maintained in host cells as illustrated in Examples but stability can be further improved by adjusting the combination with a selection marker and the vector size. The stability of the vector can be improved, for example, by designing a vector such that removal of the selection marker on the vector results in slow growth or death.

The vector according to one or more embodiments of the present invention can be stably maintained in host cells as illustrated in Examples, but it is also possible to remove the vector. For example, the vector may be removed by subculture in a non-selection medium.

The method for producing the vector according to one or more embodiments of the present invention is not particularly limited, but examples thereof that can be used include total synthesis, PCR, the In-Fusion cloning system from Clontech Laboratories, Inc., the Gibson Assembly system from New England Biolabs Inc., and the like.

2. Transformant

One or more embodiments of the present invention also relate to methods for transforming cells, comprising a step of introducing the vector according to one or more embodiments of the present invention described in Section 1, above into a cell.

One or more embodiments of the present invention relate to a transformant obtained by transforming a cell by the vector according to one or more embodiments of the present invention described in Section 1, above.

The cell which a vector is introduced into and is transformed is referred to as the "host cell", the "host", or the "transformant". As used herein, the host cell before and after transformation may be referred to simply as the "cell".

The cell to be used as the host is not particularly limited as long as it is a cell into which a vector can be introduced.

In one or more embodiments, the host cells to be used in transformation include yeasts, bacteria, fungi, insect cells, or animal cells and yeasts are preferable and methylotrophic yeasts are more preferable.

Methylotrophic yeasts are generally defined as yeasts that can be cultured with methanol as the only carbon source. Methylotrophic yeasts in one or more embodiments of the present invention include yeasts that were originally methylotrophic yeasts, but have lost the methylotrophic ability by an artificial modification or mutation.

Methylotrophic yeasts include yeasts of the genus *Pichia*, the genus *Ogataea, the genus Candida*, the genus *Torulopsis*, and the genus *Komagataella*. In one or more embodiments, preferable examples include *Pichia methanolica* in the genus *Pichia, Ogataea angusta, Ogataea polymorpha, Ogataea parapolymorpha*, and *Ogataea minuta* in the genus *Ogataea, Candida boidinii* in the genus *Candida, Komagataella pastoris* and *Komagataella phaffi* in the genus *Komagataella*.

In one or more embodiments, among the methylotrophic yeasts mentioned above, yeasts of the genus *Komagataella* or the genus *Ogataea* are particularly preferable.

In one or more embodiments, preferable yeasts of the genus *Komagataella* are *Komagataella pastoris* and *Komagataella* phaffi. *Komagataella pastoris* and *Komagataella phaffi* both are also referred to as *Pichia pastoris*.

Specific examples of strains that can be used as a host include strains such as *Komagataella pastoris* ATCC76273 (Y-11430, CBS7435), *Komagataella pastoris* X-33, and the like. These strains can be obtained from American Type Culture Collection, Life technologies Corporation.

In one or more embodiments, preferable yeasts of the genus *Ogataea* are *Ogataea angusta, Ogataea polymorpha*, and *Ogataea parapolymorpha*. These 3 are closely related species and all of them are also referred to as *Hansenula polymorpha* or as *Pichia angusta*.

Specific examples of strains that can be used as a host include strains such as *Ogataea angusta* NCYC495 (ATCC14754), *Ogataea polymorpha* 8V (ATCC34438), and *Ogataea parapolymorpha* DL-1 (ATCC26012). These strains can be obtained from American Type Culture Collection.

In one or more embodiments of the present invention, derivative strains from these yeast strains of the genus *Komagataella* and the genus *Ogataea* may be also used. Examples include *Komagataella pastoris* GS115 strain (which can be obtained from Life technologies Corporation) for histidine auxotroph, and BY4329 derived from NCYC495, BY5242 derived from 8V, and BY5243 derived from DL-1 (which can be obtained from National BioResource Project) for leucine auxotrophic strains. In one or more embodiments of the present invention, derivative strains from these strains and the like can be also used.

In one or more embodiments of the present invention, the "transformant" refers to a transformed cell obtained by introducing the vector described above into a cell. For introducing the vector into a host cell, a known method may be used as appropriate and examples of such methods in which yeast cells are used as a host include, but not particularly limited to electroporation, the lithium acetate method, the spheroplast method, and the like. A typical example of methods for transforming *Komagataella pastoris* is electroporation described in "High efficiency transformation by electroporation of *Pichia pastoris* pretreated with lithium acetate and dithiothreitol" (2004 Biotechniques. January; 36(1):152-4).

In one or more embodiments, when a vector is introduced into host cells for transformation, it is preferred to use a vector containing a selection marker gene, such as an auxotroph complementation gene or a drug-resistance gene. The selection marker is not particularly limited. For example, when a yeast is used as host cells, transformants can be selected based on the recovery of the prototroph phenotype by transforming an uracil, leucine, adenine, histidine, or arginine auxotrophic strain as a host with a vector containing an auxotroph complementation gene such as the URA3 gene, the LEU2 gene, the ADE1 gene, the HIS4 gene, or the ARG4 gene, respectively, as a selection marker gene. When using a vector containing a drug-resistance gene such as the G418-resistance gene, the Zeocin™-resistance gene, or the hygromycin-resistance gene is used as a selection marker gene, transformants can be selected based on the resistance on a medium containing G418, Zeocin™, or hygromycin, respectively. For reference, an auxotroph selection marker for use in generating a yeast host is not available when the selection marker in the host is not destroyed. In this case, the selection marker can be disrupted in the host and a method known by those skilled in the art may be used for the disruption.

The copy number of the vector introduced per cell in the transformant is not particularly limited. The vector may be contained at 1 copy per cell or 2 or more copies per cell (a cell comprising multicopy). A cell comprising single copy may contain the vector in a form of a cyclic vector, a linear vector, or an artificial chromosome or in a form of being incorporated in a chromosome derived from the host. A cell comprising 2 or more copies (multicopy) may contain each vector in a form of a cyclic vector, a linear vector, or an artificial chromosome, or contain each vector in a form of being incorporated in a chromosome derived from the host, or contain vectors in both forms simultaneously.

A cell comprising 2 or more copies (multicopy) may comprise 2 or more copies of the same vector or one or more copies each of different vectors.

The vector to be introduced into the transformant may be transformed in a state of a linear vector and then cyclized in host cells to be kept as a cyclic vector, or transformed in a state of a cyclic vector and then cleaved in host cells to be kept as a linear vector.

Culture conditions for the transformant is not particularly limited and may be selected as appropriate depending on the transformant. In the culture, any medium may be used as long as the medium contains nutrition sources that can be utilized by the transformant. As the nutrition sources, conventional media prepared by suitably mixing a carbon source such as a sugar such as glucose, sucrose, or maltose, an organic acid such as lactic acid, acetic acid, citric acid, or propionic acid, an alcohol such as methanol, ethanol, or glycerol, a hydrocarbon such as paraffin, an oil such as soybean oil or rapeseed oil, or a mixture thereof; a nitrogen source such as ammonium sulfate, ammonium phosphate, urea, yeast extract, meat extract, peptone, or corn steep liquor, and other nutrition sources such as inorganic salts and vitamins can be used.

The vector according to one or more embodiments of the present invention may be used for producing a target product. The "target product" refers to a product that is produced by the transformant into which the vector according to one or more embodiments of the present invention is introduced, for example, a second metabolite such as an antibiotic, a carotenoid, or a vitamin, a protein, a fusion protein, a pharmaceutical preparation, an antibody, a cytokine, or an enzyme.

The target product may be collected by, for example, culturing a transformant obtained by introducing the vector according to one or more embodiments of the present invention into a cell and allowing the target product to be accumulated in the host or in the liquid culture. For collecting the target product, known purification methods can be used in combination as appropriate.

The vector according to one or more embodiments of the present invention may be used for screening for a desired substance. For example, the desired substance may be screened using an enzyme for genome editing such as CRISPR-Cas9 or a mutant DNA polymerase, vectors containing cDNA or siRNA library, a modified gene library for producing the target protein, a promoter library, a terminator library, a noncoding region library, or a tag library.

Furthermore, the vector according to one or more embodiments of the present invention may be also used for the in vitro protein synthesis such as a cell-free system for protein synthesis without using a transformant.

EXAMPLES

Hereinafter, one or more embodiments of the present invention are described in detail by way of Examples, but the present invention is not limited thereby. The detailed procedures of the recombinant DNA techniques used in Examples below are described in the following books: Molecular Cloning 2nd Edition (Cold Spring Harbor Laboratory Press, 1989), Current Protocols in Molecular Biology (Greene Publishing Associates and Wiley-Interscience), Current Protocols in Molecular Biology (Greene Publishing Associates and Wiley-Interscience).

In Examples below, plasmids for use in yeast transformation were prepared by introducing each constructed vector into *Escherichia coli* DH5α competent cells (manufactured by Takara Bio Inc.) or *Escherichia coli* HST08 Premium competent cells (manufactured by Takara Bio Inc.) and culturing an obtained transformant to amplify the vector. Plasmids were prepared from plasmid-harboring strains using the QIAprep spin miniprep kit (manufactured by QIAGEN N.V.).

Centromere DNA sequence 1 (SEQ ID NO: 1). Centromere DNA sequence 2 (SEQ ID NO: 2), Centromere DNA sequence 3 (SEQ ID NO: 3), and Centromere DNA sequence 4 (SEQ ID NO: 4) used in the construction of vectors were prepared by PCR using a mixture of chromosomal DNAs (the nucleotide sequences are set forth in The European Molecular Biology Laboratory (EMBL) ACCESSION No in FR839628-FR839631) of *Komagataella pastoris* ATCC76273 strain as a template, and Primer 3 (SEQ ID NO: 8) for Centromere DNA sequence 1, Primer 4 (SEQ ID NO: 9) for Centromere DNA sequence 2, Primer 5 (SEQ ID NO: 10) for Centromere DNA sequence 3, and Primer 6 (SEQ ID NO: 11) for Centromere DNA sequence 4.

The Zeocin™-resistance gene (SEQ ID NO: 5) under control of a promoter used in the construction of vectors were prepared by PCR using a synthetic DNA as a template. The GFP gene (SEQ ID NO: 32) under control of a promoter used in the construction of vectors were prepared by PCR using a synthetic DNA as a template.

PCR was conducted using Prime STAR HS DNA Polymerase (manufactured by Takara Bio Inc.) under reaction conditions described in the attached manual. The chromosomal DNA was prepared from *Komagataella pastoris* ATCC76273 strain using Dr. GenTLE™ (manufactured by Takara Bio Inc.) or the like under conditions described therein.

Example 1 Construction of Vector Containing Zeocin™-Resistance Gene

A DNA fragment having the HindIII recognition sequence and the NotI recognition sequence added upstream of the Zeocin™-resistance gene (SEQ ID NO: 5) and the EcoRI recognition sequence added downstream of the gene was prepared by PCR using a DNA fragment consisting of SEQ ID NO: 5 as a template and Primers 1 and 2 (SEQ ID NOs: 6 and 7) and inserted between HindIII-EcoRI sites of pUCI9 (manufactured by Takara Bio Inc., Code No. 3219) to prepare pUC-Z.

Example 2: Construction of Vector Containing GFP Gene

A DNA fragment having the HindIII recognition sequence and the NotI recognition sequence added upstream of the GFP gene (SEQ ID NO: 32) and the EcoRI recognition sequence added downstream of the gene was prepared by PCR using a DNA fragment consisting of SEQ ID NO: 32 as a template and Primers 15 and 16 (SEQ ID NOs: 33 and 34) and inserted between HindIII-EcoRI sites of pUC19 to prepare pUC-G.

Example 3: Construction of Autonomous Replication Vector Containing SEQ ID NO: 12, 15, 18, or 21

A DNA fragment having the NotI recognition sequence added upstream and downstream of SEQ ID NO: 12 was prepared by PCR using a DNA fragment consisting of SEQ ID NO: 1 as a template and Primers 7 and 8 (SEQ ID NOs: 24 and 25) and inserted between the NotI sites of pUC-G to prepare pUC-G-KNT1.

A DNA fragment having the NotI recognition sequence added upstream and downstream of SEQ ID NO: 15 was prepared by PCR using a DNA fragment consisting of SEQ ID NO: 2 as a template and Primers 9 and 10 (SEQ ID NOs: 26 and 27) and inserted between the NotI sites of pUC-G to prepare pUC-G-KNT2.

A DNA fragment having the NotI recognition sequence added upstream and downstream of SEQ ID NO: 18 was prepared by PCR using a DNA fragment consisting of SEQ ID NO: 3 as a template and Primers 11 and 12 (SEQ ID NOs: 28 and 29) and inserted between the NotI sites of pUC-G to prepare pUC-G-KNT3.

A DNA fragment having the NotI recognition sequence added upstream and downstream of SEQ ID NO: 21 was prepared by PCR using a DNA fragment consisting of SEQ ID NO: 4 as a template and Primers 13 and 14 (SEQ ID NOs: 30 and 31) and inserted between the NotI sites of pUC-G to prepare pUC-G-KNT4.

Example 4: Acquisition of Yeast Transformant and Measurement of Fluorescence

*Komagataella pastoris* was transformed with the vector pUC-G containing the GFP gene constructed in Example 2 and the vectors pUC-G-KNT1, pUC-G-KNT2, pUC-G-KNT3, and pUC-G-KNT4 containing centromere DNA center sequences constructed in Example 3 as follows.

*Komagataella pastoris* ATCC76273 strain was inoculated to 3 ml of YPD medium (1% yeast extract bacto (manufactured by Difco Laboratories), 2% polypeptone (manufactured by Nihon Pharmaceutical Co., Ltd), 2% glucose) and cultured with shaking at 30° C. overnight, to obtain a liquid preculture. 500 µl of the obtained liquid preculture was inoculated to 50 ml of YPD medium and cultured with shaking at 30° C. until OD600 reached 1-1.5. The cells were then collected (3000×g, 10 minutes, 20° C.) and resuspended into 10 ml of 50 mM potassium phosphate buffer, pH 7.5, containing 250 µl of 1M DTT (final concentration 25 mM).

This suspension was incubated at 30° C. for 15 minutes and then the cells were collected (for 3000×g, 10 minutes, 20° C.) and washed with 50 ml of the STM buffer (270 mM sucrose, 10 mM Tris-HCl, 1 mM magnesium chloride, pH 7.5) that was cooled on ice beforehand. The cells were collected from the washing (for 3000×g, 10 minutes, 4° C.), washed again with 25 ml of the ice-cooled STM buffer, and then collected (for 3.000×g, 10 minutes, 4° C.). Finally, the cells were suspended in 250 µl of the ice-cooled STM buffer to yield a competent cell suspension.

60 µl of this competent cell suspension and 5 µl of a pUC-G solution (1 µg in terms of vector amount) or 5 µl of a pUC-G-KNT1 solution (1 µg as above) or 5 µl of a pUC-G-KNT2 solution (1 µg as above) or a pUC-G-KNT3 solution (1 µg as above) or 5 µl of a pUC-G-KNT4 solution (1 µg as above) were mixed, transferred into an electroporation cuvette (disposable cuvette electrode, 2 mm gap between electrodes, manufactured by BM Equipment Co., Ltd.), and subjected to 7.5 kV/cm, 25 µF, 200Ω. The bacterial cells were then suspended in 1 ml of the YPD medium and left to stand at 30° C. for 2 hours. After 2 hours of standing, the cells were collected (3000×g, 5 minutes, room temperature) and the supernatant was discarded. The remaining cells were resuspended in the YNB medium (0.17% Yeast Nitrogen Base Without Amino Acid (manufactured by Difco Laboratories)) at 30° C. and the transformed cells emitting fluorescence were collected by Fluorescence Activated Cell Sorting (FACS). Observation of the collected cells with a fluorescent microscope during static culture at 30° C. for 2 hours confirmed that while the fluorescence from the transformant with pUC-G decreased, the fluorescence from the transformant with pUC-G-KNT1, pUC-G-KNT2, pUC-G-KNT3, or pUC-G-KNT4 was maintained. This indicates that the nucleic acid consisting of SEQ ID NO: 12, 15, 18, or 21 exhibited a positive effect on the stability of vector in the host.

Example 5: Construction of Autonomous Replication Vector Containing Centromere DNA Sequence A DNA fragment having the NotI recognition sequence added upstream and downstream of SEQ ID NO: 1 was prepared by PCR using a DNA fragment consisting of SEQ ID NO: 1 as a template and Primer 3 (SEQ ID NO: 8) and inserted between the NotI sites of pUC-Z to prepare pUC-Z-CEN1.

A DNA fragment having the NotI recognition sequence added upstream and downstream of SEQ ID NO: 2 was prepared by PCR using a DNA fragment consisting of SEQ ID NO: 2 as a template and Primer 4 (SEQ ID NO: 9) and inserted between the NotI sites of pUC-Z to prepare pUC-Z-CEN2.

A DNA fragment having the NotI recognition sequence added upstream and downstream of SEQ ID NO: 3 was prepared by PCR using a DNA fragment consisting of SEQ ID NO: 3 as a template and Primer 5 (SEQ ID NO: 10) and inserted between the NotI sites of pUC-Z to prepare pUC-Z-CEN3.

A DNA fragment having the NotI recognition sequence added upstream and downstream of SEQ ID NO: 4 was prepared by PCR using a DNA fragment consisting of SEQ ID NO: 4 as a template and Primer 6 (SEQ ID NO: 11) and inserted between the NotI sites of pUC-Z to prepare pUC-Z-CEN4.

SEQ ID NO: 1 is designed to have the nucleotide sequence set forth in SEQ ID NO: 13 in the upstream of the nucleotide sequence set forth in SEQ ID NO: 12 and the nucleotide sequence (SEQ ID NO: 14) complementary to the nucleotide sequence set forth in SEQ ID NO: 13 in the downstream of the nucleotide sequence set forth in SEQ ID NO: 12.

SEQ ID NO: 2 is designed to have the nucleotide sequence set forth in SEQ ID NO: 16 in the upstream of the nucleotide sequence set forth in SEQ ID NO: 15 and the nucleotide sequence (SEQ ID NO: 17) complementary to the nucleotide sequence set forth in SEQ ID NO: 16 in the downstream of the nucleotide sequence set forth in SEQ ID NO: 15.

SEQ ID NO: 3 is designed to have the nucleotide sequence set forth in SEQ ID NO: 19 in the upstream of the nucleotide sequence set forth in SEQ ID NO: 18 and the nucleotide sequence (SEQ ID NO: 20) complementary to the nucleotide sequence set forth in SEQ ID NO: 19 in the downstream of the nucleotide sequence set forth in SEQ ID NO: 18.

SEQ ID NO: 4 is designed to have the nucleotide sequence set forth in SEQ ID NO: 22 in the upstream of the nucleotide sequence set forth in SEQ ID NO: 21 and the nucleotide sequence (SEQ ID NO: 23) complementary to the nucleotide sequence set forth in SEQ ID NO: 22 in the downstream of the nucleotide sequence set forth in SEQ ID NO: 21.

A DNA fragment having the NotI recognition sequence added upstream and downstream of the DNA sequence set forth in SEQ ID NO: 13 was prepared by PCR using a DNA fragment consisting of SEQ ID NO: 1 as a template and Primers 3 and 17 (SEQ ID NOs: 8 and 35) and inserted between the NotI sites of pUC-Z to prepare pUC-Z-Comp1.

A DNA fragment having the NotI recognition sequence added upstream and downstream of the DNA sequence set forth in SEQ ID NO: 16 was prepared by PCR using a DNA fragment consisting of SEQ ID NO: 2 as a template and Primers 4 and 18 (SEQ ID NOs: 9 and 36) and inserted between the NotI sites of pUC-Z to prepare pUC-Z-Comp2.

A DNA fragment having the NotI recognition sequence added upstream and downstream of the DNA sequence set forth in SEQ ID NO: 19 was prepared by PCR using a DNA fragment consisting of SEQ ID NO: 3 as a template and Primers 5 and 19 (SEQ ID NOs: 10 and 37) and inserted between the NotI sites of pUC-Z to prepare pUC-Z-Comp3.

A DNA fragment having the NotI recognition sequence added upstream and downstream of the DNA sequence set forth in SEQ ID NO: 22 was prepared by PCR using a DNA fragment consisting of SEQ ID NO: 4 as a template and Primers 6 and 20 (SEQ ID NOs: 11 and 38) and inserted between the Nod sites of pUC-Z to prepare pUC-Z-Comp4.

A DNA fragment having the NotI recognition sequence added upstream and downstream of the DNA sequence having the nucleotide sequence set forth in SEQ ID NO: 13 upstream of the nucleotide sequence set forth in SEQ ID NO: 12 was prepared by PCR using a DNA fragment consisting of SEQ ID NO: 1 as a template and Primers 3 and 8 (SEQ ID NOs: 8 and 25) and inserted between the NotI sites of pUC-Z to prepare pUC-Z-Comp1KNT1.

A DNA fragment having the NotI recognition sequence added upstream and downstream of the DNA sequence having the nucleotide sequence set forth in SEQ ID NO: 16 upstream of the nucleotide sequence set forth in SEQ ID NO: 15 was prepared by PCR using a DNA fragment consisting of SEQ ID NO: 2 as a template and Primers 4 and 10 (SEQ ID NOs: 9 and 27) and inserted between the NotI sites of pUC-Z to prepare pUC-Z-Comp2KNT2.

A DNA fragment having the NotI recognition sequence added upstream and downstream of the DNA sequence having the nucleotide sequence set forth in SEQ ID NO: 19 upstream of the nucleotide sequence set forth in SEQ ID NO: 18 was prepared by PCR using a DNA fragment consisting of SEQ ID NO: 3 as a template and Primers 5 and 12 (SEQ ID NOs: 10 and 29) and inserted between the NotI sites of pUC-Z to prepare pUC-Z-Comp3KNT3.

A DNA fragment having the NotI recognition sequence added upstream and downstream of the DNA sequence having the nucleotide sequence set forth in SEQ ID NO: 22 upstream of the nucleotide sequence set forth in SEQ ID NO: 21 was prepared by PCR using a DNA fragment consisting of SEQ ID NO: 4 as a template and Primers 6 and 14 (SEQ ID NOs: 11 and 31) and inserted between the NotI sites of pUC-Z to prepare pUC-Z-Comp4KNT4.

Example 6: Acquisition of Yeast Transformant

*Komagataella pastoris* was transformed with the vector pUC-Z containing Zeocin™ resistance gene constructed in Example 1 and the vectors pUC-Z-CEN1, pUC-Z-CEN2, pUC-Z-CEN3, pUC-Z-CEN4, pUC-Z-Comp1, pUC-Z-Comp2, pUC-Z-Comp3, pUC-Z-Comp4, pUC-Z-Comp1KNT1, pUC-Z-Comp2KNT2, pUC-Z-Comp3KNT3, pUC-Z-Comp4KNT4 containing centromere DNA sequences constructed in Example 5 as follows.

*Komagataella pastoris* ATCC76273 strain was inoculated to 3 ml of YPD medium (1% yeast extract bacto (manufactured by Difco Laboratories), 2% polypeptone (manufactured by Nihon Pharmaceutical Co., Ltd), 2% glucose) and cultured with shaking at 30° C. overnight, to obtain a liquid preculture. 500 µl of the obtained liquid preculture was inoculated to 50 ml of YPD medium and cultured with shaking at 30° C. until OD600 reached 1-1.5. The cells were then collected (3000×g, 10 minutes, 20° C.) and resuspended into 10 ml of 50 mM potassium phosphate buffer, pH 7.5, containing 250 µl of 1 M DTT (final concentration 25 mM).

This suspension was incubated at 30° C. for 15 minutes and then the cells were collected (for 3000×g, 10 minutes, 20° C.) and washed with 50 ml of the STM buffer (270 mM sucrose, 10 mM Tris-HCl, 1 mM magnesium chloride, pH 7.5) that was cooled on ice beforehand. The cells were collected from the washing (for 3000×g, 10 minutes, 4° C.), washed again with 25 ml of the ice-cooled STM buffer, and then collected (for 3000×g, 10 minutes, 4° C.). Finally, the cells were suspended in 250 µl of the ice-cooled STM buffer to yield a competent cell suspension.

60 µl of this competent cell suspension and 1 µl of a vector solution (100 ng in terms of vector amount) were mixed, transferred into an electroporation cuvette (disposable cuvette electrode, 2 mm gap between electrodes, manufactured by BM Equipment Co., Ltd.), and subjected to 7.5 kV/cm, 25 µF, 200Ω. The bacterial cells were then suspended in 1 ml of the YPD medium and left to stand at 30° C. for 1 hour. After 1 hour of standing, the cells were collected (3000×g, 5 minutes, room temperature) and 861 µl of the supernatant was discarded. The cells were resuspended with 200 µl of the remaining solution and 100 µl of the suspension was plated onto a YPDZeocin™ selection agar plate (1% yeast extract bacto (manufactured by Difco Laboratories), 2% polypeptone (manufactured by Nihon Pharmaceutical Co., Ltd.), 2% glucose, 1.5% agarose, 0.01% Zeocin™ (manufactured by Life Technologies Corporation). The strains growing in static culture at 30° C. for 3 days were selected and the transformation efficiency (number of colonies per 1 µg of vector, cfu/µg) was calculated (Table 1).

As a result, the transformation efficiencies with pUC-Z-CEN1, pUC-Z-CEN2, pUC-Z-CEN3, pUC-Z-CEN4, pUC-Z-Comp1, pUC-Z-Comp2, pUC-Z-Comp3, pUC-Z-Comp4, pUC-Z-Comp1KNT1, pUC-Z-Comp2KNT2, pUC-Z-Comp3KNT3, and pUC-Z-Comp4KNT4 were clearly higher than the transformation efficiency with pUC-Z. It is considered that transformation did not occur with pUC-Z since it does not have an autonomous replication sequence and the transformation efficiencies with pUC-Z-CEN1, pUC-Z-CEN2, pUC-Z-CEN3, pUC-Z-CEN4, pUC-Z-Comp1, pUC-Z-Comp2, pUC-Z-Comp3, pUC-Z-Comp4, pUC-Z-Comp1KNT1, pUC-Z-Comp2KNT2, pUC-Z-Comp3KNT3, and pUC-Z-Comp4KNT4 were improved since these vectors have an autonomous replication sequence and capable of existing as an autonomous replication plasmid in the transformation yeast cells.

TABLE 1

| Vector | Transformation efficiency (cfu/μg) |
|---|---|
| pUC-Z | 0 |
| pUC-Z-CEN1 | 1800 |
| pUC-Z-CEN2 | 1700 |
| pUC-Z-CEN3 | 1800 |
| pUC-Z-CEN4 | 1900 |
| pUC-Z-Comp1 | 1000 |
| pUC-Z-Comp2 | 1200 |
| pUC-Z-Comp3 | 1100 |
| pUC-Z-Comp4 | 1200 |
| pUC-Z-Comp1KNT1 | 1200 |
| pUC-Z-Comp2KNT2 | 1300 |
| pUC-Z-Comp3KNT3 | 1000 |
| pUC-Z-Comp4KNT4 | 1200 |

Example 7: Confirmation of Plasmid Maintenance

Plasmid solutions were prepared from bacterial cells from 10 colonies each of 12 different yeast transformants obtained in Example 6 using the Easy Yeast Plasmid Isolation Kit (manufactured by Clontech Laboratories). Subsequently, the obtained plasmid solutions were introduced into *E. coli* HST08 Premium competent cells (manufactured by Takara Bio Inc.) and as a result all samples from the yeasts transformed with pUC-Z-CEN1, pUC-Z-CEN2, pUC-Z-CEN3, pUC-Z-CEN4, pUC-Z-Comp1, pUC-Z-Comp2, pUC-Z-Comp3, pUC-Z-Comp4, pUC-Z-Comp1KNT1, pUC-Z-Comp2KNT2, pUC-Z-Comp3KNT3, and pUC-Z-Comp4KNT4 yielded *E. coli* colonies on LBAmp selection agar plates (1% Trypton (manufactured by Nacalai Tesque, Inc.), 1% sodium chloride, 0.5% yeast extract bacto (manufactured by Difco Laboratories), 0.01% ampicillin sodium (manufactured by Wako Pure Chemical Industries, Ltd.)). Moreover, preparation of plasmids from the *E. coli* colonies and sequence analysis of the plasmids confirmed that the prepared plasmids were pUC-Z-CEN1, pUC-Z-CEN2, pUC-Z-CEN3, pUC-Z-CEN4, pUC-Z-Comp1, pUC-Z-Comp2, pUC-Z-Comp3, pUC-Z-Comp4, pUC-Z-Comp1KNT1, pUC-Z-Comp2KNT2, pUC-Z-Comp3KNT3, and pUC-Z-Comp4KNT4 introduced into the yeasts and that there is no sequences derived from another host. This suggests that pUC-Z-CEN1, pUC-Z-CEN2, pUC-Z-CEN3, pUC-Z-CEN4, pUC-Z-Comp1, pUC-Z-Comp2, pUC-Z-Comp3, pUC-Z-Comp4, pUC-Z-Comp1KNT1, pUC-Z-Comp2KNT2, pUC-Z-Comp3KNT3, and pUC-Z-Comp4KNT4 exist in the transformed yeast cells as an autonomous replication plasmid because they have an autonomous replication sequence.

Example 8: Construction of Vector Containing Zeocin™ Resistance Gene and Regulatory Sequence A DNA fragment having the HindIII recognition sequence, the NotI recognition sequence, the BamHI recognition sequence, the SpeI recognition sequence, the MunI recognition sequence, the BglII recognition sequence, and the XbaI recognition sequence, from upstream to downstream, added upstream of the Tmox sequence (SEQ ID NO: 82), which is an MOX terminator in the *Hansenula* yeast, and the XbaI recognition sequence and the EcoRI recognition sequence, from upstream to downstream, added downstream of the Tmox sequence was amplified by PCR using chromosomal DNA of *Ogataea polymorpha* 8V (ATCC34438) strain as a template and Primers 23 and 24 (SEQ ID NOs: 74 and 75) and inserted between the HindIII-EcoRI sites of pUCI9 (manufactured by Takara Bio Inc., Code No. 3219) to prepare pUC_Tmox.

A DNA fragment having the EcoRI recognition sequence added upstream and downstream of HpPgap (SEQ ID NO: 83) was amplified by PCR using chromosomal DNA of *Ogataea polymorpha* 8V (ATCC34438) strain as a template and Primers 27 and 28 (SEQ ID NOs: 78 and 79) and inserted between the MunI sites of pUC_Tmox to prepare pUC_HpPgap_Tmox. Since the EcoRI digested end and the MunI digested end can be ligated, the DNA fragment having the EcoRI recognition sequence added can be inserted between the MunI sites of pUC_Tmox. The ligated sites cannot be digested with EcoRI.

A DNA fragment having the BamHI recognition sequence added upstream and downstream of HpPgap (SEQ ID NO: 83), which is a GAP promoter in the *Hansenula* yeast, was amplified by PCR using chromosomal DNA of *Ogataea polymorpha* 8V (ATCC34438) strain as a template and Primers 25 and 26 (SEQ ID NOs: 76 and 77) and inserted between the BamHI sites of pUC_HpPgap_Tmox to prepare pUC_HpPgap_HpPgap_Tmox.

A DNA fragment having the EcoRI recognition sequence added upstream and downstream of the Zeocin™ resistance gene (nucleotide sequence from the position 681 to the position 1535 in SEQ ID NO: 5) was prepared by PCR using the DNA fragment consisting of the nucleotide sequence of the position 681 to the position 1535 in SEQ ID NO: 5 as a template and Primers 29 and 30 (SEQ ID NOs: 80 and 81) and inserted between the EcoRI sites of pUC_HpPgap_HpPgap_Tmox to prepare pUC_HpPgap_HpPgap_Tmox_Zeo (hereinafter, this vector is also simply referred to as the "pUC-Z2"). pUC-Z2 is a vector containing the nucleotide sequence consisting of SEQ ID NO: 84 between the HindIII and EcoRI sites of pUC19.

Example 9: Identification of Autonomous Replication Sequence

In this Example, the autonomous replication sequences in Comp2 and Comp3 were identified.

First. DNA fragments containing restriction enzyme recognition sequences upstream and downstream of nucleotide sequences truncated by about 300 bp increments on the basis of 1-2400 bp of Comp2 (SEQ ID NO: 16, 2699 base pairs in full length) were prepared by PCR using the DNA fragment consisting of SEQ ID NO: 2 as a template and primers and inserted in restriction enzyme sites of pUC-Z2 to prepare vectors. The sequences inserted into the vectors, the sequences of the primers used for the amplification of the fragments, and the restriction enzymes used for the insertion of the amplified sequences into the vectors are shown in Table 2 below.

Moreover, DNA fragments containing restriction enzyme recognition sequences upstream and downstream of nucleotide sequences truncated by about 300 bp increments on the basis of 1-2400 bp of Comp3 (SEQ ID NO: 19, 2649 base pairs in full length) were prepared as well by PCR using the DNA fragment consisting of SEQ ID NO: 3 as a template and primers and inserted in restriction enzyme sites of pUC-Z2 to prepare vectors. The sequences inserted into the vectors, the sequences of the primers used for the amplification of the fragments, and the restriction enzymes used for the insertion of the amplified sequences into the vectors are shown in Table 2 below.

TABLE 2

| Sequence inserted into pUC-Z2 vector | Forward (Fw) primer | Restriction enzyme site at Fw side | Reverse (Rev) primer | Restriction enzyme site at Rev side |
|---|---|---|---|---|
| Comp2_1-2409 | SEQ ID NO: 43 | NotI | SEQ ID NO: 44 | XbaI |
| Comp2_1-2103 | SEQ ID NO: 43 | NotI | SEQ ID NO: 45 | XbaI |
| Comp2_1-1800 | SEQ ID NO: 43 | NotI | SEQ ID NO: 46 | XbaI |
| Comp2_1-1500 | SEQ ID NO: 43 | NotI | SEQ ID NO: 47 | XbaI |
| Comp2_1-1200 | SEQ ID NO: 43 | NotI | SEQ ID NO: 48 | XbaI |
| Comp2_1-900 | SEQ ID NO: 43 | NotI | SEQ ID NO: 49 | XbaI |
| Comp2_1-600 | SEQ ID NO: 43 | NotI | SEQ ID NO: 50 | XbaI |
| Comp2_1-291 | SEQ ID NO: 43 | NotI | SEQ ID NO: 51 | XbaI |
| Comp3_1-2400 | SEQ ID NO: 52 | NotI | SEQ ID NO: 53 | SpeI |
| Comp3_1-2100 | SEQ ID NO: 52 | NotI | SEQ ID NO: 54 | SpeI |
| Comp3_1-1800 | SEQ ID NO: 52 | NotI | SEQ ID NO: 55 | SpeI |
| Comp3_1-1500 | SEQ ID NO: 52 | NotI | SEQ ID NO: 56 | SpeI |
| Comp3_1-1200 | SEQ ID NO: 52 | NotI | SEQ ID NO: 57 | SpeI |
| Comp3_1-904 | SEQ ID NO: 52 | NotI | SEQ ID NO: 58 | SpeI |
| Comp3_1-600 | SEQ ID NO: 52 | NotI | SEQ ID NO: 59 | SpeI |
| Comp3_1-300 | SEQ ID NO: 52 | NotI | SEQ ID NO: 60 | SpeI |

According to the method described in Example 6, *Komagataella pastoris* was transformed with these vectors and the transformation efficiencies (cfu/µg) were calculated. Inserts that yielded a transformation efficiency of 100 or more were expressed as + and those that yielded a transformation efficiency of less than 100 were expressed as —(Table 3).

As a result, the all vectors containing any of the sequences from Comp2 yielded high transformation efficiencies, suggesting that its autonomous replication sequence locates in the nucleotide sequence from the position 1 to the position 291 of SEQ ID NO: 16.

The vectors containing any sequence from Comp3 except the sequence from the position 1 to the position 300 yielded high transformation efficiencies, suggesting that its autonomous replication sequence locates in the nucleotide sequence from the position 300 to the position 600 of SEQ ID NO: 19.

TABLE 3

| Sequence inserted into pUC-Z2 vector | Transformation efficiency |
|---|---|
| Comp2_1-2409 | + |
| Comp2_1-2103 | + |
| Comp2_1-1800 | + |
| Comp2_1-1500 | + |
| Comp2_1-1200 | + |
| Comp2_1-900 | + |
| Comp2_1-600 | + |
| Comp2_1-291 | + |
| Comp3_1-2400 | + |
| Comp3_1-2100 | + |
| Comp3_1-1800 | + |
| Comp3_1-1500 | + |
| Comp3_1-1200 | + |
| Comp3_1-904 | + |
| Comp3_1-600 | + |
| Comp3_1-300 | − |

Subsequently, DNA fragments containing restriction enzyme recognition sequences upstream and downstream of the nucleotide sequences of the position 1-111 (Comp2_1-111), the position 84-213 (Comp2_84-213), the position 191-291 (Comp2_191-291), and the position 84-2699 (Comp2_84-2699) of Comp2 (SEQ ID NO: 16) were amplified by PCR using the DNA fragment consisting of SEQ ID NO: 2 as a template and primers and inserted in restriction enzyme recognition sites of pUC-Z2 to prepare vectors. The sequences inserted into the vectors, the sequences of the primers used for the amplification of the fragments, and the restriction enzymes used for the insertion of the amplified sequences into the vectors are shown in Table 4 below.

Moreover, DNA fragments containing restriction enzyme recognition sequences upstream and downstream of the nucleotide sequences of the position 268-404 (Comp3_268-404), the position 383-503 (Comp3_383-503), the position 480-600 (Comp3_500-600), the position 268-503 (Comp3_268-503), the position 383-600 (Comp3_383-600), and the position 480-2649 (Comp3_480-2649) of Comp3 (SEQ ID NO: 19) were amplified by PCR using the DNA fragment consisting of SEQ ID NO: 3 as a template and primers and inserted in restriction enzyme sites of pUC-Z2 to prepare vectors. The sequences inserted into the vectors, the sequences of the primers used for the amplification of the fragments, and the restriction enzymes used for the insertion of the amplified sequences into the vectors are shown in Table 4 below.

TABLE 4

| Sequence inserted into pUC-Z2 vector | Forward (Fw) primer | Restriction enzyme site at Fw side | Reverse (Rev) primer | Restriction enzyme site at Rev side |
|---|---|---|---|---|
| Comp2_1-111 | SEQ ID NO: 43 | NotI | SEQ ID NO: 63 | XbaI |
| Comp2_84-213 | SEQ ID NO: 61 | NotI | SEQ ID NO: 64 | XbaI |
| Comp2_191-291 | SEQ ID NO: 62 | NotI | SEQ ID NO: 65 | XbaI |
| Comp2_84-2699 | SEQ ID NO: 61 | NotI | SEQ ID NO: 66 | NotI |
| Comp3_268-404 | SEQ ID NO: 67 | NotI | SEQ ID NO: 70 | SpeI |
| Comp3_383-503 | SEQ ID NO: 68 | NotI | SEQ ID NO: 71 | SpeI |
| Comp3_480-600 | SEQ ID NO: 69 | NotI | SEQ ID NO: 72 | SpeI |

TABLE 4-continued

| Sequence inserted into pUC-Z2 vector | Forward (Fw) primer | Restriction enzyme site at Fw side | Reverse (Rev) primer | Restriction enzyme site at Rev side |
|---|---|---|---|---|
| Comp3_268-503 | SEQ ID NO: 67 | NotI | SEQ ID NO: 71 | SpeI |
| Comp3_383-600 | SEQ ID NO: 68 | NotI | SEQ ID NO: 72 | SpeI |
| Comp3_480-2649 | SEQ ID NO: 69 | NotI | SEQ ID NO: 73 | NotI |

According to the method described in Example 6, *Komagataella pastoris* was transformed with these vectors and the transformation efficiencies (cfu/μg) were calculated. Inserts that yielded a transformation efficiency of 100 or more were expressed as + and those that yielded a transformation efficiency of less than 100 were expressed as—(Table 5).

As a result, among the Comp2 vectors, only the vector containing Comp2_1-111 yielded a high transformation efficiency, suggesting that its autonomous replication sequence locates in the nucleotide sequence of the position 1-111 (SEQ ID NO: 41) of SEQ ID NO: 16. On the other hand, the vector containing Comp2_84-2699 yielded a very low transformation efficiency, suggesting that there is no autonomous replication sequence in Comp2 other than the autonomous replication sequence in the nucleotide sequence of the position 1-111 (SEQ ID NO: 41) of SEQ ID NO: 16.

Among Comp3 vectors, only the vector containing Comp3_383-600 yielded a high transformation efficiency, suggesting that its autonomous replication sequence locates in the nucleotide sequence of the position 383-600 (SEQ ID NO: 42) of SEQ ID NO: 19. On the other hand, Comp3_480-2699 yielded a very low transformation efficiency, suggesting that there is no autonomous replication sequence in Comp3 other than the autonomous replication sequence in the nucleotide sequence of the position 383-600 (SEQ ID NO: 42) of SEQ ID NO: 19.

TABLE 5

| Sequence inserted into pUC-Z2 vector | Transformation efficiency |
|---|---|
| Comp2_1-111 | + |
| Comp2_84-213 | − |
| Comp2_191-291 | − |
| Comp2_84-2699 | − |
| Comp3_268-404 | − |
| Comp3_383-503 | − |
| Comp3_480-600 | − |
| Comp3_268-503 | − |
| Comp3_383-600 | + |
| Comp3_480-2649 | − |

Example 10: Examination of Transformation Efficiency in Combination of Autonomous Replication Sequence and Other Sequence The following vectors were prepared to examine transformation efficiencies of vectors containing an autonomous replication sequence and other sequences.

A DNA fragment having the HindIII recognition sequence added upstream and downstream of 1-111 bp (SEQ ID NO: 41) of the DNA sequence set forth in SEQ ID NO: 16 was prepared by PCR using the DNA fragment consisting of SEQ ID NO: 2 as a template and Primers 21 and 22 (SEQ ID NOs: 39 and 40) and inserted between the HindIII sites of pUC-Z2 to prepare pUC-Z2-ARS2.

A DNA fragment having the NotI recognition sequence added upstream and downstream of SEQ ID NO: 1 was prepared by PCR using a DNA fragment consisting of SEQ ID NO: 1 as a template and Primer 3 (SEQ ID NO: 8) and inserted between the NotI sites of pUC-Z2-ARS2 to prepare pUC-Z2-ARS2-CEN1.

A DNA fragment having the NotI recognition sequence added upstream and downstream of SEQ ID NO: 3 was prepared by PCR using a DNA fragment consisting of SEQ ID NO: 3 as a template and Primer 5 (SEQ ID NO: 10) and inserted between the NotI sites of pUC-Z2-ARS2 to prepare pUC-Z2-ARS2-CEN3.

A DNA fragment having the NotI recognition sequence added upstream and downstream of SEQ ID NO: 4 was prepared by PCR using a DNA fragment consisting of SEQ ID NO: 4 as a template and Primer 6 (SEQ ID NO: 11) and inserted between the NotI sites of pUC-Z2-ARS2 to prepare pUC-Z2-ARS2-CEN4.

A DNA fragment having the NotI recognition sequence added upstream and downstream of the DNA sequence set forth in SEQ ID NO: 13 was prepared by PCR using a DNA fragment consisting of SEQ ID NO: 1 as a template and Primers 3 and 17 (SEQ ID NOs: 8 and 35) and inserted between the NotI sites of pUC-Z2-ARS2 to prepare pUC-Z2-ARS2-Comp1.

A DNA fragment having the NotI recognition sequence added upstream and downstream of the DNA sequence set forth in SEQ ID NO: 19 was prepared by PCR using a DNA fragment consisting of SEQ ID NO: 3 as a template and Primers 5 and 19 (SEQ ID NOs: 10 and 37) and inserted between the NotI sites of pUC-Z2-ARS2 to prepare pUC-Z2-ARS2-Comp3.

A DNA fragment having the NotI recognition sequence added upstream and downstream of the DNA sequence set forth in SEQ ID NO: 22 was prepared by PCR using a DNA fragment consisting of SEQ ID NO: 4 as a template and Primers 6 and 20 (SEQ ID NOs: 11 and 38) and inserted between the NotI sites of pUC-Z2-ARS2 to prepare pUC-Z2-ARS2-Comp4.

A DNA fragment having the NotI recognition sequence added upstream and downstream of the DNA sequence having the nucleotide sequence set forth in SEQ ID NO: 13 upstream of the nucleotide sequence set forth in SEQ ID NO: 12 was prepared by PCR using a DNA fragment consisting of SEQ ID NO: 1 as a template and Primers 3 and 8 (SEQ ID NOs: 8 and 25) and inserted between the NotI sites of pUC-Z2-ARS2 to prepare pUC-Z2-ARS2-Comp KNT1.

A DNA fragment having the NotI recognition sequence added upstream and downstream of the DNA sequence having the nucleotide sequence set forth in SEQ ID NO: 19 upstream of the nucleotide sequence set forth in SEQ ID NO: 18 was prepared by PCR using a DNA fragment consisting of SEQ ID NO: 3 as a template and Primers 5 and 12 (SEQ ID NOs: 10 and 29) and inserted between the NotI sites of pUC-Z2-ARS2 to prepare pUC-Z2-ARS2-Comp3KNT3.

A DNA fragment having the NotI recognition sequence added upstream and downstream of the DNA sequence having the nucleotide sequence set forth in SEQ ID NO: 22 upstream of the nucleotide sequence set forth in SEQ ID NO: 21 was prepared by PCR using a DNA fragment consisting of SEQ ID NO: 4 as a template and Primers 6 and 14 (SEQ ID NOs: 11 and 31) and inserted between the NotI sites of pUC-Z2-ARS2 to prepare pUC-Z2-ARS2-Comp4KNT4.

According to the method described in Example 6, *Komagataella pastoris* was transformed with these vectors and the transformation efficiencies (cfu/µg) were calculated. Inserts that yielded a transformation efficiency of 100 or more were expressed as + and those that yielded a transformation efficiency of less than 100 were expressed as—(Table 6).

As a result, all vectors yielded high transformation efficiencies, indicating that vectors containing CEN1. CEN3, CEN4, Comp1, Comp3, Comp4, Comp1 KNT1, Comp3KNT3 or Comp4KNT4 as well as ARS2 have the autonomous replication activity.

Plasmid maintenance examined for these vectors according to the method described in Example 7 revealed that they were maintained in *E. coli*, suggesting that any of these vectors exists as autonomous replication plasmid in transformed yeast cells.

TABLE 6

| Vector | Transformation efficiency |
| --- | --- |
| pUC-Z2 | − |
| pUC-Z2-ARS2 | + |
| pUC-Z2-ARS2-CEN1 | + |
| pUC-Z2-ARS2-CEN3 | + |
| pUC-Z2-ARS2-CEN4 | + |
| pUC-Z2-ARS2-Comp1 | + |
| pUC-Z2-ARS2-Comp3 | + |
| pUC-Z2-ARS2-Comp4 | + |
| pUC-Z2-ARS2-Comp3KNT1 | + |
| pUC-Z2-ARS2-Comp3KNT3 | + |
| pUC-Z2-ARS2-Comp3KNT4 | + |

Example 11: Examination of Stability of Plasmid

The yeast transformant obtained in Example 6 was inoculated to 3 ml of the YPD medium and cultured with shaking at 30° C. overnight. Next, 3 µl of this liquid culture was inoculated to 3 ml of the fresh YPD medium and cultured with shaking at 30° C. overnight. This operation was repeated 3 times (3 nights) and then the finally obtained liquid culture was diluted and then plated onto YPD agar plates (1% yeast extract bacto (manufactured by Difco Laboratories), 2% polypeptone (manufactured by Nihon Pharmaceutical Co., Ltd.), 2% glucose, 1.5% agarose). 96 strains grown in static culture at 30° C. for 3 days were selected, plated onto YPD agar plates and YPDZeocin™ selection agar plates, and statically cultured at 30° C. overnight.

As a result, relative to the samples from yeasts transformed with pUC-Z-Comp1, pUC-Z-Comp2, pUC-Z-Comp3, or pUC-Z-Comp4, the samples from the yeasts transformed with pUC-Z-Comp1KNT1, pUC-Z-Comp2KNT2, pUC-Z-Comp3KNT3, or pUC-Z-Comp4KNT4 yielded clearly more colonies grown on both plates (Table 7). This indicates that SEQ ID NO: 12, 15, 18, and 21 exhibited a positive effect on the stability of the vector as also illustrated in Example 4. Moreover, relative to the samples from yeasts transformed with pUC-Z-Comp1KNT1, pUC-Z-Comp2KNT2, pUC-Z-Comp3KNT3, or pUC-Z-Comp4KNT4, the samples from the yeasts transformed with pUC-Z-CEN1, pUC-Z-CEN2, pUC-Z-CEN3, or pUC-Z-CEN4 yielded clearly more colonies grown on both plates (Table 7). This indicates that a special stabilization effect is exhibited by having complementary nucleotide sequences upstream and downstream of a centromere DNA center sequence and that plasmid vectors having a centromere DNA sequence are stably maintained even in subculture with no selective pressure.

Plasmids were prepared from grown yeasts and introduced into *E. coli* HST08 Premium competent cells to confirm that *E. coli* colonies appear on LBAmp selection agar plate (1% Trypton (manufactured by Nacalai Tesque, Inc.), 1% sodium chloride, 0.5% yeast extract bacto (manufactured by Difco Laboratories), 0.01% ampicillin sodium (manufactured by Wako Pure Chemical Industries, Ltd.)) like Example 7. Moreover, plasmids prepared from the *E. coli* colonies were confirmed to be the same as the vectors introduced into the yeasts.

TABLE 7

| Vector | Number of growing colonies (YPD agar medium) | Number of growing colonies (YPD Zeocin agar medium) |
| --- | --- | --- |
| pUC-Z-CEN1 | 96 | 96 |
| pUC-Z-CEN2 | 96 | 95 |
| pUC-Z-CEN3 | 96 | 94 |
| pUC-Z-CEN4 | 96 | 96 |
| pUC-Z-Comp1 | 96 | 3 |
| pUC-Z-Comp2 | 96 | 3 |
| pUC-Z-Comp3 | 96 | 4 |
| pUC-Z-Comp4 | 96 | 2 |
| pUC-Z-Comp1KNT1 | 96 | 45 |
| pUC-Z-Comp2KNT2 | 96 | 38 |
| pUC-Z-Comp3KNT3 | 96 | 42 |
| pUC-Z-Comp4KNT4 | 96 | 44 |

Example 12: Examination of Stability of Plasmid when Autonomous Replication Sequence is Combined with Other Sequence Yeast Transformants were prepared according to Example 6 using pUC-Z2-ARS2, pUC-Z2-ARS2-CEN1, pUC-Z2-ARS2-CEN4, pUC-Z2-ARS2-Comp1, pUC-Z2-ARS2-Comp4, pUC-Z2-ARS2-Comp1 KNT1, pUC-Z2-ARS2-Comp4KNT4 prepared in Example 10.

Subsequently, stability of the plasmids was examined according to Example 11 using these yeast transformants.

The result is shown in Table 8. Samples from yeasts transformed with pUC-Z2-ARS2 did not yield any colony grown on both plates. This indicates that a plasmid vector having only an autonomous replication sequence is not stably maintained in subculture without the selective pressure.

On the other hand, samples from yeasts transformed with pUC-Z2-ARS2-Comp1 KNT1 or pUC-Z2-ARS2-Comp4KNT4 yielded clearly more colonies grown on both plates. This indicates that SEQ ID NO: 12 and 21 exhibited a positive effect on the stability of vector as also illustrated in Example 4. Moreover, samples from yeasts transformed with pUC-Z2-ARS2-CEN1 or pUC-Z2-ARS2-CEN4 yielded even more colonies grown on both plates. This indicates that a special stabilization effect is exhibited by having complementary nucleotide sequences upstream and downstream of a centromere DNA center sequence, as also illustrated in Examples 4 and 11, and that plasmid vectors having a centromere DNA sequence are stably maintained even in subculture with no selective pressure.

TABLE 8

| Vector | Number of growing colonies (YPD agar medium) | Number of growing colonies (YPD Zeocin agar medium) |
|---|---|---|
| pUC-Z2-ARS2 | 96 | 0 |
| pUC-Z2-ARS2-CEN1 | 96 | 96 |
| pUC-Z2-ARS2-CEN4 | 96 | 96 |
| pUC-Z2-ARS2-Comp1 | 96 | 5 |
| pUC-Z2-ARS2-Comp4 | 96 | 4 |
| pUC-Z2-ARS2-Comp1KNT1 | 96 | 45 |
| pUC-Z2-ARS2-Comp4KNT4 | 96 | 44 |

Example 13: Confirmation that the pUC-Z2 Vectors are Equivalent to the pUC-Z Vectors Vectors were prepared according to Example 5 using pUC-Z2 prepared in Example 8 instead of pUC-Z. These vectors were examined according to Examples 6-7 and Example 11. The results obtained using pUC-Z2 and those with pUC-Z were similar.

Example 14: Confirmation that the Position 681-1535 of SEQ ID NO: 5 is Equivalent to SEQ ID NO: 5

Vectors were prepared according to Examples 1 and 5 using the nucleotide sequence of the position 681-1535 of SEQ ID NO: 5 instead of the nucleotide sequence set forth in SEQ ID NO: 5. These vectors were examined according to Examples 6-7 and Example 11. The results obtained using the nucleotide sequence of 681-1535 of SEQ ID NO: 5 were similar to the results obtained using the nucleotide sequence set forth in SEQ ID NO: 5.

All publications, patents and patent applications cited herein shall be incorporated herein by reference as they are.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. A vector comprising a nucleotide sequence selected from any one of the following (a) to (d):
   (a) the nucleotide sequence set forth in SEQ ID NO: 12, 15, 18, or 21;
   (b) the nucleotide sequence complementary to the nucleotide sequence set forth in SEQ ID NO: 12, 15, 18, or 21, wherein (a) and (b) hybridize under stringent conditions;
   (c) the nucleotide sequence having 90% or more sequence identity with the nucleotide sequence set forth in SEQ ID NO: 12, 15, 18, or 21; and
   (d) the nucleotide sequence set forth in SEQ ID NO: 12, 15, 18, or 21 in which a total of 1 to 50 nucleotides are substituted, deleted, or inserted; and
   one or more selected from the group consisting of an exogenous gene, an endogenous gene that is artificially incorporated, a cloning site containing one or more restriction enzyme recognition sites, a nucleotide sequence of a selection marker gene, a nucleotide sequence of a reporter gene, an autonomous replication sequence, a regulatory sequence, an overlap region to be used in a cloning system, a centromere DNA sequence derived from a biological species different from a biological sequence in which the nucleotide sequence (a) to (d) is derived, and a telomere DNA sequence derived from a biological species different from a biological sequence in which the nucleotide sequence (a) to (d) is derived.

2. The vector of claim 1, further comprising nucleotide sequences selected from any one of the following (e) to (g) located upstream and downstream of the nucleotide sequence selected from any one of (a) to (d):
   (e) an upstream nucleotide sequence and a downstream nucleotide sequence that are complementary to each other;
   (f) an upstream nucleotide sequence and a downstream nucleotide sequence that hybridize with each other under stringent conditions;
   (g) an upstream nucleotide sequence and a downstream nucleotide sequence, each of which has 90% or more sequence identity with each other.

3. The vector of claim 2, wherein the upstream and/or the downstream nucleotide sequence selected from any one of (e) to (g) has a GC content equal to or lower than 41%.

4. The vector of claim 2, wherein at least one of the upstream and downstream nucleotide sequences selected from any one of (e) to (g) is yeast chromosomal DNA from the genus *Komagataella*.

5. The vector of claim 2, wherein the vector has a binding capacity to a centromere protein (CENP).

6. The vector of claim 2, wherein the nucleotide sequences selected from any one of (e) to (g) are each 2800 nucleotides or less.

7. The vector of claim 6, wherein the nucleotide sequences selected from any one of (e) to (g) are each 1900-2800 nucleotides.

8. The vector of claim 2, wherein the upstream nucleotide sequence or the downstream nucleotide sequence selected from any one of (e) to (g) is further selected from any one of the following (h) to (k):
   (h) the nucleotide sequence set forth in SEQ ID NO: 13, 16, 19, or 22;
   (i) the nucleotide sequence complementary to the nucleotide sequence set forth in SEQ ID NO: 13, 16, 19, or 22, wherein (h) and (i) hybridize under stringent conditions;
   (j) the nucleotide sequence having 90% or more sequence identity with the nucleotide sequence set forth in SEQ ID NO: 13, 16, 19, or 22;
   (k) the nucleotide sequence set forth in SEQ ID NO: 13, 16, 19 or 22 in which a total of 1 to 50 nucleotides are substituted, deleted, or inserted.

9. The vector of claim 2, wherein the upstream nucleotide sequence or the downstream nucleotide sequence selected from to any one of (e) to (g) is further selected from any one of the following (1) to (o):
   (l) the nucleotide sequence set forth in SEQ ID NO: 14, 17, 20, or 23;
   (m) the nucleotide sequence complementary to the nucleotide sequence set forth in SEQ ID NO: 14, 17, 20, or 23, wherein (1) and (m) hybridize under stringent conditions;
   (n) the nucleotide sequence having 90% or more sequence identity with the nucleotide sequence set forth in SEQ ID NO: 14, 17, 20, or 23;
   (o) the nucleotide sequence set forth in SEQ ID NO: 14, 17, 20, or 23 in which a total of 1 to 50 nucleotides are substituted, deleted, or inserted.

10. The vector of claim 2, wherein the upstream nucleotide sequence and the downstream nucleotide sequence selected from any one of (e) to (g) further comprise nucleotide sequences selected from any one of the following (p) to (s):
    (p) the upstream nucleotide sequence set forth in SEQ ID NO: 13 and the downstream nucleotide sequence set forth in SEQ ID NO: 14;
    (q) the upstream nucleotide sequence set forth in SEQ ID NO: 16 and the downstream nucleotide sequence set forth in SEQ ID NO: 17;
    (r) the upstream nucleotide sequence set forth in SEQ ID NO: 19 and the downstream nucleotide sequence set forth in SEQ ID NO: 20;
    (s) the upstream nucleotide sequence set forth in SEQ ID NO: 22 and the downstream nucleotide sequence set forth in SEQ ID NO: 23.

11. The vector of claim 1, further comprising any one of the following (t) to (w):
    (t) the nucleotide sequence set forth in SEQ ID NO: 41, 42, 85, or 86;
    (u) the nucleotide sequence complementary to the nucleotide sequence set forth in SEQ ID NO: 41, 42, 85, or 86, wherein (t) and (u) hybridize under stringent conditions;
    (v) the nucleotide sequence having 90% or more sequence identity with the nucleotide sequence set forth in SEQ ID NO: 41, 42, 85, or 86;
    (w) the nucleotide sequence set forth in SEQ ID NO: 41, 42, 85, or 86 in which a total of 1 to 50 nucleotides are substituted, deleted, or inserted.

12. The vector of claim 1, further comprising an autonomous replication sequence (ARS) other than SEQ ID NO: 12, 15, 18, or 21.

13. The vector of claim 1, wherein when the vector is included in a host other than yeast, the vector is an autonomous replication vector.

14. The vector of claim 1, further comprising an autonomous replication sequence (ARS) and/or a centromere DNA sequence from a biological species different from a biological species of *Komagataella pastoris*.

15. A method for transforming a cell, comprising introducing a vector of claim 1 into a cell.

16. A transformant obtained by transforming a cell with a vector of claim 1.

17. The transformant of claim 16, wherein the cell is yeast or *Escherichia coli*.

18. The transformant of claim 17, wherein the cell is a methylotrophic yeast.

19. The transformant of claim 18, wherein the methylotrophic yeast is a yeast of the genus *Komagataella* or the genus *Ogataea*.

\* \* \* \* \*

SEQUENCE LISTING

```
<160> NUMBER OF SEQ ID NOS: 86

<210> SEQ ID NO 1
<211> LENGTH: 5354
<212> TYPE: DNA
<213> ORGANISM: Komagataella pastoris

<400> SEQUENCE: 1
aatgtcaagt acttaacttt tgtctctgaa accaagtttc ctcaaagata aacttgttat      60
tcaagctagt aggtacaaca agtgtaagct gaagccgaaa tcaaatacaa ggcaaaacga     120
tctttgaaat accgtggaaa aagcaaaatc cccctggaag ttacaaacca cttgctaatc     180
tcccaatata gctgtgcata atcaccatct ggctagcaga atttaaatgt acatgtggct     240
gttatactgt ctggattcca tatctactgc atgcacagcg acgatttatc aaaatcatga     300
taaagtttga gttggcatcc aaattatgtt cactacacct tggaatcttt tttcctcatc     360
tggcaggttc ggatagcgta ataattttg atgctttcaa gacagcacaa tcattaactt      420
ccatcatatc acaagaaccc agtagtaata cctccttaag attgttttca atctgagtgt     480
ttatagacct acacgtgcaa atgaaaaagg acgtctcagc tttgtggaac ttgtcacaat     540
ctggcaaaat ctagtagagg tagtaagcct aattcttaat aactgatagt ctcttacttc     600
aatttgataa tttagaacaa ttacattcac caattctgta cgaactggca actaatagg      660 caaaaacaat ccgttttgat ccataaattt gatctggttg atcagataga atttaatggg     720
tagtgattta tcaacaacaa ttaggcctga actgtaaaga aaaacatcaa ataaagtaca     780
ttctcagggt ttttcacctt acttccaatg accatgcttt tcccgatggg cagatacatc     840
ttcagctaat tggagtatgg aagtcaatat acgtgaagtc ccctctagaa gcaattttcg     900
gtgcttgcag cacgttatca tgttttcaga gccttgacca gacagaatct gatccaaggc     960
aaacgaggga aacagttaaa gtagaagata ccttacatag tcaactaaat ggtattgata    1020
aattctgatt atgagaacaa aacttcaaaa ctatcggtgt gtatcatcta gttgaggttt    1080
tatatctatg tatgatgcta tgtagacctt aacttgaatg aagcactctc caataagatt    1140
```

```
ggccaaagtt caatacaata cttgccacat gaaacagtct aacttctaga gaagtttgct   1200
ggcccttaga taaggctgat agccactatt tacagatagc cctttgctta tgcttgtggg   1260
taatgaacta gggaggtact ggttggtcga tgaaattccg gcagactttt cattcgtacg   1320
acgggtacca agagaaaaat tatgtgttaa agggagcttc aatgtaggcc cataagttta   1380
ggagcaaaat atggcgaata tacaaaatct ataaacctac tcactgttaa gacaaataca   1440
ggtaaatctt cggatatagg ggggacgcca aacttaagat ctggtctacc aataaaccta   1500
tgcctcaaac caaactcata ctcttgatga atactgatt gattgagtga aagttaaca    1560 gcatcggtta gtcaatcgaa aagttcaatc aatgaacagt ggtagtcctt ctacggtact   1620
taaattccaa tcccaaaata atatcaataa tgaacaggaa tcctccaaga gaatctttct   1680
accatgagaa ttgggaaaaa cagtatccat tcaagaacta gatctacgta ccagaacgcc   1740
aggtttctac gcttaatcac tctatcaaat acaactcaag ctctaagttc ttgcgggttc   1800
agcttacgtt tacgcacaaa acaactactg ccccgaaacc agtaaaaata cattacaaat   1860
gctacgaata agatgatcat agtagccaca ataattcgac ctgatagctc taaaacacgt   1920
ctttaggttg atctgacaat agtatgaacc gataatgaac actataacgg attgctaata   1980
acgaacccag aaatgaaaca taggaatact accatggcac gaccagctat gcgctaattg   2040
gtgcaaagta aagttagctc attcagtgac accataactc cacccattaa agaaatgtga   2100
tcataataag cttgagttta ataccctacag gttgtcaagt aaaaattata tagttttgtga  2160 aaaacgattc cagaaacaga actcttcctg aatccagcaa ggggaaatat acaacggacc   2220
atgacctagt actactcaaa gaacactcaa tgagaatata aaagtgttcg caggatacca   2280
ttcgcaacat cttgcagtat ctcgtattcc cgcgatggaa aacgtagcag taatcgacgc   2340
ctagtagtac tagcactaac atgctgctga atgatgattg aacatattcc ttcaataaag   2400
aagaaggaag tacaactgta taactagaat tgacaaaact tggaaagact aggtaacgct   2460
cagtcagtag gtccgtttcc actccttctt ttgtgaccga ctcagactga aacagcgcag   2520
ttgcgttaga ttagccataa tacagtggtg aggtctgaca cctactgacg taatagagtg   2580
aaccaagtat gcgtgatccc aggtttagca aataaggata cagagcccca caattcgtaa   2640
cgataatgac tacgtatata gatgttgtac agatcagtga gactttctct aattatctat   2700
ggattgagaa agttattagg agggacacac gacgacggct ttgacctact tcccaaaagt   2760
ctccatcgat gtctcaatat gattgatggc aagtacacaa atgaaggtac taaggtggaa   2820
ttgataggta ttgctatcca gaaagacaag tcgtagctag aaacgtctga ccctttgaac   2880
tcacgtagct tcgtactttt gggagcccct gcccagtaca aagtttaagc tgagtcccgg   2940
tatattttgc tgtcgagcaa ccgtgtaaat attgttttgt aagttcggct acgagcaaag   3000
agctcatacc ttgtactgcc tgctaccaag ctttttctg tggggattca tgaatccgga   3060
agaagatgca tctattcatt gctggatttg caggcaaatg atgtacgctt tcacaacaga   3120
atccatcaac tattagttgg aagattagaa gtatatttca atatagttca gcaaagagct   3180
atagtcacat acttttttt gctcgatgtc aattcgaggc aattagcttt agagcaaatt   3240
tgttaggttt tgcttcagct ttctaatgcc tcacaacttc attccttatc acgcagcgaa   3300
agaaccggcg acagtatcaa tcacttcacc catgatggca tagtagtatt cctatgtttc   3360
acttctgggt tcgttattag caatccgtta tagtgttcat tatcggttca tactattgtc   3420
agatcaacct aaagacgtgt tttagagcta tcaggtcgaa ttattgtggc tactatgatc   3480
atcttattcg tagcatttgt aatgtatttt tactggtttc ggggcagtag ttgttttgtg   3540
```

```
cgtaaacgta agctgaaccc gcaagaactt agagcttgag ttgtatttga tagagtgatt    3600
aagcgtagaa acctggcgtt ctggtacgta gatctagttc ttgaatggat actgttttc    3660 ccaattctca tggtagaaag attctcttgg aggattcctg ttcattattg atattatttt    3720
gggattggaa tttaagtacc gtagaaggac taccactgtt cattgattga acttttcgat    3780
tgactaaccg atgctgttaa cttctcactc aatcaatcag tatttcatca agagtatgag    3840
tttggtttga ggcataggtt tattggtaga ccagatctta agtttggcgt cccccctata    3900
tccgaagatt tacctgtatt tgtcttaaca gtgagtaggt ttatagattt tgtatattcg    3960
ccatattttg ctcctaaact tatgggccta cattgaagct ccctttaaca cataattttt    4020
ctcttggtac ccgtcgtacg aatgaaaagt ctgccggaat tcatcgacc aaccagtacc    4080 tccctagttc attacccaca agcataagca aagggctatc tgtaaatagt ggctatcagc    4140
cttatctaag ggccagcaaa cttctctaga agttagactg tttcatgtgg caagtattgt    4200
attgaacttt ggccaatctt attggagagt gcttcattca agttaaggtc tacatagcat    4260
catacataga tataaaacct caactagatg atacacaccg atagttttga agttttgttc    4320
tcataatcag aatttatcaa taccatttag ttgactatgt aaggtatctt ctactttaac    4380
tgtttccctc gtttgccttg gatcagattc tgtctggtca aggctctgaa acatgataa    4440 cgtgctgcaa gcaccgaaaa ttgcttctag aggggacttc acgtatattg acttccatac    4500
tccaattagc tgaagatgta tctgcccatc gggaaaagca tggtcattgg aagtaaggtg    4560
aaaaaccctg agaatgtact ttatttgatg tttttctta cagttcaggc ctaattgttg    4620
ttgataaatc actacccatt aaattctatc tgatcaacca gatcaaattt atggatcaaa    4680
acggattgtt tttgccctat tagttgccag ttcgtacaga attggtgaat gtaattgttc    4740
taaattatca aattgaagta agagactatc agttattaag aattaggctt actacctcta    4800
ctagattttg ccagattgtg acaagttcca caaagctgag acgtccttt tcatttgcac    4860 gtgtaggtct ataaacactc agattgaaaa caatcttaag gaggtattac tactgggttc    4920
ttgtgatatg atggaagtta atgattgtgc tgtcttgaaa gcatcaaaaa ttattacgct    4980
atccgaacct gccagatgag gaaaaaagat tccaaggtgt agtgaacata atttggatgc    5040
caactcaaac tttatcatga ttttgataaa tcgtcgctgt gcatgcagta gatatggaat    5100
ccagacagta taacagccac atgtacattt aaattctgct agccagatgg tgattatgca    5160
cagctatatt gggagattag caagtggttt gtaacttcca gggggatttt gcttttccca    5220
cggtatttca aagatcgttt tgccttgtat ttgatttcgg cttcagctta cacttgttgt    5280
acctactagc ttgaataaca agtttatctt tgaggaaact tggtttcaga gacaaaagtt    5340
aagtacttga catt                                                    5354
```

<210> SEQ ID NO 2  
<211> LENGTH: 6655  
<212> TYPE: DNA  
<213> ORGANISM: Komagataella pastoris

<400> SEQUENCE: 2

```
ccaatcaaac aaggtgactt gcgcgaagca atgatttgtg gatgggctgc ggtatggcag      60
cataacaatg caacgctatt tcagaaattg taaagtgtaa aggaaatatt caaccctata     120
aagaatctac cgaaacgtag gataaataat ttccacagag tacactttg gttttttatgg     180 acggcgttga gttgcacaga tgatggaata ttgtgataaa atacgctata taattttgga     240
```

```
gaccctaaga tcaagtggac taggtcgatt gcgtatatta gggtattaaa gacttactta    300
attctataag agctcggcaa gctatattct cagttccttc gcagtcgacc ttcagtgccc    360
aaaactttaa agtggacggg tgttttctaa agattgctat tgttcaattg cccggttttt    420
taaccgctga aaaccagtgg caagagtgga ctacgtgcgc attgcaattt gtataatcca    480
tataattttg ttccacggcc ttaagttatt gtactgtttg ctcaattttg aagcggaata    540
tccgtcctag tctcgaatcc ttatttaagt accggtatca tttgcatatc ctctcagccc    600
tcaaacgccc attctttata gtaatggtta tgtattaatc gactacgatg attgactcag    660
ggaggcacga atagtataat ttgtaacttg cagtgggaag ctaatttcgg gtgtcttgaa    720
agacgaggtt aaaaatttga acccaaaccg atttaccgg agatcctacc tcaaattaga     780
acaactttaa agcttccaag gaattgaaat tccatcttta tagaccggta attctttgaa    840
gagtaatcaa tgtaagagca agttctaaag agaggatcca aattccttct gatagcaatt    900
gtaaggagct gcaaagttca acataatatt tgcgatagta accgtcctac ggatacttaa    960
atcggtatca aagagtgacc aatcctgaat cagtgtagtg caaaaagaaa taacgatgat   1020
aaacgaatca agattctgat gagttgtcca agacggggct atcataatat ttaaaaaata   1080
gaacctacta atttaacaag gtaaatctca tagatttaag tttcacgact agcttagcta   1140
ccactcaaat aagctcccgc ttgttcattc ggctggggtc tccaatctcc atctccaatg   1200
gatatttttt ttttaagtgg agagagatgt tcagtaaact gtgagttcag ttgtcagaag   1260
caaccaatat ttaccatgga gacgaataag cagatattat atactctatt tttacagccc   1320
ttttgtataa tcctcaggga tggttggcgc ttccctgtgt tccaagtaac cacactcttc   1380
aagttggaaa tgcaaaaggt cccaatgcat gctcccaagt catactgaat acagagatag   1440
attctttgaa ttggatcgat ctctaatgaa attcatggat gagaagagag tgttaaaaac   1500
tttgccccaa ctaaatactt tatctgaatg aatcattaaa gaacacgaca agttcagtat   1560
gttgcttgga gcctccgatt cacagtcttg taagtagtgc gtgttttcaa atatttgcat   1620
tagcaatccc tccaagtagc ccacataggg accaaaaaaa tagtatagtt tgttttgggg   1680
ggaagggagt aggaattgct ttcgaaatgg ttaactcctg cttagtttca tttaaaaaat   1740
gaatagagaa gtagatacag aatactttgt aagactgctt acatgaatga tgccagagag   1800
tgtgccgaaa gatctacatg ctactaaatt tactatcaat agggataaaa tgtattaggc   1860
tacctactat gccgtattgg aaaggcgaag tgctttgtat gcaagggatt ggggcatagg   1920
caaacggatc tatgacaaga gatacgaaat tacttctgtt acccactctg ctcctaccaa   1980
accaaatata tctgtgacca aaaatatcat ttgtcttgtg ctccacatag cggccaggct   2040
caaagagaac actagatctg ctttcagaca ttaccgcgtg caaatatgac aagtcactag   2100
gtgatgaact agtcgataaa accaaaaacg atctgatcaa taacttgaca acatcgttct   2160
tatcggattt ctagctcttg aatagtcaaa tgctgagttc aattttaaag tgaatatttt   2220
tcaccgaagt cgatttttagc ccattagtca aacaacagaa gagaaaagac aaaccttctt   2280
tttcatgaca catgaaacaa atcacaaaaa ttgagtcata ttacggtttc aatttctgct   2340
gtttgtataa gtcattggct ggcaaacaca tctcctggcc tcatactgaa aatatatgaa   2400
gataactgct tctaccaatt tcaattgatc aaggttctac ccatacgtat agttccagag   2460
catgatgtta gggaaactta cagggatgat gtgggccaca gcataatatc aacaatacct   2520
aacaatcggt atttaattca tagatattca ataccaattc tccacgatga aaggggcga    2580 ctcctcttct tggacgttct gaaaatacag gtacgctcac gtcagtgcct gagcacatac   2640
```

```
agcgacgtta gtatcaatct tcctgggaca tctctaatgc tctaaaatga agaaaaagta    2700
aaattagtat cagttggcca tgcgaccaag cctgttggaa cgcaaaagca tatccgaatt    2760
atggttggaa attaccttcg accttcaaac actaaactct tcacagggct attattccag    2820
ctattgcaga acttcatacg aatttgggct tgctaaaaat tggcaggatc gttcttcaat    2880
aactgaatac agtattgtac ctattcaagc agttagtcca tacttagggc cttcctagcc    2940
tgtccagtct accattaacg aaagttctga gctgtgtcta tccaaattaa tttgtgtcag    3000
aacctacgta accactataa gtctcataac gttttttgaaa tagataaaat tagtttgttt    3060
gatcattcaa gcacattata gataatattc caaaaagaaa gtttcaaggt gccccttgga    3120
catataaaac tttgccacgg tgctaaactt aaaagaatga tcttccaaaa atacggaata    3180
gaataatcta ttttttagaag agaagactaa aaatcgagcg atactatgaa tgtctgttac    3240
aaactgaatt tttgcacgta acgaatactt tgaaacaatc ctcaaaatct tgttttggtg    3300
tttgtcgagt agtcttttacc aggccgaatc ctgtagttaa aaataatttt ctatttggac    3360
aactaagggt atcccctcaa gtttggcttt tgtgtacctt gttcggaaag ctccgttct    3420 gcaattctgc agcaaccttg tcattagctg tgtaatgctc gctggtgagt agcataagtc    3480
attccaatgg taactaccaa gcttgtaata taaccaccag cacctccatt cagtagtagc    3540
aatgagcaag gtcggagatt gcttttaagc gaggtttcaa agtaatcttg tagttttgct    3600
ttgtcgaaaa atggccacgg cttacacata cagttcgtcc accagatctt taggcttcat    3660
caacaaagtt ttcgacttcg ttgtctatag gttttattct ttatcagcgt cagactatga    3720
tcgtactagt ttgagctgaa gcccatcagg atgtttacca ctccagtttt gtaatttccg    3780
cggctatcta gggctacgtt gtccattgcc gagtttatat atgacatcac attaggcagt    3840
aattctccat gcttcttttt cgataatgtt ttggtctagg ttcgtgcatg aaatttttc    3900 ttcatccaga ctatctctgc gctgcactgt tcacatagcc aactgatact gatttcactt    3960
tttcttcatt ttagagcatt agagatgtcc caggaagatt gatactaacg tcgctgtatg    4020
tgctcaggca ctgacgtgag cgtacctgta ttttcagaac gtccaagaag aggagtcgcc    4080
ccttctcatc gtggagaatt ggtattgaat atctatgaat taaataccga ttgttaggta    4140
ttgttgatat tatgctgtgg cccacatcat ccctgtaagt ttccctaaca tcatgctctg    4200
gaactatacg tatgggtaga accttgatca attgaaattg gtagaagcag ttatcttcat    4260
atattttcag tatgaggcca ggagatgtgt ttgccagcca atgacttata caaacagcag    4320
aaattgaaac cgtaatatga ctcaattttt gtgatttgtt tcatgtgtca tgaaaagaa    4380 ggtttgtctt ttctcttctg ttgtttgact aatgggctaa aatcgacttc ggtgaaaaat    4440
attcacttta aaattgaact cagcatttga ctattcaaga gctagaaatc cgataagaac    4500
gatgttgtca agttattgat cagatcgttt ttggttttat cgactagttc atcacctagt    4560
gacttgtcat atttgcacgc ggtaatgtct gaaagcagat ctagtgttct ctttgagcct    4620
ggccgctatg tggagcacaa gacaaatgat attttttggtc acagatatat ttggtttggt    4680
aggagcagag tgggtaacag aagtaatttc gtatctcttg tcatagatcc gtttgcctat    4740
gccccaatcc cttgcataca aagcacttcg cctttccaat acggcatagt aggtagccta    4800
atacatttta tccctattga tagtaaattt agtagcatgt agatctttcg gcacactctc    4860
tggcatcatt catgtaagca gtcttacaaa gtattctgta tctacttctc tattcatttt    4920
ttaaatgaaa ctaagcagga gttaaccatt tcgaaagcaa ttcctactcc cttcccccca    4980
```

-continued

| | |
|---|---|
| aaacaaacta tactatttttt ttggtcccta tgtgggctac ttggagggat tgctaatgca | 5040 |
| aatatttgaa aacacgcact acttacaaga ctgtgaatcg gaggctccaa gcaacatact | 5100 |
| gaacttgtcg tgttctttaa tgattcattc agataaagta tttagttggg gcaaagtttt | 5160 |
| taacactctc ttctcatcca tgaatttcat tagagatcga tccaattcaa agaatctatc | 5220 |
| tctgtattca gtatgacttg ggagcatgca ttgggacctt ttgcatttcc aacttgaaga | 5280 |
| gtgtggttac ttggaacaca gggaagcgcc aaccatccct gaggattata caaaagggct | 5340 |
| gtaaaaatag agtatataat atctgcttat tcgtctccat ggtaaatatt ggttgcttct | 5400 |
| gacaactgaa ctcacagttt actgaacatc tctctccact taaaaaaaaa atatccattg | 5460 |
| gagatggaga ttggagaccc cagccgaatg aacaagcggg agcttatttg agtggtagct | 5520 |
| aagctagtcg tgaaacttaa atctatgaga tttaccttgt taaattagta ggttctatttt | 5580 |
| tttaaatatt atgatagccc cgtcttggac aactcatcag aatcttgatt cgtttatcat | 5640 |
| cgttatttct ttttgcacta cactgattca ggattggtca ctctttgata ccgatttaag | 5700 |
| tatccgtagg acgttactta tcgcaaatat tatgttgaac tttgcagctc cttacaattg | 5760 |
| ctatcagaag gaatttggat cctctcttta gaacttgctc ttacattgat tactcttcaa | 5820 |
| agaattaccg gtctataaag atggaatttc aattccttga aagctttaaa gttgttctaa | 5880 |
| tttgaggtag gatctccggt aaaatcggtt tgggttcaaa tttttaacct cgtctttcaa | 5940 |
| gacacccgaa attagcttcc cactgcaagt tacaaattat actattcgtg cctccctgag | 6000 |
| tcaatcatcg tagtcgatta atacataacc attactataa agaatgggcg tttgagggct | 6060 |
| gagaggatat gcaaatgata ccggtactta aataaggatt cgagactagg acggatattc | 6120 |
| cgcttcaaaa ttgagcaaac agtacaataa cttaaggccg tggaacaaaa ttatatggat | 6180 |
| tatacaaatt gcaatgcgca cgtagtccac tcttgccact ggttttcagc ggttaaaaaa | 6240 |
| ccgggcaatt gaacaatagc aatctttaga aaacaccgt ccactttaaa gttttgggca | 6300 |
| ctgaaggtcg actgcgaagg aactgagaat atagcttgcc gagctcttat agaattaagt | 6360 |
| aagtctttaa caccctaata tacgcaatcg acctagtcca cttgatctta gggtctccaa | 6420 |
| aattatatag cgtatttttat cacaatattc catcatctgt gcaactcaac gccgtccata | 6480 |
| aaaaccaaaa gtgtactctg tggaaattat ttatcctacg tttcggtaga ttctttatag | 6540 |
| ggttgaatat ttccttttaca ctttacaatt tctgaaatag cgttgcattg ttatgctgcc | 6600 |
| ataccgcagc ccatccacaa atcattgctt cgcgcaagtc accttgtttg attgg | 6655 |

```
<210> SEQ ID NO 3
<211> LENGTH: 6181
<212> TYPE: DNA
<213> ORGANISM: Komagataella pastoris

<400> SEQUENCE: 3
```

| | |
|---|---|
| aactcaatgt ttttgtttct ctcgacgaaa cgttttttgct tagcatttcg gtatcttaaa | 60 |
| ccgtgtgatt ttaagtctca taaccttttta catacaggat caataataat attattgttg | 120 |
| atacaatata ggattagaat acatagattc tgatgttcga atcaatcaat gtcttaatat | 180 |
| tcacgtactt gtataccctc tgattccaca ttggtccaac ggaatcttct agcaacagcc | 240 |
| agttgcacta gatgtggttc tccaccagaa attatagtac tgacagattt tttggtttac | 300 |
| ggtgagaggc tccaattttcc aaagctaaac caatttcttc ataagcaacc tccacgcgcg | 360 |
| cttttagtat gatgtagaaa ctggacctaa agatcgacca atacttgctt acacggcagc | 420 |
| gcgaaataaa agacattgat aatgtagagt aagtactatt tcttcaaaag atagaaccac | 480 |

```
tctcagaggc taactagaag atctaaaacg gatgtacagc taatatgttt cgaggcaatc      540
atgttcaggt gcgcctcaag tggctcttaa tctattttaa agcataatcc acgaaaattt      600
cgatacagag agatacgtca taaactgaga acgatagtta gaggcatagc ttcggcaatg      660
ttcgataaac aagtcaacga gtcagaattt catgtttctt ttttttcttg tagtaatatg      720
taataaccga atcagataac ttgccagtaa tgacctgagc tctataaatt gaaaccgcta      780
caaaaagtaa gggatcgtgt taagggcaca gagaagaaag tgtaagaag taagctagcg      840 ttgtacaaca actcaaaagc atggagcccg gtgggtacta gataataaga acaaggtttc      900
agtgagttta caagttcata aaacacggaa cctggcaaca tagcatacca gtaaatcgat      960
ttgaagaact ctattaggct ggcagcctct ctcaatcaat agtctaaaac ggttaagaga     1020
cacaatcatc tctaggtgtc gttgtggtct accatcgaaa cactggaaat caatccaatg     1080
aacttcaagt gatatatttt tcaagagtct tcaaagacca agcaatgttc ttattgattg     1140 ataatttta agttgaagtc taaatttgta gcagtgaagt ctgagcaggg ggaatgttaa     1200
gccatatcta atagtaccta ttagacgctt gattgccgtt tgcaaatatg ccatgtttct     1260
ttgaaaccaa aaccacgtaa gggggcttaa gttttcggct taggattgtt acggagctca     1320
aaccaaataa ggcagagagc atacaaaacg tttattaaaa agaacaacta cttctggata     1380
gctcaattat cttttgtttc ttttgaggcg tgcccttcat gacatgacat tgcatccata     1440
caattaatag tagatagggg aggataagtt tgctagtgtg agcatttaga gcaaggggtc     1500
agtttcctcc atctgcctac tctgctccat ttaaaagcga gccgattgcc ataagcttgc     1560
tcacgtagat aggacttcaa aaagacgtta agaggctgct ctctagaata cgatggaata     1620
aacaaatctc gttagtttct tgaaacggaa agtacatgta ggataattgc tggatcattc     1680
ggaagctaaa attggtcctt tccccaaaga caatcgacta tagttcctga agcttcctga     1740
ggtgagctgg atagaaccag aagatagtac ctataacgtc aacaacaact gaaactacag     1800
atggaagagc taggcatatc cataggggat agccatagaa aactttgatt gacgcagcaa     1860
atcgagacgt taacctgaag ctgccataac ttcaggaact tgaacacaag agtggcatta     1920
aaattcctat gttgcatttc agaaatacca caagtaaact gagcaattaa cttgttcata     1980
ccgacactac aagttaacta caaaccgaga cccttatatg cagactgata atacagaatg     2040
atacgtatca ctcctaagac taggaacata cagagctttt gagcttttgg tattttcaag     2100
ttatttgaaa aattaaatct ttatactagg gacgaggttc gtgacaaaag aagacaatca     2160
tgagactcac cgtcttgtca tctacaagtt tcaataagct tccaacttga gtaacctagc     2220
catgtgatta gtaactttcg aagcatgatt cagaacgttc tgctctgccg cgtcaaaaag     2280
ggcagctact tgaagttaaa agaaagatca aaaattcctg agcattgttc aaacagctat     2340
aaatcaaaac agaataagaa ataaggccat cacttaccaa ggaaaaacaa aaaagttcga     2400
gagatcaaca atgcacttca gggacgcacc tgaacccttta cattagtgta aaaataaatt     2460
attagattgt tcggttcgag cgttagccat atacaaaatg cggccttcaa agtcattgga     2520
aaagagctgc tttaggacct ctccaaaagc taaattgaca aacaggctac ctcatatctc     2580
catcatcttt gccaacctttt tcagtaacaa aaaacaaaag caatatcgtt tatttgtcca     2640
ttggacgatg aagaaaagat caaacttagt ctaggtgagg ctaatcaata aagtttgttg     2700
atcctactaa ttcgatcct atcctagcct tagcatttac atctaaaggt ctggtttcac     2760
attctaattg tgaaatgatc tagcaagctc tccctagcat aattattcac ctccaaattt     2820
```

```
gtgtacttgg ttcatcgttc actgaatgag aatgagaaag attcaaaatt gagaagtgtg    2880
ttcgaacact tcaactgtcg cactgttgct ttctacagat atacgcataa caaatacatt    2940
agttgcttaa agggcagctt cttttaatgt gtatcagtat agtcaaggac tcagctacga    3000
acaactcaca atagtctttt tcaccacgac ccacaagttc gcacaaaatt ctaaatacct    3060
tgacgaatag taaatatcgg atgttcagcc gtcagcgaaa tgattttgt gctaatacaa     3120 tttctaaggc aattgacaca ggttggaaaa agtgtgggta ttcggctgat attgtggaac    3180
tgtaatcatc gagctaccag ttctggtttg ttacttgttc gtctcattgt cgtggataag    3240
aacaaataat gtaccggttt attcgaccac caatcagcgc gtaaagcacg cagcagacca    3300
agcaagtagc cggatgaagc agctacgtta cccaaccgtt tatcctaccc aagtaggcga    3360
gttcaatttg tctcacgcga gatgcactca gtgctacaag attgaatggg taattagaag    3420
catgttagtt tctacaatga tcgattcata gtatccggcg acaattgatc ttactgaaga    3480
aaggaggcag acacgcttac cgaaaaaagt gcctacctag caatatttga tgatcgtcca    3540
atggacaaat aaacgatatt gcttttgttt tttgttactg aaaaggttgg caaagatgat    3600
ggagatatga ggtagcctgt ttgtcaattt agcttttgga gaggtcctaa agcagctctt    3660
ttccaatgac tttgaaggcc gcattttgta tatggctaac gctcgaaccg aacaatctaa    3720
taatttattt ttacactaat gtaaaggttc aggtgcgtcc ctgaagtgca ttgttgatct    3780
ctcgaacttt tttgttttc cttggtaagt gatggcctta tttcttattc tgttttgatt     3840
tatagctgtt tgaacaatgc tcaggaattt ttgatctttc ttttaacttc aagtagctgc    3900
cctttttgac gcggcagagc agaacgttct gaatcatgct tcgaaagtta ctaatcacat    3960
ggctaggtta ctcaagttgg aagcttattg aaacttgtag atgacaagac ggtgagtctc    4020
atgattgtct tcttttgtca cgaacctcgt ccctagtata aagatttaat ttttcaaata    4080
acttgaaaat accaaaagct caaaagctct gtatgttcct agtcttagga gtgatacgta    4140
tcattctgta ttatcagtct gcatataagg gtctcggttt gtagtaact tgtagtgtcg     4200 gtatgaacaa gttaattgct cagtttactt gtggtatttc tgaaatgcaa cataggaatt    4260
ttaatgccac tcttgtgttc aagttcctga agttatggca gcttcaggtt aacgtctcga    4320
tttgctgcgt caatcaaagt tttctatggc tatcccctat ggatatgcct agctcttcca    4380
tctgtagttt cagttgttgt tgacgttata ggtactatct tctggttcta tccagctcac    4440
ctcaggaagc ttcaggaact atagtcgatt gtctttgggg aaaggaccaa ttttagcttc    4500
cgaatgatcc agcaattatc ctacatgtac tttccgtttc aagaaactaa cgagatttgt    4560
ttattccatc gtattctaga gagcagcctc ttaacgtctt tttgaagtcc tatctacgtg    4620
agcaagctta tggcaatcgg ctcgctttta aatggagcag agtaggcaga tggaggaaac    4680
tgaccccttg ctctaaatgc tcacactagc aaacttatcc tcccctatct actattaatt    4740
gtatggatgc aatgtcatgt catgaagggc acgcctcaaa agaaacaaaa gataattgag    4800
ctatccagaa gtagttgttc tttttaataa acgttttgta tgctctctgc cttatttggt    4860
ttgagctccg taacaatcct aagccgaaaa cttaagcccc cttacgtggt tttggtttca    4920
aagaaacatg gcatatttgc aaacggcaat caagcgtcta ataggtacta ttagatatgg    4980
cttaacattc cccctgctca gacttcactg ctacaaattt agacttcaac tttaaaatta    5040
tcaatcaata agaacattgc ttggtctttg aagactcttg aaaaatatat cacttgaagt    5100
tcattggatt gatttccagt gtttcgatgg tagaccacaa cgacacctag agatgattgt    5160
gtctcttaac cgttttagac tattgattga gagaggctgc cagcctaata gagttcttca    5220
```

-continued

```
aatcgattta ctggtatgct atgttgccag gttccgtgtt ttatgaactt gtaaactcac    5280
tgaaaccttg ttcttattat ctagtaccca ccgggctcca tgcttttgag ttgttgtaca    5340
acgctagctt acttctttac actttcttct ctgtgccctt aacacgatcc cttactttt     5400 gtagcggttt caatttatag agctcaggtc attactggca agttatctga ttcggttatt    5460
acatattact acaagaaaaa aagaaacat gaaattctga ctcgttgact tgtttatcga     5520
acattgccga agctatgcct ctaactatcg ttctcagttt atgacgtatc tctctgtatc    5580
gaaattttcg tggattatgc tttaaaatag attaagagcc acttgaggcg cacctgaaca    5640
tgattgcctc gaaacatatt agctgtacat ccgttttaga tcttctagtt agcctctgag    5700
agtggttcta tcttttgaag aaatagtact tactctacat tatcaatgtc ttttatttcg    5760
cgctgccgtg taagcaagta ttggtcgatc tttaggtcca gtttctacat catactaaaa    5820
gcgcgcgtgg aggttgctta tgaagaaatt ggtttagctt tggaaattgg agcctctcac    5880
cgtaaaccaa aaaatctgtc agtactataa tttctggtgg agaaccacat ctagtgcaac    5940
tggctgttgc tagaagattc cgttggacca atgtggaatc agagggtata caagtacgtg    6000
aatattaaga cattgattga ttcgaacatc agaatctatg tattctaatc ctatattgta    6060
tcaacaataa tattattatt gatcctgtat gtagaaggtt atgagactta aaatcacacg    6120
gtttaagata ccgaaatgct aagcaaaaac gtttcgtcga gagaaacaaa acattgagt    6180 t                                                                    6181
```

<210> SEQ ID NO 4
<211> LENGTH: 6229
<212> TYPE: DNA
<213> ORGANISM: Komagataella pastoris

<400> SEQUENCE: 4

```
aaagcgcatt tcgcgaagtg tcacttgata gatataacct aaaacgtcaa actattaaat      60
cctcataagc gaacccaatc attctggttg acaggcataa tggtgttcca ttcttctttc     120
atagaggctc tattcaatga cgttcacaaa gaagaagcaa gtgccaatta gtccaaatac     180
aaaacgaagt tttgttaaaa cttttcaatag cacggataag tggttacata aattttttggt    240 atttcaaacc tgcggcattt gatctcacat agaacaacta aaggaccacg ctatcttcgg     300
caaccatcgg aaacttagaa tgaggagcat gtttgagtaa atgaaacata ctcaacagtg    360
aacacaatag gatgcattta agattacatg atcattagtg gattacttaa gaacatcttc    420
agcattcact aggaaaatat tttatattca agaagagtt tgtcagccta cgatgactct     480
cattagtgag acgactaaag tcattaataa atttcagtga cttaaaccaa tacgtataca    540
atcaggtcaa aacatattaa tagaaaaagg gtagactcgg tcactcttgc taaaaaccag    600
aaggagtact aaagctcaac atacatagta agtaaattaa gatcaaaatg aaactggcta    660
cttgaataca gagctgggaa aacgcataac gtttataaat gtattaaata tgagatggta    720
gagttctgtt tgattaaaac cgctgaaaat agttgcttac caagtggcta gatctggacg    780
gttaagaaag tagctgctgt tgtacaaaaa tccaaacgtt ggtgatcaga gcaaggacta    840
ttatgctgat gtaatagaat gcaatgcttg tagtcaatat ttgttcatac ctgacataaa    900
agtactttcc aagaaaactg gtcagttaca ataataaga ttagaccggt gagtgactta     960
gcacattcta ggcaaaaatg aactgtggga tgcttgccac taactataat actatactgt   1020
aaaaataact gttcaaaaag gacacttatc ggttcgtaag tagatgacag gaaaataagg   1080
```

-continued

```
ggccatcaaa caatagatat tgaaggctag catattggta gttgttcctg taagattaat     1140
gttttttggg ggagctagtt catcataaaa cagggcaaag gccaggaatc aatcaattca     1200
cattagaact tggttgataa caagggctcc cacaattaat cgtctaagcg attctcagcg     1260
gcttgtaagc attacagcga ggttaaactt tagatgaaag gatcattatt ctttgagcgt     1320
gttaccatta tcagggtagt aggattgaac agaattatgc ttgctaaaca cagatctcaa     1380
tccagcgaat accatgatat gctcaaagag ttaatctacc catgacccaa gctcagtata     1440
cggtgagtat tcggggcgc gcaagtagtt tccttcattc cactacattt cgatacgtgt      1500
taaatctaat tgtattcttg aaaagaaagc ttggacgagg tcatcagagc atcttactac     1560
tacgtgatga tagacacaga gttgggttac ttttttaaaa aagggttgac atctatgttt     1620
gaactcattt cagtcaagta atcatctgag accatacacc tgcatcaact acacattcca     1680
gcaaatatca gcttttccaa acggagaatg tagcaaagtc aacaaaatga aaatcgacga     1740
ccgcaggatg gacacatctg gagctttcca gaatatcaag tatcaagtgg agcggtgaac     1800
gaaaaatcca actaccctat cctcatttaa aactctcaag aaaagtgatc tctcagttcg     1860
gtaatcggaa tattaaaaga tttcaacata aagaaagaa actacctcga aacgaatatg     1920
tacaagcatt gcataacaat tcaagttttc aaactagaaa aaaaattcct atcttgtagt     1980 cccccttaatc acttttgaga aatagaatgg gagcaggcaa cacgaggcat gagttctttg     2040
cttttaacca aaacttacag aagaatcttt acacgtttgg taggcaacaa aactataccg     2100
gagctcagtt tgcaccaggc aaatgctcca aagtatgaa gctacgagaa tcaaatcgtc      2160
agactaatca agataggtct tgcattcttg ataccgatac ttatccatcc ctcatcaatg     2220
ccttcgcctg tctacagcta ttgatcatat tgagaaattt ggtacaaggc ttttaggaac     2280
gtttcacaac tgtcagcagc atgatgtcct ctaaaaactt cttaatccat atataatcag     2340
acaaagcgtg actaatctgt actacctctg tatgtgtggt cattctcttt acgattcgta     2400
aaacactaca gccttctttg caaagctaga atagcacata cctaattgag tccattgcga     2460
cagtaggcac gaaaatcccc tttctatcta acgtcgctct agcgcaacta ccgtctttca     2520
gaagaaaaag aaaatcacag ccaatttatg aaagcaatcc aagcatttca tcataagaat     2580
caggacctca ggaccaaagt tgcatatact ctcgataatc tgcaatttaa gacttacagc     2640
tcattgcttt cttgactatt ttctagacag gtacacccaa ttgttgagaa aaatcgcact     2700
atgggcaaag taactcctgg tacctaactc tgtgtacttc agcaccgaat gtcggatacc     2760
ggttacaaaa atattcttac ccatattcta ctttaactaa atcctagctt ttaaattagc     2820
aatgttcaag cgttgaaaat gcacagcatc tcaggcgcca aaattactac atgtattgct     2880
tgatgctgac aaggccatga tattaaatag agacgacgta attgttcagc aatagtgtta     2940
cctgcattat caatgctcaa gctcgtgaga tgggatgttg tcaccaaatc atttgcatag     3000
gtgccagtac gattcttgag gttacgcctt gtttaatgct ttctgattca tagcacaaaa     3060
acaagaatca ttgccagttg ttgataggta tctaagtcaa atcttgattt tcagcagaat     3120
accaaactta aattcagcca acttacaaga aaacaataat accatgaact ttgaaagctg     3180
atagttttgg atcgtgactg attttgtcaca catttgggcc aacttgagct tctccgagtt     3240
attagcttag aggtcatgat gtataagttg tactttgtta acaatctcgt ttaaggtatt     3300
ttgaaccttc agcagcagat ggctcttgca aaagagctgt ttttaaaccg catgctgggt     3360
actctctggc actacaatga agttgggagt ttcatgactt tcattcagca ttcgagcgaa     3420
tctaagcgca tcatttttc aaatggtata gctttgggaa gtcctatccc taatgaatac      3480
```

```
tttcgtgaaa tagctaaaca aaacgtatat ttagaagact agtatttatt cgttctaatg   3540
ataactgtct tatggcttga aaagattagt ctaaccacag attccattaa cggggcaaac   3600
agcatccagc attaaaaact aagtaagttc tgttgccaca taagctatga tcattttgat   3660
aggaagctta gattgctttc ataaattggc tgtgattttc ttttcttct gaaagacggt    3720 agttgcgcta gagcgacgtt agatagaaag gggattttcg tgcctactgt cgcaatggac   3780
tcaattaggt atgtgctatt ctagctttgc aaagaaggct gtagtgtttt acgaatcgta   3840
aagagaatga ccacacatac agaggtagta cagattagtc acgctttgtc tgattatata   3900
tggattaaga agttttaga ggacatcatg ctgctgacag ttgtgaaacg ttcctaaaag    3960
ccttgtacca aatttctcaa tatgatcaat agctgtagac aggcgaaggc attgatgagg   4020
gatggataag tatcggtatc aagaatgcaa gacctatctt gattagtctg acgatttgat   4080
tctcgtagct tcatactttt ggagcatttg cctggtgcaa actgagctcc ggtatagttt   4140
tgttgcctac caaacgtgta aagattcttc tgtaagtttt ggttaaaagc aaagaactca   4200
tgcctcgtgt tgcctgctcc cattctattt ctcaaaagtg attaagggga ctacaagata   4260 ggaattttt ttctagtttg aaaacttgaa ttgttatgca atgcttgtac atattcgttt    4320
cgaggtagtt tctttctttt atgttgaaat cttttaatat tccgattacc gaactgagag   4380
atcacttttc ttgagagttt taaatgagga tagggtagtt ggattttcg ttcaccgctc    4440 cacttgatac ttgatattct ggaaagctcc agatgtgtcc atcctgcggt cgtcgatttt   4500
cattttgttg actttgctac attctccgtt tggaaaagct gatatttgct ggaatgtgta   4560
gttgatgcag gtgtatggtc tcagatgatt acttgactga aatgagttca acatagatg    4620 tcaacccttt tttaaaaaag taacccaact ctgtgtctat catcacgtag tagtaagatg   4680
ctctgatgac ctcgtccaag cttcttttc aagaatacaa ttagatttaa cacgtatcga    4740
aatgtagtgg aatgaaggaa actacttgcg cgccccgaa tactcaccgt atactgagct    4800
tgggtcatgg gtagattaac tctttgagca tatcatggta ttcgctggat tgagatctgt   4860
gtttagcaag cataattctg ttcaatccta ctaccctgat aatggtaaca cgctcaaaga   4920
ataatgatcc tttcatctaa agtttaacct cgctgtaatg cttacaagcc gctgagaatc   4980
gcttagacga ttaattgtgg gagcccttgt tatcaaccaa gttctaatgt gaattgattg   5040
attcctggcc tttgccctgt tttatgatga actagctccc caaaaaaaca ttaatcttac   5100
aggaacaact accaatatgc tagccttcaa tatctattgt ttgatggccc cttattttcc   5160
tgtcatctac ttacgaaccg ataagtgtcc tttttgaaca gttattttta cagtatagta   5220
ttatagttag tggcaagcat cccacagttc atttttgcct agaatgtgct aagtcactca   5280
ccggtctaat cttattattt gtaactgacc agttttcttg gaaagtactt ttatgtcagg   5340
tatgaacaaa tattgactac aagcattgca ttctattaca tcagcataat agtccttgct   5400
ctgatcacca acgtttggat ttttgtacaa cagcagctac tttcttaacc gtccagatct   5460
agccacttgg taagcaacta ttttcagcgg ttttaatcaa acagaactct accatctcat   5520
atttaataca tttataaacg ttatgcgttt tcccagctct gtattcaagt agccagtttc   5580
attttgatct taatttactt actatgtatg ttgagcttta gtactccttc tggttttag    5640 caagagtgac cgagtctacc ctttttctat taatatgttt tgacctgatt gtatacgtat   5700
tggtttaagt cactgaaatt tattaatgac tttagtcgtc tcactaatga gagtcatcgt   5760
aggctgacaa actcttcttt gaatataaaa tattttccta gtgaatgctg aagatgttct   5820
```

```
taagtaatcc actaatgatc atgtaatctt aaatgcatcc tattgtgttc actgttgagt    5880
atgtttcatt tactcaaaca tgctcctcat tctaagtttc cgatggttgc cgaagatagc    5940
gtggtccttt agttgttcta tgtgagatca atgccgcag gtttgaaata ccaaaaattt     6000
atgtaaccac ttatccgtgc tattgaaagt tttaacaaaa cttcgttttg tatttggact    6060
aattggcact tgcttcttct tgtgaacgt cattgaatag agcctctatg aaagaagaat     6120
ggaacaccat tatgcctgtc aaccagaatg attgggttcg cttatgagga tttaatagtt    6180
tgacgtttta ggttatatct atcaagtgac acttcgcgaa atgcgcttt                6229
```

<210> SEQ ID NO 5
<211> LENGTH: 1535
<212> TYPE: DNA
<213> ORGANISM: Artificial
<220> FEATURE:
<223> OTHER INFORMATION: Zeocin resistance gene

<400> SEQUENCE: 5

```
tgagcaaaag gccagcaaaa ggccaggaac cgtaaaaagg ccgcgttgct ggcgttttc      60 cataggctcc gcccccctga cgagcatcac aaaaatcgac gctcaagtca gaggtggcga    120
aacccgacag gactataaag ataccaggcg tttccccctg gaagctccct cgtgcgctct    180
cctgttccga ccctgccgct taccggatac ctgtccgcct ttctcccttc gggaagcgtg    240
gcgctttctc atagctcacg ctgtaggtat ctcagttcgg tgtaggtcgt tcgctccaag    300
ctgggctgtg tgcacgaacc ccccgttcag cccgaccgct gcgccttatc cggtaactat    360
cgtcttgagt ccaacccggt aagacacgac ttatcgccac tggcagcagc cactggtaac    420
aggattagca gagcgaggta tgtaggcggt gctacagagt tcttgaagtg gtggcctaac    480
tacggctaca ctagaaggac agtatttggt atctgcgctc tgctgaagcc agttaccttc    540
ggaaaaagag ttggtagctc ttgatccggc aaacaaacca ccgctggtag cggtggtttt    600
tttgtttgca agcagcagat tacgcgcaga aaaaaaggat ctcaagaaga tcctttgatc    660
ttttctacgc atgcagatcc cccacacacc atagcttcaa aatgtttcta ctccttttt     720 actcttccag atttttctcgg actccgcgca tcgccgtacc acttcaaaac acccaagcac    780
agcatactaa attttccctc tttcttcctc tagggtgtcg ttaattaccc gtactaaagg    840
tttggaaaag aaaaaagaga ccgcctcgtt tcttttttctt cgtcgaaaaa ggcaataaaa    900
atttttatca cgtttctttt tcttgaaatt ttttttttta gtttttttct ctttcagtga    960
cctccattga tatttaagtt aataaacggt cttcaatttc tcaagtttca gtttcatttt   1020
tcttgttcta ttacaacttt ttttacttct tgttcattag aaagaaagca tagcaatcta   1080
atctaagggg cggtgttgac aattaatcat cggcatagta tatcggcata gtataatacg   1140
acaaggtgag gaactaaacc atggccaagt tgaccagtgc cgttccggtg ctcaccgcgc   1200
gcgacgtcgc cggagcggtc gagttctgga ccgaccggct cgggttctcc cgggacttcg   1260
tggaggacga cttcgccggt gtggtccggg acgacgtgac cctgttcatc agcgcggtcc   1320
aggaccaggt ggtgccggac aacaccctgg cctgggtgtg ggtgcgcggc ctggacgagc   1380
tgtacgccga gtggtcggag gtcgtgtcca cgaacttccg gacgcctcc gggcggcca    1440 tgaccgagat cggcgagcag ccgtgggggc gggagttcgc cctgcgcgac ccggccggca   1500
actgcgtgca cttcgtggcc gaggagcagg actga                              1535
```

<210> SEQ ID NO 6
<211> LENGTH: 44

```
<212> TYPE: DNA
<213> ORGANISM: Artificial
<220> FEATURE:
<223> OTHER INFORMATION: Primer

<400> SEQUENCE: 6
ttaaagcttg cggccgctga gcaaaaggcc agcaaaaggc cagg              44

<210> SEQ ID NO 7
<211> LENGTH: 31
<212> TYPE: DNA
<213> ORGANISM: Artificial
<220> FEATURE:
<223> OTHER INFORMATION: Primer

<400> SEQUENCE: 7
ttagaattct cagtcctgct cctcggccac g                            31

<210> SEQ ID NO 8
<211> LENGTH: 44
<212> TYPE: DNA
<213> ORGANISM: Artificial
<220> FEATURE:
<223> OTHER INFORMATION: Primer

<400> SEQUENCE: 8
ttagcggccg caatgtcaag tacttaactt ttgtctctga aacc              44

<210> SEQ ID NO 9
<211> LENGTH: 44
<212> TYPE: DNA
<213> ORGANISM: Artificial
<220> FEATURE:
<223> OTHER INFORMATION: Primer

<400> SEQUENCE: 9
ttagcggccg cccaatcaaa caaggtgact tgcgcgaagc aatg              44

<210> SEQ ID NO 10
<211> LENGTH: 43
<212> TYPE: DNA
<213> ORGANISM: Artificial
<220> FEATURE:
<223> OTHER INFORMATION: Primer

<400> SEQUENCE: 10
ttagcggccg caactcaatg tttttgtttc tctcgacgaa acg               43

<210> SEQ ID NO 11
<211> LENGTH: 42
<212> TYPE: DNA
<213> ORGANISM: Artificial
<220> FEATURE:
<223> OTHER INFORMATION: Primer

<400> SEQUENCE: 11
ttagcggccg caaagcgcat ttcgcgaagt gtcacttgat ag                42

<210> SEQ ID NO 12
<211> LENGTH: 1370
<212> TYPE: DNA
<213> ORGANISM: Komagataella pastoris

<400> SEQUENCE: 12
atgaaacata ggaatactac catggcacga ccagctatgc gctaattggt gcaaagtaaa   60
```

```
gttagctcat tcagtgacac cataactcca cccattaaag aaatgtgatc ataataagct    120
tgagtttaat acctacaggt tgtcaagtaa aaattatata gtttgtgaaa aacgattcca    180
gaaacagaac tcttcctgaa tccagcaagg ggaaatatac aacggaccat gacctagtac    240
tactcaaaga acactcaatg agaatataaa agtgttcgca ggataccatt cgcaacatct    300
tgcagtatct cgtattcccg cgatggaaaa cgtagcagta atcgacgcct agtagtacta    360
gcactaacat gctgctgaat gatgattgaa catattcctt caataaagaa gaaggaagta    420
caactgtata actagaattg acaaaacttg gaaagactag gtaacgctca gtcagtaggt    480
ccgtttccac tccttctttt gtgaccgact cagactgaaa cagcgcagtt gcgttagatt    540
agccataata cagtggtgag gtctgacacc tactgacgta atagagtgaa ccaagtatgc    600
gtgatcccag gtttagcaaa taaggataca gagccccaca attcgtaacg ataatgacta    660
cgtatataga tgttgtacag atcagtgaga ctttctctaa ttatctatgg attgagaaag    720
ttattaggag ggacacacga cgacggcttt gacctacttc ccaaaagtct ccatcgatgt    780
ctcaatatga ttgatggcaa gtacacaaat gaaggtacta aggtggaatt gataggtatt    840
gctatccaga aagacaagtc gtagctagaa acgtctgacc ctttgaactc acgtagcttc    900
gtacttttgg gagcccttgc ccagtacaaa gtttaagctg agtcccggta tattttgctg    960
tcgagcaacc gtgtaaatat tgttttgtaa gttcggctac gagcaaagag ctcatacctt   1020
gtactgcctg ctaccaagct ttttctgtg gggattcatg aatccggaag aagatgcatc   1080
tattcattgc tggatttgca ggcaaatgat gtacgctttc acaacagaat ccatcaacta   1140
ttagttggaa gattagaagt atatttcaat atagttcagc aaagagctat agtcacatac   1200
ttttttttgc tcgatgtcaa ttcgaggcaa ttagctttag agcaaatttg ttaggttttg   1260
cttcagcttt ctaatgcctc acaacttcat tccttatcac gcagcgaaag aaccggcgac   1320
agtatcaatc acttcaccca tgatggcata gtagtattcc tatgtttcac              1370

<210> SEQ ID NO 13
<211> LENGTH: 1992
<212> TYPE: DNA
<213> ORGANISM: Komagataella pastoris

<400> SEQUENCE: 13
aatgtcaagt acttaacttt tgtctctgaa accaagtttc ctcaaagata aacttgttat     60
tcaagctagt aggtacaaca agtgtaagct gaagccgaaa tcaaatacaa ggcaaaacga    120
tctttgaaat accgtggaaa aagcaaaatc ccctggaag ttacaaacca cttgctaatc    180
tcccaatata gctgtgcata atcaccatct ggctagcaga atttaaatgt acatgtggct    240
gttatactgt ctggattcca tatctactgc atgcacagcg acgatttatc aaaatcatga    300
taaagtttga gttggcatcc aaattatgtt cactacacct tggaatcttt tttcctcatc    360
tggcaggttc ggatagcgta ataattttg atgctttcaa gacagcacaa tcattaactt    420
ccatcatatc acaagaaccc agtagtaata cctccttaag attgttttca atctgagtgt    480
ttatagacct acacgtgcaa atgaaaaagg acgtctcagc tttgtggaac ttgtcacaat    540
ctggcaaaat ctagtagagg tagtaagcct aattcttaat aactgatagt ctcttacttc    600
aatttgataa tttagaacaa ttacattcac caattctgta cgaactggca actaataggg    660
caaaaacaat ccgttttgat ccataaattt gatctggttg atcagataga atttaatggg    720
tagtgattta tcaacaacaa ttaggcctga actgtaaaga aaaacatcaa ataaagtaca    780
ttctcagggt ttttcacctt acttccaatg accatgcttt tcccgatggg cagatacatc    840
```

```
ttcagctaat tggagtatgg aagtcaatat acgtgaagtc ccctctagaa gcaattttcg      900
gtgcttgcag cacgttatca tgttttcaga gccttgacca gacagaatct gatccaaggc      960
aaacgaggga acagttaaa gtagaagata ccttacatag tcaactaaat ggtattgata      1020
aattctgatt atgagaacaa aacttcaaaa ctatcggtgt gtatcatcta gttgaggttt      1080
tatatctatg tatgatgcta tgtagaccttt aacttgaatg aagcactctc caataagatt      1140
ggccaaagtt caatacaata cttgccacat gaaacagtct aacttctaga gaagtttgct      1200
ggcccttaga taaggctgat agccactatt tacagatagc cctttgctta tgcttgtggg      1260
taatgaacta gggaggtact ggttggtcga tgaaattccg gcagactttt cattcgtacg      1320
acgggtacca agagaaaaat tatgtgttaa agggagcttc aatgtaggcc cataagttta      1380
ggagcaaaat atggcgaata tacaaaatct ataaacctac tcactgttaa gacaaataca      1440
ggtaaatctt cggatatagg ggggacgcca aacttaagat ctggtctacc aataaaccta      1500
tgcctcaaac caaactcata ctcttgatga aatactgatt gattgagtga aagttaaca      1560 gcatcggtta gtcaatcgaa aagttcaatc aatgaacagt ggtagtcctt ctacggtact      1620
taaattccaa tcccaaaata atatcaataa tgaacaggaa tcctccaaga gaatctttct      1680
accatgagaa ttgggaaaaa cagtatccat tcaagaacta gatctacgta ccagaacgcc      1740
aggtttctac gcttaatcac tctatcaaat acaactcaag ctctaagttc ttgcgggttc      1800
agcttacgtt tacgcacaaa acaactactg ccccgaaacc agtaaaaata cattacaaat      1860
gctacgaata agatgatcat agtagccaca ataattcgac ctgatagctc taaaacacgt      1920
ctttaggttg atctgacaat agtatgaacc gataatgaac actataacgg attgctaata      1980
acgaacccag aa                                                         1992
```

<210> SEQ ID NO 14
<211> LENGTH: 1992
<212> TYPE: DNA
<213> ORGANISM: Komagataella pastoris

<400> SEQUENCE: 14

```
ttctgggttc gttattagca atccgttata gtgttcatta tcggttcata ctattgtcag      60
atcaacctaa agacgtgttt tagagctatc aggtcgaatt attgtggcta ctatgatcat      120
cttattcgta gcatttgtaa tgtatttta ctggtttcgg ggcagtagtt gttttgtgcg      180
taaacgtaag ctgaacccgc aagaacttag agcttgagtt gtatttgata gagtgattaa      240
gcgtagaaac ctggcgttct ggtacgtaga tctagttctt gaatggatac tgttttccc      300 aattctcatg gtagaaagat tctcttggag gattcctgtt cattattgat attatttgg      360 gattggaatt taagtaccgt agaaggacta ccactgttca ttgattgaac ttttcgattg      420
actaaccgat gctgttaact tctcactcaa tcaatcagta tttcatcaag agtatgagtt      480
tggtttgagg cataggttta ttggtagacc agatcttaag tttggcgtcc ccctatatc      540 cgaagattta cctgtatttg tcttaacagt gagtaggttt atagatttg tatattcgcc      600 atattttgct cctaaactta tgggcctaca ttgaagctcc cttaacaca taatttttct      660 cttggtaccc gtcgtacgaa tgaaaagtct gccggaattt catcgaccaa ccagtaccte      720 cctagttcat tacccacaag cataagcaaa gggctatctg taaatagtgg ctatcagcct      780
tatctaaggg ccagcaaact tctctagaag ttagactgtt tcatgtggca agtattgtat      840
tgaactttgg ccaatcttat tggagagtgc ttcattcaag ttaaggtcta catagcatca      900
```

```
tacatagata taaaacctca actagatgat acacaccgat agttttgaag tttttgttctc   960
ataatcagaa tttatcaata ccatttagtt gactatgtaa ggtatcttct actttaactg  1020
tttccctcgt ttgccttgga tcagattctg tctggtcaag gctctgaaaa catgataacg  1080
tgctgcaagc accgaaaatt gcttctagag gggacttcac gtatattgac ttccatactc  1140
caattagctg aagatgtatc tgcccatcgg gaaaagcatg gtcattggaa gtaaggtgaa  1200
aaaccctgag aatgtacttt atttgatgtt tttctttaca gttcaggcct aattgttgtt  1260
gataaatcac tacccattaa attctatctg atcaaccaga tcaaatttat ggatcaaaac  1320
ggattgtttt tgccctatta gttgccagtt cgtacagaat tggtgaatgt aattgttcta  1380
aattatcaaa ttgaagtaag agactatcag ttattaagaa ttaggcttac tacctctact  1440
agattttgcc agattgtgac aagttccaca aagctgagac gtccttttc atttgcacgt   1500
gtaggtctat aaacactcag attgaaaaca atcttaagga ggtattacta ctgggttctt  1560
gtgatatgat ggaagttaat gattgtgctg tcttgaaagc atcaaaaatt attacgctat  1620
ccgaacctgc cagatgagga aaaaagattc caaggtgtag tgaacataat ttggatgcca  1680
actcaaactt tatcatgatt ttgataaatc gtcgctgtgc atgcagtaga tatggaatcc  1740
agacagtata acagccacat gtacatttaa attctgctag ccagatggtg attatgcaca  1800
gctatattgg gagattagca agtggtttgt aacttccagg gggattttgc ttttccacg   1860
gtatttcaaa gatcgttttg ccttgtattt gatttcggct tcagcttaca cttgttgtac  1920
ctactagctt gaataacaag tttatctttg aggaaacttg gtttcagaga caaaagttaa  1980
gtacttgaca tt                                                     1992

<210> SEQ ID NO 15
<211> LENGTH: 1257
<212> TYPE: DNA
<213> ORGANISM: Komagataella pastoris

<400> SEQUENCE: 15
aaaattagta tcagttggcc atgcgaccaa gcctgttgga acgcaaaagc atatccgaat    60
tatggttgga aattaccttc gaccttcaaa cactaaactc ttcacagggc tattattcca   120
gctattgcag aacttcatac gaatttgggc ttgctaaaaa ttggcaggat cgttcttcaa   180
taactgaata cagtattgta cctattcaag cagttagtcc atacttaggg ccttcctagc   240
ctgtccagtc taccattaac gaaagttctg agctgtgtct atccaaatta atttgtgtca   300
gaacctacgt aaccactata agtctcataa cgttttttgaa atagataaaa ttagtttgtt   360
tgatcattca agcacattat agataatatt ccaaaaagaa agtttcaagg tgcccctttgg  420
acatataaaa ctttgccacg gtgctaaact taaaagaatg atcttccaaa aatacggaat   480
agaataatct attttttagaa gagaagacta aaaatcgagc gatactatga atgtctgtta   540
caaactgaat ttttgcacgt aacgaatact ttgaaacaat cctcaaaatc ttgttttggt   600
gtttgtcgag tagtctttac caggccgaat cctgtagtta aaaataattt tctatttgga   660
caactaaggg tatcccctca gtttggcctt ttgtgtacct tgttcggaaa ggctccgttc   720
tgcaattctg cagcaacctt gtcattagct gtgtaatgct cgctggtgag tagcataagt   780
cattccaatg gtaactacca agcttgtaat ataaccacca gcacctccat tcagtagtag   840
caatgagcaa ggtcggagat tgcttttaag cgaggtttca agtaatcttt gtagttttgc   900
tttgtcgaaa aatggccacg gcttacacat acagttcgtc caccagatct ttaggcttca   960
tcaacaaagt tttcgacttc gttgtctata ggttttattc tttatcagcg tcagactatg  1020
```

| | |
|---|---|
| atcgtactag tttgagctga agcccatcag gatgtttacc actccagttt tgtaatttcc | 1080 |
| gcggctatct agggctacgt tgtccattgc cgagtttata tatgacatca cattaggcag | 1140 |
| taattctcca tgcttctttt tcgataatgt tttggtctag gttcgtgcat gaaattttt | 1200 |
| cttcatccag actatctctg cgctgcactg ttcacatagc caactgatac tgatttc | 1257 |

```
<210> SEQ ID NO 16
<211> LENGTH: 2699
<212> TYPE: DNA
<213> ORGANISM: Komagataella pastoris

<400> SEQUENCE: 16
```

| | |
|---|---|
| ccaatcaaac aaggtgactt gcgcgaagca atgatttgtg gatgggctgc ggtatggcag | 60 |
| cataacaatg caacgctatt tcagaaattg taaagtgtaa aggaaatatt caaccctata | 120 |
| aagaatctac cgaaacgtag gataaataat ttccacagag tacactttg gtttttatgg | 180 |
| acggcgttga gttgcacaga tgatggaata ttgtgataaa atacgctata aattttgga | 240 |
| gaccctaaga tcaagtggac taggtcgatt gcgtatatta gggtattaaa gacttactta | 300 |
| attctataag agctcggcaa gctatattct cagttccttc gcagtcgacc ttcagtgccc | 360 |
| aaaactttaa agtggacggg tgttttctaa agattgctat tgttcaattg cccggttttt | 420 |
| taaccgctga aaaccagtgg caagagtgga ctacgtgcgc attgcaattt gtataatcca | 480 |
| tataattttg ttccacggcc ttaagttatt gtactgtttg ctcaattttg aagcggaata | 540 |
| tccgtcctag tctcgaatcc ttatttaagt accggtatca tttgcatatc ctctcagccc | 600 |
| tcaaacgccc attctttata gtaatggtta tgtattaatc gactacgatg attgactcag | 660 |
| ggaggcacga atagtataat ttgtaacttg cagtgggaag ctaatttcgg gtgtcttgaa | 720 |
| agacgaggtt aaaaatttga acccaaaccg attttaccgg agatcctacc tcaaattaga | 780 |
| acaactttaa agcttttcaag gaattgaaat tccatctttta tagaccggta attctttgaa | 840 |
| gagtaatcaa tgtaagagca agttctaaag agaggatcca aattccttct gatagcaatt | 900 |
| gtaaggagct gcaaagttca acataatatt tgcgatagta accgtcctac ggatacttaa | 960 |
| atcggtatca aagagtgacc aatcctgaat cagtgtagtg caaaaagaaa taacgatgat | 1020 |
| aaacgaatca agattctgat gagttgtcca agacggggct atcataatat ttaaaaaata | 1080 |
| gaacctacta atttaacaag gtaaatctca tagatttaag tttcacgact agcttagcta | 1140 |
| ccactcaaat aagctcccgc ttgttcattc ggctggggtc tccaatctcc atctccaatg | 1200 |
| gatatttttt ttttaagtgg agagagatgt tcagtaaact gtgagttcag ttgtcagaag | 1260 |
| caaccaatat ttaccatgga gacgaataag cagatattat atactctatt tttacagccc | 1320 |
| ttttgtataa tcctcaggga tggttggcgc ttccctgtgt tccaagtaac cacactcttc | 1380 |
| aagttggaaa tgcaaaaggt cccaatgcat gctcccaagt catactgaat acagagatag | 1440 |
| attctttgaa ttggatcgat ctctaatgaa attcatggat gagaagagag tgttaaaaac | 1500 |
| tttgccccaa ctaaatactt tatctgaatg aatcattaaa gaacacgaca agttcagtat | 1560 |
| gttgcttgga gcctccgatt cacagtcttg taagtagtgc gtgttttcaa atatttgcat | 1620 |
| tagcaatccc tccaagtagc ccacataggg accaaaaaaa tagtatagtt tgttttgggg | 1680 |
| ggaagggagt aggaattgct ttcgaaatgg ttaactcctg cttagtttca tttaaaaaat | 1740 |
| gaatagagaa gtagatacag aatactttgt aagactgctt acatgaatga tgccagagag | 1800 |
| tgtgccgaaa gatctacatg ctactaaatt tactatcaat agggataaaa tgtattaggc | 1860 |

```
tacctactat gccgtattgg aaaggcgaag tgctttgtat gcaagggatt ggggcatagg   1920
caaacggatc tatgacaaga gatacgaaat tacttctgtt acccactctg ctcctaccaa   1980
accaaatata tctgtgacca aaatatcat ttgtcttgtg ctccacatag cggccaggct    2040
caaagagaac actagatctg ctttcagaca ttaccgcgtg caaatatgac aagtcactag   2100
gtgatgaact agtcgataaa accaaaaacg atctgatcaa taacttgaca acatcgttct   2160
tatcggattt ctagctcttg aatagtcaaa tgctgagttc aattttaaag tgaatatttt   2220
tcaccgaagt cgatttttagc ccattagtca acaacagaa gagaaaagac aaaccttctt   2280
tttcatgaca catgaaacaa atcacaaaaa ttgagtcata ttacggtttc aatttctgct   2340
gtttgtataa gtcattggct ggcaaacaca tctcctggcc tcatactgaa aatatatgaa   2400
gataactgct tctaccaatt tcaattgatc aaggttctac ccatacgtat agttccagag   2460
catgatgtta gggaaactta cagggatgat gtgggccaca gcataatatc aacaataccT   2520
aacaatcggt atttaattca tagatattca ataccaattc tccacgatga aaggggcga   2580 ctcctcttct tggacgttct gaaaatacag gtacgctcac gtcagtgcct gagcacatac   2640
agcgacgtta gtatcaatct tcctgggaca tctctaatgc tctaaaatga agaaaaagt    2699
```

<210> SEQ ID NO 17
<211> LENGTH: 2699
<212> TYPE: DNA
<213> ORGANISM: Komagataella pastoris

<400> SEQUENCE: 17

```
acttttctt cattttagag cattagagat gtcccaggaa gattgatact aacgtcgctg     60
tatgtgctca ggcactgacg tgagcgtacc tgtattttca gaacgtccaa gaagaggagt   120
cgccccttct catcgtggag aattggtatt gaatatctat gaattaaata ccgattgtta   180
ggtattgttg atattatgct gtggcccaca tcatccctgt aagtttccct aacatcatgc   240
tctggaacta tacgtatggg tagaaccttg atcaattgaa attggtagaa gcagttatct   300
tcatatattt tcagtatgag gccaggagat gtgtttgcca gccaatgact tatacaaaca   360
gcagaaattg aaaccgtaat atgactcaat ttttgtgatt tgtttcatgt gtcatgaaaa   420
agaaggtttg tcttttctct tctgttgttt gactaatggg ctaaaatcga cttcggtgaa   480
aaatattcac tttaaaattg aactcagcat ttgactattc aagagctaga atccgataa    540 gaacgatgtt gtcaagttat tgatcagatc gttttttggtt ttatcgacta gttcatcacc   600
tagtgacttg tcatatttgc acgcggtaat gtctgaaagc agatctagtg ttctctttga   660
gcctggccgc tatgtggagc acaagacaaa tgatattttt ggtcacagat atatttggtt   720
tggtaggagc agagtgggta acagaagtaa tttcgtatct cttgtcatag atccgtttgc   780
ctatgcccca atcccttgca tacaaagcac ttcgcctttc caatacggca tagtaggtag   840
cctaatacat tttatcccta ttgatagtaa atttagtagc atgtagatct ttcggcacac   900
tctctggcat cattcatgta agcagtctta caaagtattc tgtatctact ctctcattca   960 tttttttaaat gaaactaagc aggagttaac catttcgaaa gcaattccta ctcccttccc  1020
cccaaaacaa actatactat tttttggtc cctatgtggg ctacttggag ggattgctaa  1080
tgcaaatatt tgaaaacacg cactacttac aagactgtga atcggaggct ccaagcaaca  1140
tactgaactt gtcgtgttct ttaatgattc attcagataa agtatttagt tggggcaaag  1200
tttttaacac tctcttctca tccatgaatt tcattagaga tcgatccaat tcaaagaatc  1260
tatctctgta ttcagtatga cttgggagca tgcattggga ccttttgcat ttccaacttg  1320
```

```
aagagtgtgg ttacttggaa cacagggaag cgccaaccat ccctgaggat tatacaaaag    1380
ggctgtaaaa atagagtata taatatctgc ttattcgtct ccatggtaaa tattggttgc    1440
ttctgacaac tgaactcaca gtttactgaa catctctctc cacttaaaaa aaaatatcc     1500 attggagatg gagattggag accccagccg aatgaacaag cgggagctta tttgagtggt    1560
agctaagcta gtcgtgaaac ttaaatctat gagatttacc ttgttaaatt agtaggttct    1620 atttttaaa tattatgata gccccgtctt ggacaactca tcagaatctt gattcgttta     1680
tcatcgttat ttcttttttgc actacactga ttcaggattg gtcactcttt gataccgatt   1740
taagtatccg taggacggtt actatcgcaa atattatgtt gaactttgca gctccttaca    1800
attgctatca gaaggaattt ggatcctctc tttagaactt gctcttacat tgattactct    1860
tcaaagaatt accggtctat aaagatggaa tttcaattcc ttgaaagctt taagttgtt     1920 ctaatttgag gtaggatctc cggtaaaatc ggtttgggtt caaatttta acctcgtctt     1980 tcaagacacc cgaaattagc ttcccactgc aagttacaaa ttatactatt cgtgcctccc    2040
tgagtcaatc atcgtagtcg attaatacat aaccattact ataagaatg ggcgtttgag     2100 ggctgagagg atatgcaaat gataccggta cttaaataag gattcgagac taggacggat    2160
attccgcttc aaaattgagc aaacagtaca ataacttaag gccgtggaac aaaattatat    2220
ggattataca aattgcaatg cgcacgtagt ccactcttgc cactggtttt cagcggttaa    2280
aaaaccgggc aattgaacaa tagcaatctt tagaaaacac ccgtccactt taaagttttg    2340
ggcactgaag gtcgactgcg aaggaactga gaatatagct tgccgagctc ttatagaatt    2400
aagtaagtct ttaacaccct aatatacgca atcgacctag tccacttgat cttagggtct    2460
ccaaaattat atagcgtatt ttatcacaat attccatcat ctgtgcaact caacgccgtc    2520
cataaaaacc aaaagtgtac tctgtggaaa ttatttatcc tacgtttcgg tagattcttt    2580
atagggttga atatttcctt tacactttac aatttctgaa atagcgttgc attgttatgc    2640
tgccataccg cagcccatcc acaaatcatt gcttcgcgca agtcaccttg tttgattgg     2699
```

<210> SEQ ID NO 18
<211> LENGTH: 883
<212> TYPE: DNA
<213> ORGANISM: Komagataella pastoris

<400> SEQUENCE: 18

```
gaagaaaaga tcaaacttag tctaggtgag gctaatcaat aaagtttgtt gatcctacta     60
attacgatcc tatcctagcc ttagcattta catctaaagg tctggtttca cattctaatt    120
gtgaaatgat ctagcaagct ctccctagca taattattca cctccaaatt tgtgtacttg    180
gttcatcgtt cactgaatga gaatgagaaa gattcaaaat tgagaagtgt gttcgaacac    240
ttcaactgtc gcactgttgc tttctacaga tatacgcata acaaatacat tagttgctta    300
aagggcagct tcttttaatg tgtatcagta tagtcaagga ctcagctacg aacaactcac    360
aatagtcttt ttcaccacga cccacaagtt cgcacaaaat tctaaatacc ttgacgaata    420
gtaaatatcg gatgttcagc cgtcagcgaa atgattttg tgctaataca atttctaagg     480
caattgacac aggttggaaa aagtgtgggt attcggctga tattgtggaa ctgtaatcat    540
cgagctacca gttctggttt gttacttgtt cgtctcattg tcgtggataa gaacaaataa    600
tgtaccggtt tattcgacca ccaatcagcg cgtaaagcac gcagcagacc aagcaagtag    660
ccggatgaag cagctacgtt acccaaccgt ttatcctacc caagtaggcg agttcaattt    720
```

| | |
|---|---|
| gtctcacgcg agatgcactc agtgctacaa gattgaatgg gtaattagaa gcatgttagt | 780 |
| ttctacaatg atcgattcat agtatccggc gacaattgat cttactgaag aaaggaggca | 840 |
| gacacgctta ccgaaaaaag tgcctaccta gcaatatttg atg | 883 |

<210> SEQ ID NO 19
<211> LENGTH: 2649
<212> TYPE: DNA
<213> ORGANISM: Komagataella pastoris

<400> SEQUENCE: 19

| | |
|---|---|
| aactcaatgt ttttgtttct ctcgacgaaa cgttttgct tagcatttcg gtatcttaaa | 60 |
| ccgtgtgatt ttaagtctca taaccttta catacaggat caataataat attattgttg | 120 |
| atacaatata ggattagaat acatagattc tgatgttcga atcaatcaat gtcttaatat | 180 |
| tcacgtactt gtataccctc tgattccaca ttggtccaac ggaatcttct agcaacagcc | 240 |
| agttgcacta gatgtggttc tccaccagaa attatagtac tgacagattt tttggtttac | 300 |
| ggtgagaggc tccaatttcc aaagctaaac caatttcttc ataagcaacc tccacgcgcg | 360 |
| cttttagtat gatgtagaaa ctggacctaa agatcgacca atacttgctt acacggcagc | 420 |
| gcgaaataaa agacattgat aatgtagagt aagtactatt tcttcaaaag atagaaccac | 480 |
| tctcagaggc taactagaag atctaaaacg gatgtacagc taatatgttt cgaggcaatc | 540 |
| atgttcaggt gcgcctcaag tggctcttaa tctattttaa agcataatcc acgaaaattt | 600 |
| cgatacagag agatacgtca taaactgaga acgatagtta gaggcatagc ttcggcaatg | 660 |
| ttcgataaac aagtcaacga gtcagaattt catgtttctt ttttttcttg tagtaatatg | 720 |
| taataaccga atcagataac ttgccagtaa tgacctgagc tctataaatt gaaaccgcta | 780 |
| caaaaagtaa gggatcgtgt taagggcaca gagaagaaag tgtaaagaag taagctagcg | 840 |
| ttgtacaaca actcaaaagc atggagcccg gtgggtacta gataataaga acaaggtttc | 900 |
| agtgagttta caagttcata aaacacggaa cctggcaaca tagcatacca gtaaatcgat | 960 |
| ttgaagaact ctattaggct ggcagcctct ctcaatcaat agtctaaaac ggttaagaga | 1020 |
| cacaatcatc tctaggtgtc gttgtggtct accatcgaaa cactggaaat caatccaatg | 1080 |
| aacttcaagt gatatatttt tcaagagtct tcaaagacca agcaatgttc ttattgattg | 1140 |
| ataatttta agttgaagtc taaatttgta gcagtgaagt ctgagcaggg ggaatgttaa | 1200 |
| gccatatcta atagtaccta ttagacgctt gattgccgtt tgcaaatatg ccatgtttct | 1260 |
| ttgaaaccaa aaccacgtaa ggggcttaa gttttcggct taggattgtt acggagctca | 1320 |
| aaccaaataa ggcagagagc atacaaaacg tttattaaaa agaacaacta cttctggata | 1380 |
| gctcaattat cttttgtttc ttttgaggcg tgcccttcat gacatgacat tgcatccata | 1440 |
| caattaatag tagatagggg aggataagtt tgctagtgtg agcatttaga gcaagggtc | 1500 |
| agtttcctcc atctgcctac tctgctccat ttaaaagcga gccgattgcc ataagcttgc | 1560 |
| tcacgtagat aggacttcaa aaagacgtta agaggctgct ctctagaata cgatggaata | 1620 |
| aacaaatctc gttagtttct tgaaacggaa agtacatgta ggataattgc tggatcattc | 1680 |
| ggaagctaaa attggtcctt tccccaaaga caatcgacta tagttcctga agcttcctga | 1740 |
| ggtgagctgg atagaaccag aagatagtac ctataacgtc aacaacaact gaaactacag | 1800 |
| atggaagagc taggcatatc catagggat agccatagaa aactttgatt gacgcagcaa | 1860 |
| atcgagacgt taacctgaag ctgccataac ttcaggaact tgaacacaag agtggcatta | 1920 |
| aaattcctat gttgcatttc agaaatacca caagtaaact gagcaattaa cttgttcata | 1980 |

```
ccgacactac aagttaacta caaaccgaga cccttatatg cagactgata atacagaatg    2040
atacgtatca ctcctaagac taggaacata cagagctttt gagcttttgg tattttcaag    2100
ttatttgaaa aattaaatct ttatactagg gacgaggttc gtgacaaaag aagacaatca    2160
tgagactcac cgtcttgtca tctacaagtt tcaataagct tccaacttga gtaacctagc    2220
catgtgatta gtaactttcg aagcatgatt cagaacgttc tgctctgccg cgtcaaaaag    2280
ggcagctact tgaagttaaa agaaagatca aaaattcctg agcattgttc aaacagctat    2340
aaatcaaaac agaataagaa ataaggccat cacttaccaa ggaaaaacaa aaagttcga    2400 gagatcaaca atgcacttca gggacgcacc tgaacctta cattagtgta aaaataaatt    2460
attagattgt tcggttcgag cgttagccat atacaaaatg cggccttcaa agtcattgga    2520
aaagagctgc tttaggacct ctccaaaagc taaattgaca acaggctac ctcatatctc    2580 catcatcttt gccaaccttt tcagtaacaa aaaacaaaag caatatcgtt tatttgtcca    2640
ttggacgat                                                            2649

<210> SEQ ID NO 20
<211> LENGTH: 2649
<212> TYPE: DNA
<213> ORGANISM: Komagataella pastoris

<400> SEQUENCE: 20
atcgtccaat ggacaaataa acgatattgc ttttgttttt tgttactgaa aaggttggca      60
aagatgatgg agatatgagg tagcctgttt gtcaatttag cttttggaga ggtcctaaag     120
cagctctttt ccaatgactt tgaaggccgc attttgtata tggctaacgc tcgaaccgaa     180
caatctaata atttattttt acactaatgt aaaggttcag gtgcgtccct gaagtgcatt     240
gttgatctct cgaactttt tgttttcct tggtaagtga tggccttatt tcttattctg      300
ttttgattta tagctgtttg aacaatgctc aggaattttt gatctttctt ttaacttcaa     360
gtagctgccc ttttgacgc ggcagagcag aacgttctga atcatgcttc gaaagttact     420
aatcacatgg ctaggttact caagttggaa gcttattgaa acttgtagat gacaagacgg     480
tgagtctcat gattgtcttc ttttgtcacg aacctcgtcc ctagtataaa gatttaattt     540
ttcaaataac ttgaaaatac caaaagctca aaagctctgt atgttcctag tcttaggagt     600
gatacgtatc attctgtatt atcagtctgc atataagggt ctcggtttgt agttaacttg     660
tagtgtcggt atgaacaagt taattgctca gtttacttgt ggtatttctg aaatgcaaca     720
taggaatttt aatgccactc ttgtgttcaa gttcctgaag ttatggcagc ttcaggttaa     780
cgtctcgatt tgctgcgtca atcaaagttt tctatggcta tccctatgg atatgcctag     840 ctcttccatc tgtagtttca gttgttgttg acgttatagg tactatcttc tggttctatc     900
cagctcacct caggaagctt caggaactat agtcgattgt ctttgggaa aggaccaatt     960 ttagcttccg aatgatccag caattatcct acatgtactt tccgtttcaa gaaactaacg    1020
agatttgttt attccatcgt attctagaga gcagcctctt aacgtctttt tgaagtccta    1080
tctacgtgag caagcttatg gcaatcggct cgcttttaaa tggagcagag taggcagatg    1140
gaggaaactg accccttgct ctaaatgctc acactagcaa acttatcctc ccctatctac    1200
tattaattgt atggatgcaa tgtcatgtca tgaagggcac gcctcaaaag aaacaaaaga    1260
taattgagct atccagaagt agttgttctt tttaataaac gttttgtatg ctctctgcct    1320
tatttggttt gagctccgta acaatcctaa gccgaaaact taagcccct tacgtggttt    1380
```

```
tggtttcaaa gaaacatggc atatttgcaa acggcaatca agcgtctaat aggtactatt    1440
agatatggct taacattccc cctgctcaga cttcactgct acaaatttag acttcaactt    1500
taaaattatc aatcaataag aacattgctt ggtctttgaa gactcttgaa aaatatatca    1560
cttgaagttc attggattga tttccagtgt ttcgatggta gaccacaacg acacctagag    1620
atgattgtgt ctcttaaccg ttttagacta ttgattgaga gaggctgcca gcctaataga    1680
gttcttcaaa tcgatttact ggtatgctat gttgccaggt tccgtgtttt atgaacttgt    1740
aaactcactg aaaccttgtt cttattatct agtacccacc gggctccatg cttttgagtt    1800
gttgtacaac gctagcttac ttctttacac tttcttctct gtgcccttaa cacgatccct    1860
tacttttgt agcggtttca atttatagag ctcaggtcat tactggcaag ttatctgatt    1920
cggttattac atattactac aagaaaaaaa agaaacatga aattctgact cgttgacttg    1980
tttatcgaac attgccgaag ctatgcctct aactatcgtt ctcagtttat gacgtatctc    2040
tctgtatcga aattttcgtg gattatgctt taaaatagat taagagccac ttgaggcgca    2100
cctgaacatg attgcctcga aacatattag ctgtacatcc gttttagatc ttctagttag    2160
cctctgagag tggttctatc ttttgaagaa atagtactta ctctacatta tcaatgtctt    2220
ttatttcgcg ctgccgtgta agcaagtatt ggtcgatctt taggtccagt ttctacatca    2280
tactaaaagc gcgcgtggag gttgcttatg aagaaattgg tttagctttg gaaattggag    2340
cctctcaccg taaccaaaaa aatctgtcag tactataatt tctggtggag aaccacatct    2400
agtgcaactg gctgttgcta gaagattccg ttggaccaat gtggaatcag agggtataca    2460
agtacgtgaa tattaagaca ttgattgatt cgaacatcag aatctatgta ttctaatcct    2520
atattgtatc aacaataata ttattattga tcctgtatgt agaaggttat gagacttaaa    2580
atcacacggt ttaagatacc gaaatgctaa gcaaaaacgt ttcgtcgaga gaaacaaaaa    2640
cattgagtt                                                            2649
```

```
<210> SEQ ID NO 21
<211> LENGTH: 1111
<212> TYPE: DNA
<213> ORGANISM: Komagataella pastoris

<400> SEQUENCE: 21
caagcatttc atcataagaa tcaggacctc aggaccaaag ttgcatatac tctcgataat      60
ctgcaattta agacttacag ctcattgctt tcttgactat tttctagaca ggtacaccca     120
attgttgaga aaaatcgcac tatgggcaaa gtaactcctg gtacctaact ctgtgtactt     180
cagcaccgaa tgtcggatac cggtttacaa atattcttaa cccatattct actttaacta     240
aatcctagct tttaaattag caatgttcaa gcgttgaaaa tgcacagcat ctcaggcgcc     300
aaaattacta catgtattgc ttgatgctga caaggccatg atattaaata gagacgacgt     360
aattgttcag caatagtgtt acctgcatta tcaatgctca agctcgtgag atgggatgtt     420
gtcaccaaat catttgcata ggtgccagta cgattcttga ggttacgcct tgtttaatgc     480
tttctgattc atagcacaaa aacaagaatc attgccagtt gttgataggt atctaagtca     540
aatcttgatt ttcagcagaa taccaaactt aaattcagcc aacttacaag aaaacaataa     600
taccatgaac tttgaaagct gatagttttg gatcgtgact gatttgtcac acatttgggc     660
caacttgagc ttctccgagt tattagctta gaggtcatga tgtataagtt gtactttgtt     720
aacaatctcg tttaaggtat tttgaacctt cagcagcaga tggctcttgc aaaagagctg     780
tttttaaacc gcatgctggg tactctctgg cactacaatg aagttgggag tttcatgact     840
```

-continued

| | |
|---|---|
| ttcattcagc attcgagcga atctaagcgc atcattttt caaatggtat agctttggga | 900 |
| agtcctatcc ctaatgaata ctttcgtgaa atagctaaac aaaacgtata tttagaagac | 960 |
| tagtatttat tcgttctaat gataactgtc ttatggcttg aaaagattag tctaaccaca | 1020 |
| gattccatta acggggcaaa cagcatccag cattaaaaac taagtaagtt ctgttgccac | 1080 |
| ataagctatg atcatttga taggaagctt a | 1111 |

<210> SEQ ID NO 22
<211> LENGTH: 2559
<212> TYPE: DNA
<213> ORGANISM: Komagataella pastoris

<400> SEQUENCE: 22

| | |
|---|---|
| aaagcgcatt tcgcgaagtg tcacttgata gatataacct aaaacgtcaa actattaaat | 60 |
| cctcataagc gaacccaatc attctggttg acaggcataa tggtgttcca ttcttctttc | 120 |
| atagaggctc tattcaatga cgttcacaaa gaagaagcaa gtgccaatta gtccaaatac | 180 |
| aaaacgaagt tttgttaaaa ctttcaatag cacggataag tggttacata aattttggt | 240 |
| atttcaaacc tgcggcattt gatctcacat agaacaacta aaggaccacg ctatcttcgg | 300 |
| caaccatcgg aaacttagaa tgaggagcat gtttgagtaa atgaaacata ctcaacagtg | 360 |
| aacacaatag gatgcattta agattacatg atcattagtg gattacttaa gaacatcttc | 420 |
| agcattcact aggaaaatat tttatattca agaagagtt tgtcagccta cgatgactct | 480 |
| cattagtgag acgactaaag tcattaataa atttcagtga cttaaaccaa tacgtataca | 540 |
| atcaggtcaa acatattaa tagaaaaagg gtagactcgg tcactcttgc taaaaaccag | 600 |
| aaggagtact aaagctcaac atacatagta agtaaattaa gatcaaaatg aaactggcta | 660 |
| cttgaataca gagctgggaa aacgcataac gtttataaat gtattaaata tgagatggta | 720 |
| gagttctgtt tgattaaaac cgctgaaaat agttgcttac caagtggcta gatctggacg | 780 |
| gttaagaaag tagctgctgt tgtacaaaaa tccaaacgtt ggtgatcaga gcaaggacta | 840 |
| ttatgctgat gtaatagaat gcaatgcttg tagtcaatat ttgttcatac ctgacataaa | 900 |
| agtactttcc aagaaaactg gtcagttaca aataataaga ttagaccggt gagtgactta | 960 |
| gcacattcta ggcaaaaatg aactgtggga tgcttgccac taactataat actatactgt | 1020 |
| aaaaataact gttcaaaaag gacacttatc ggttcgtaag tagatgacag gaaaataagg | 1080 |
| ggccatcaaa caatagatat tgaaggctag catattggta gttgttcctg taagattaat | 1140 |
| gtttttttgg ggagctagtt catcataaaa cagggcaaag gccaggaatc aatcaattca | 1200 |
| cattagaact tggttgataa caagggctcc cacaattaat cgtctaagcg attctcagcg | 1260 |
| gcttgtaagc attacagcga ggttaaactt tagatgaaag gatcattatt ctttgagcgt | 1320 |
| gttaccatta tcagggtagt aggattgaac agaattatgc ttgctaaaca cagatctcaa | 1380 |
| tccagcgaat accatgatat gctcaaagag ttaatctacc catgacccaa gctcagtata | 1440 |
| cggtgagtat tcggggcgc gcaagtagtt tccttcattc cactacattt cgatacgtgt | 1500 |
| taaatctaat tgtattcttg aaagaaaagc ttggacgagg tcatcagagc atcttactac | 1560 |
| tacgtgatga tagacacaga gttgggttac tttttaaaa aagggttgac atctatgttt | 1620 |
| gaactcattt cagtcaagta atcatctgag accatacacc tgcatcaact acacattcca | 1680 |
| gcaaatatca gcttttccaa acggagaatg tagcaaagtc aacaaaatga aaatcgacga | 1740 |
| ccgcaggatg gacacatctg gagctttcca gaatatcaag tatcaagtgg agcggtgaac | 1800 |

| | |
|---|---|
| gaaaaatcca actaccctat cctcatttaa aactctcaag aaaagtgatc tctcagttcg | 1860 |
| gtaatcggaa tattaaaaga tttcaacata aagaaagaa actacctcga aacgaatatg | 1920 |
| tacaagcatt gcataacaat tcaagttttc aaactagaaa aaaaattcct atcttgtagt | 1980 |
| ccccttaatc acttttgaga aatagaatgg gagcaggcaa cacgaggcat gagttctttg | 2040 |
| cttttaacca aaacttacag aagaatcttt acacgtttgg taggcaacaa aactataccg | 2100 |
| gagctcagtt tgcaccaggc aaatgctcca aaagtatgaa gctacgagaa tcaaatcgtc | 2160 |
| agactaatca agataggtct tgcattcttg ataccgatac ttatccatcc ctcatcaatg | 2220 |
| ccttcgcctg tctacagcta ttgatcatat tgagaaattt ggtacaaggc ttttaggaac | 2280 |
| gtttcacaac tgtcagcagc atgatgtcct ctaaaaactt cttaatccat atataatcag | 2340 |
| acaaagcgtg actaatctgt actacctctg tatgtgtggt cattctcttt acgattcgta | 2400 |
| aaacactaca gccttctttg caaagctaga atagcacata cctaattgag tccattgcga | 2460 |
| cagtaggcac gaaaatcccc tttctatcta acgtcgctct agcgcaacta ccgtctttca | 2520 |
| gaagaaaaag aaaatcacag ccaatttatg aaagcaatc | 2559 |

<210> SEQ ID NO 23
<211> LENGTH: 2559
<212> TYPE: DNA
<213> ORGANISM: Komagataella pastoris

<400> SEQUENCE: 23

| | |
|---|---|
| gattgctttc ataaattggc tgtgattttc tttttcttct gaaagacggt agttgcgcta | 60 |
| gagcgacgtt agatagaaag gggatttcg tgcctactgt cgcaatggac tcaattaggt | 120 |
| atgtgctatt ctagctttgc aaagaaggct gtagtgtttt acgaatcgta aagagaatga | 180 |
| ccacacatac agaggtagta cagattagtc acgctttgtc tgattatata tggattaaga | 240 |
| agtttttaga ggacatcatg ctgctgacag ttgtgaaacg ttcctaaaag ccttgtacca | 300 |
| aatttctcaa tatgatcaat agctgtagac aggcgaaggc attgatgagg gatggataag | 360 |
| tatcggtatc aagaatgcaa gacctatctt gattagtctg acgatttgat tctcgtagct | 420 |
| tcatactttt ggagcatttg cctggtgcaa actgagctcc ggtatagttt tgttgcctac | 480 |
| caaacgtgta aagattcttc tgtaagtttt ggttaaaagc aaagaactca tgcctcgtgt | 540 |
| tgcctgctcc cattctattt ctcaaaagtg attaagggga ctacaagata ggaattttt | 600 |
| ttctagtttg aaaacttgaa ttgttatgca atgcttgtac atattcgttt cgaggtagtt | 660 |
| tcttctcttt atgttgaaat cttttaatat tccgattacc gaactgagag atcactttc | 720 |
| ttgagagttt taaatgagga tagggtagtt ggattttcg ttcaccgctc cacttgatac | 780 |
| ttgatattct ggaaagctcc agatgtgtcc atcctgcggt cgtcgatttt cattttgttg | 840 |
| actttgctac attctccgtt tggaaaagct gatatttgct ggaatgtgta gttgatgcag | 900 |
| gtgtatggtc tcagatgatt acttgactga aatgagttca aacatagatg tcaacccttt | 960 |
| tttaaaaaag taacccaact ctgtgtctat catcacgtag tagtaagatg ctctgatgac | 1020 |
| ctcgtccaag ctttctttc aagaatacaa ttagatttaa cacgtatcga aatgtagtgg | 1080 |
| aatgaaggaa actacttgcg cgcccccgaa tactcaccgt atactgagct tgggtcatgg | 1140 |
| gtagattaac tctttgagca tatcatggta ttcgctggat tgagatctgt gtttagcaag | 1200 |
| cataattctg ttcaatccta ctaccctgat aatggtaaca cgctcaaaga ataatgatcc | 1260 |
| tttcatctaa agtttaacct cgctgtaatg cttacaagcc gctgagaatc gcttagacga | 1320 |
| ttaattgtgg gagcccttgt tatcaaccaa gttctaatgt gaattgattg attcctggcc | 1380 |

```
tttgccctgt tttatgatga actagctccc caaaaaaaca ttaatcttac aggaacaact    1440
accaatatgc tagccttcaa tatctattgt ttgatggccc cttatttttcc tgtcatctac    1500 ttacgaaccg ataagtgtcc tttttgaaca gttattttta cagtatagta ttatagttag    1560
tggcaagcat cccacagttc atttttgcct agaatgtgct aagtcactca ccggtctaat    1620
cttattattt gtaactgacc agttttcttg gaaagtactt ttatgtcagg tatgaacaaa    1680
tattgactac aagcattgca ttctattaca tcagcataat agtccttgct ctgatcacca    1740
acgtttggat ttttgtacaa cagcagctac tttcttaacc gtccagatct agccacttgg    1800
taagcaacta ttttcagcgg ttttaatcaa acagaactct accatctcat atttaataca    1860
tttataaacg ttatgcgttt tcccagctct gtattcaagt agccagtttc attttgatct    1920
taatttactt actatgtatg ttgagcttta gtactccttc tggttttttag caagagtgac    1980 cgagtctacc cttttttctat taatatgttt tgacctgatt gtatacgtat tggtttaagt    2040
cactgaaatt tattaatgac tttagtcgtc tcactaatga gagtcatcgt aggctgacaa    2100
actcttcttt gaatataaaa tattttccta gtgaatgctg aagatgttct taagtaatcc    2160
actaatgatc atgtaatctt aaatgcatcc tattgtgttc actgttgagt atgtttcatt    2220
tactcaaaca tgctcctcat tctaagtttc cgatggttgc cgaagatagc gtggtccttt    2280
agttgttcta tgtgagatca aatgccgcag gtttgaaata ccaaaaattt atgtaaccac    2340
ttatccgtgc tattgaaagt tttaacaaaa cttcgttttg tatttggact aattggcact    2400
tgcttcttct ttgtgaacgt cattgaatag agcctctatg aaagaagaat ggaacaccat    2460
tatgcctgtc aaccagaatg attgggttcg cttatgagga tttaatagtt tgacgtttta    2520
ggttatatct atcaagtgac acttcgcgaa atgcgctttt                          2559
```

<210> SEQ ID NO 24
<211> LENGTH: 43
<212> TYPE: DNA
<213> ORGANISM: Artificial
<220> FEATURE:
<223> OTHER INFORMATION: Primer

<400> SEQUENCE: 24

```
ttagcggccg catgaaacat aggaatacta ccatggcacg acc                       43
```

<210> SEQ ID NO 25
<211> LENGTH: 47
<212> TYPE: DNA
<213> ORGANISM: Artificial
<220> FEATURE:
<223> OTHER INFORMATION: Primer

<400> SEQUENCE: 25

```
ttagcggccg cgtgaaacat aggaatacta ctatgccatc atgggtg                   47
```

<210> SEQ ID NO 26
<211> LENGTH: 39
<212> TYPE: DNA
<213> ORGANISM: Artificial
<220> FEATURE:
<223> OTHER INFORMATION: Primer

<400> SEQUENCE: 26

```
ttagcggccg caaaattagt atcagttggc catgcgacc                            39
```

<210> SEQ ID NO 27

```
<211> LENGTH: 41
<212> TYPE: DNA
<213> ORGANISM: Artificial
<220> FEATURE:
<223> OTHER INFORMATION: Primer

<400> SEQUENCE: 27
ttagcggccg cgaaatcagt atcagttggc tatgtgaaca g                 41

<210> SEQ ID NO 28
<211> LENGTH: 55
<212> TYPE: DNA
<213> ORGANISM: Artificial
<220> FEATURE:
<223> OTHER INFORMATION: Primer

<400> SEQUENCE: 28
ttagcggccg cgaagaaaag atcaaactta gtctaggtga ggctaatcaa taaag   55

<210> SEQ ID NO 29
<211> LENGTH: 52
<212> TYPE: DNA
<213> ORGANISM: Artificial
<220> FEATURE:
<223> OTHER INFORMATION: Primer

<400> SEQUENCE: 29
ttagcggccg ccatcaaata ttgctaggta ggcactttttt tcggtaagcg tg     52

<210> SEQ ID NO 30
<211> LENGTH: 41
<212> TYPE: DNA
<213> ORGANISM: Artificial
<220> FEATURE:
<223> OTHER INFORMATION: Primer

<400> SEQUENCE: 30
ttagcggccg ccaagcattt catcataaga atcaggacct c                 41

<210> SEQ ID NO 31
<211> LENGTH: 50
<212> TYPE: DNA
<213> ORGANISM: Artificial
<220> FEATURE:
<223> OTHER INFORMATION: Primer

<400> SEQUENCE: 31
ttagcggccg ctaagcttcc tatcaaaatg atcatagctt atgtggcaac        50

<210> SEQ ID NO 32
<211> LENGTH: 1207
<212> TYPE: DNA
<213> ORGANISM: Artificial
<220> FEATURE:
<223> OTHER INFORMATION: GFP gene

<400> SEQUENCE: 32 tttttttgtag aaatgtcttg gtgtcctcgt ccaatcaggt agccatctct gaaatatctg   60
gctccgttgc aactccgaac gacctgctgg caacgtaaaa ttctccgggg taaaacttaa  120
atgtggagta atggaaccag aaacgtctct tcccttctct ctccttccac cgcccgttac  180
cgtccctagg aaattttact ctgctggaga gcttcttcta cggccccctt gcagcaatgc  240
tcttcccagc attacgttgc gggtaaaacg gaggtcgtgt acccgaccta gcagcccagg  300
gatggaaaag tcccggccgt cgctggcaat aatagcgggc ggacgcatgt catgagatta  360
```

```
ttggaaacca ccagaatcga atataaaagg cgaacacctt tcccaatttt ggtttctcct      420
gacccaaaga ctttaaattt aatttatttg tccctatttc aatcaattga acaactatca      480
aaacacaatg gtgagcaagg gcgaggagct gttcaccggg gtggtgccca tcctggtcga      540
gctggacggc gacgtaaacg gccacaagtt cagcgtgtcc ggcgagggcg agggcgatgc      600
cacctacggc aagctgaccc tgaagttcat ctgcaccacc ggcaagctgc ccgtgccctg      660
gcccaccctc gtgaccaccc tgacctacgg cgtgcagtgc ttcagccgct accccgacca      720
catgaagcag cacgacttct tcaagtccgc catgcccgaa ggctacgtcc aggagcgcac      780
catcttcttc aaggacgacg gcaactacaa gacccgcgcc gaggtgaagt tcgagggcga      840
caccctggtg aaccgcatcg agctgaaggg catcgacttc aaggaggacg gcaacatcct      900
ggggcacaag ctggagtaca actacaacag ccacaacgtc tatatcatgg ccgacaagca      960
gaagaacggc atcaaggtga acttcaagat ccgccacaac atcgaggacg gcagcgtgca     1020
gctcgccgac cactaccagc agaacacccc catcggcgac ggccccgtgc tgctgcccga     1080
caaccactac ctgagcaccc agtccgccct gagcaaagac cccaacgaga gcgcgatca      1140 catggtcctg ctggagttcg tgaccgccgc cgggatcact ctcggcatgg acgagctgta     1200
caagtaa                                                                1207
```

```
<210> SEQ ID NO 33
<211> LENGTH: 46
<212> TYPE: DNA
<213> ORGANISM: Artificial
<220> FEATURE:
<223> OTHER INFORMATION: Primer

<400> SEQUENCE: 33
ttaaagcttg cggccgcttt tttgtagaaa tgtcttggtg tcctcg                     46

<210> SEQ ID NO 34
<211> LENGTH: 36
<212> TYPE: DNA
<213> ORGANISM: Artificial
<220> FEATURE:
<223> OTHER INFORMATION: Primer

<400> SEQUENCE: 34
ttagaattct tacttgtaca gctcgtccat gccgag                                36

<210> SEQ ID NO 35
<211> LENGTH: 42
<212> TYPE: DNA
<213> ORGANISM: Artificial
<220> FEATURE:
<223> OTHER INFORMATION: Primer

<400> SEQUENCE: 35
ttagcggccg cttctgggtt cgttattagc aatccgttat ag                         42

<210> SEQ ID NO 36
<211> LENGTH: 42
<212> TYPE: DNA
<213> ORGANISM: Artificial
<220> FEATURE:
<223> OTHER INFORMATION: Primer

<400> SEQUENCE: 36
ttagcggccg cactttttct tcattttaga gcattagaga tg                         42
```

<210> SEQ ID NO 37
<211> LENGTH: 41
<212> TYPE: DNA
<213> ORGANISM: Artificial
<220> FEATURE:
<223> OTHER INFORMATION: Primer

<400> SEQUENCE: 37
ttagcggccg catcgtccaa tggacaaata acgatattg c                            41

<210> SEQ ID NO 38
<211> LENGTH: 41
<212> TYPE: DNA
<213> ORGANISM: Artificial
<220> FEATURE:
<223> OTHER INFORMATION: Primer

<400> SEQUENCE: 38
ttagcggccg cgattgcttt cataaattgg ctgtgatttt c                           41

<210> SEQ ID NO 39
<211> LENGTH: 42
<212> TYPE: DNA
<213> ORGANISM: Artificial
<220> FEATURE:
<223> OTHER INFORMATION: Primer

<400> SEQUENCE: 39
ttaaagcttc caatcaaaca aggtgacttg cgcgaagcaa tg                          42

<210> SEQ ID NO 40
<211> LENGTH: 37
<212> TYPE: DNA
<213> ORGANISM: Artificial
<220> FEATURE:
<223> OTHER INFORMATION: Primer

<400> SEQUENCE: 40
ttaaagcttg aatatttcct ttacacttta caatttc                                37

<210> SEQ ID NO 41
<211> LENGTH: 111
<212> TYPE: DNA
<213> ORGANISM: Komagataella pastoris

<400> SEQUENCE: 41
ccaatcaaac aaggtgactt gcgcgaagca atgatttgtg gatgggctgc ggtatggcag       60
cataacaatg caacgctatt tcagaaattg taaagtgtaa aggaaatatt c               111

<210> SEQ ID NO 42
<211> LENGTH: 218
<212> TYPE: DNA
<213> ORGANISM: Komagataella pastoris

<400> SEQUENCE: 42
ggacctaaag atcgaccaat acttgcttac acggcagcgc gaaataaaag acattgataa       60
tgtagagtaa gtactatttc ttcaaaagat agaaccactc tcagaggcta actagaagat      120
ctaaaacgga tgtacagcta atatgtttcg aggcaatcat gttcaggtgc gcctcaagtg      180
gctcttaatc tattttaaag cataatccac gaaaattt                              218

<210> SEQ ID NO 43
<211> LENGTH: 40

<212> TYPE: DNA
<213> ORGANISM: Artificial
<220> FEATURE:
<223> OTHER INFORMATION: Primer

<400> SEQUENCE: 43
ttagcggccg cccaatcaaa caaggtgact tgcgcgaagc          40

<210> SEQ ID NO 44
<211> LENGTH: 37
<212> TYPE: DNA
<213> ORGANISM: Artificial
<220> FEATURE:
<223> OTHER INFORMATION: Primer

<400> SEQUENCE: 44
ttatctagag cagttatctt catatatttt cagtatg          37

<210> SEQ ID NO 45
<211> LENGTH: 33
<212> TYPE: DNA
<213> ORGANISM: Artificial
<220> FEATURE:
<223> OTHER INFORMATION: Primer

<400> SEQUENCE: 45
ttatctagac acctagtgac ttgtcatatt tgc          33

<210> SEQ ID NO 46
<211> LENGTH: 33
<212> TYPE: DNA
<213> ORGANISM: Artificial
<220> FEATURE:
<223> OTHER INFORMATION: Primer

<400> SEQUENCE: 46
ttatctagac tctctggcat cattcatgta agc          33

<210> SEQ ID NO 47
<211> LENGTH: 33
<212> TYPE: DNA
<213> ORGANISM: Artificial
<220> FEATURE:
<223> OTHER INFORMATION: Primer

<400> SEQUENCE: 47
ttatctagag tttttaacac tctcttctca tcc          33

<210> SEQ ID NO 48
<211> LENGTH: 30
<212> TYPE: DNA
<213> ORGANISM: Artificial
<220> FEATURE:
<223> OTHER INFORMATION: Primer

<400> SEQUENCE: 48
ttatctagac attggagatg gagattggag          30

<210> SEQ ID NO 49
<211> LENGTH: 32
<212> TYPE: DNA
<213> ORGANISM: Artificial
<220> FEATURE:
<223> OTHER INFORMATION: Primer

<400> SEQUENCE: 49
ttatctagaa attgctatca gaaggaattt gg                           32

<210> SEQ ID NO 50
<211> LENGTH: 31
<212> TYPE: DNA
<213> ORGANISM: Artificial
<220> FEATURE:
<223> OTHER INFORMATION: Primer

<400> SEQUENCE: 50
ttatctagag ggctgagagg atatgcaaat g                            31

<210> SEQ ID NO 51
<211> LENGTH: 35
<212> TYPE: DNA
<213> ORGANISM: Artificial
<220> FEATURE:
<223> OTHER INFORMATION: Primer

<400> SEQUENCE: 51
ttatctagac tttaataccc taatatacgc aatcg                        35

<210> SEQ ID NO 52
<211> LENGTH: 43
<212> TYPE: DNA
<213> ORGANISM: Artificial
<220> FEATURE:
<223> OTHER INFORMATION: Primer

<400> SEQUENCE: 52
ttagcggccg caactcaatg tttttgtttc tctcgacgaa acg               43

<210> SEQ ID NO 53
<211> LENGTH: 33
<212> TYPE: DNA
<213> ORGANISM: Artificial
<220> FEATURE:
<223> OTHER INFORMATION: Primer

<400> SEQUENCE: 53
ttaactagtt cgaactttt tgttttcct tgg                           33

<210> SEQ ID NO 54
<211> LENGTH: 35
<212> TYPE: DNA
<213> ORGANISM: Artificial
<220> FEATURE:
<223> OTHER INFORMATION: Primer

<400> SEQUENCE: 54
ttaactagtc ttgaaaatac caaaagctca aaagc                        35

<210> SEQ ID NO 55
<211> LENGTH: 33
<212> TYPE: DNA
<213> ORGANISM: Artificial
<220> FEATURE:
<223> OTHER INFORMATION: Primer

<400> SEQUENCE: 55
ttaactagtc tgtagtttca gttgttgttg acg                          33

<210> SEQ ID NO 56
<211> LENGTH: 30
<212> TYPE: DNA
<213> ORGANISM: Artificial

```
<220> FEATURE:
<223> OTHER INFORMATION: Primer

<400> SEQUENCE: 56
ttaactagtg acccettgct ctaaatgctc                                    30

<210> SEQ ID NO 57
<211> LENGTH: 31
<212> TYPE: DNA
<213> ORGANISM: Artificial
<220> FEATURE:
<223> OTHER INFORMATION: Primer

<400> SEQUENCE: 57
ttaactagtt taacattccc cctgctcaga c                                  31

<210> SEQ ID NO 58
<211> LENGTH: 36
<212> TYPE: DNA
<213> ORGANISM: Artificial
<220> FEATURE:
<223> OTHER INFORMATION: Primer

<400> SEQUENCE: 58
ttaactagtc actgaaacct tgttcttatt atctag                             36

<210> SEQ ID NO 59
<211> LENGTH: 38
<212> TYPE: DNA
<213> ORGANISM: Artificial
<220> FEATURE:
<223> OTHER INFORMATION: Primer

<400> SEQUENCE: 59
ttaactagta aattttcgtg gattatgctt taaaatag                           38

<210> SEQ ID NO 60
<211> LENGTH: 33
<212> TYPE: DNA
<213> ORGANISM: Artificial
<220> FEATURE:
<223> OTHER INFORMATION: Primer

<400> SEQUENCE: 60
ttaactagtg taaccaaaa aatctgtcag tac                                 33

<210> SEQ ID NO 61
<211> LENGTH: 39
<212> TYPE: DNA
<213> ORGANISM: Artificial
<220> FEATURE:
<223> OTHER INFORMATION: Primer

<400> SEQUENCE: 61
ttagcggccg cgaaattgta aagtgtaaag gaaatattc                          39

<210> SEQ ID NO 62
<211> LENGTH: 34
<212> TYPE: DNA
<213> ORGANISM: Artificial
<220> FEATURE:
<223> OTHER INFORMATION: Primer

<400> SEQUENCE: 62
ttagcggccg cgttgcacag atgatggaat attg                               34
```

<210> SEQ ID NO 63
<211> LENGTH: 37
<212> TYPE: DNA
<213> ORGANISM: Artificial
<220> FEATURE:
<223> OTHER INFORMATION: Primer

<400> SEQUENCE: 63
ttatctagag aatatttcct ttacacttta caatttc         37

<210> SEQ ID NO 64
<211> LENGTH: 32
<212> TYPE: DNA
<213> ORGANISM: Artificial
<220> FEATURE:
<223> OTHER INFORMATION: Primer

<400> SEQUENCE: 64
ttatctagac aatattccat catctgtgca ac              32

<210> SEQ ID NO 65
<211> LENGTH: 35
<212> TYPE: DNA
<213> ORGANISM: Artificial
<220> FEATURE:
<223> OTHER INFORMATION: Primer

<400> SEQUENCE: 65
ttatctagac tttaataccc taatatacgc aatcg           35

<210> SEQ ID NO 66
<211> LENGTH: 42
<212> TYPE: DNA
<213> ORGANISM: Artificial
<220> FEATURE:
<223> OTHER INFORMATION: Primer

<400> SEQUENCE: 66
ttagcggccg cacttttttct tcattttaga gcattagaga tg   42

<210> SEQ ID NO 67
<211> LENGTH: 39
<212> TYPE: DNA
<213> ORGANISM: Artificial
<220> FEATURE:
<223> OTHER INFORMATION: Primer

<400> SEQUENCE: 67
ttagcggccg cgaaattata gtactgacag atttttttgg      39

<210> SEQ ID NO 68
<211> LENGTH: 33
<212> TYPE: DNA
<213> ORGANISM: Artificial
<220> FEATURE:
<223> OTHER INFORMATION: Primer

<400> SEQUENCE: 68
ttagcggccg cggacctaaa gatcgaccaa tac             33

<210> SEQ ID NO 69
<211> LENGTH: 35
<212> TYPE: DNA
<213> ORGANISM: Artificial
<220> FEATURE:
<223> OTHER INFORMATION: Primer

```
<400> SEQUENCE: 69
ttagcggccg cctctcagag gctaactaga agatc                                    35

<210> SEQ ID NO 70
<211> LENGTH: 31
<212> TYPE: DNA
<213> ORGANISM: Artificial
<220> FEATURE:
<223> OTHER INFORMATION: Primer

<400> SEQUENCE: 70
ttaactagtg tattggtcga tctttaggtc c                                        31

<210> SEQ ID NO 71
<211> LENGTH: 33
<212> TYPE: DNA
<213> ORGANISM: Artificial
<220> FEATURE:
<223> OTHER INFORMATION: Primer

<400> SEQUENCE: 71
ttaactagtg atcttctagt tagcctctga gag                                      33

<210> SEQ ID NO 72
<211> LENGTH: 38
<212> TYPE: DNA
<213> ORGANISM: Artificial
<220> FEATURE:
<223> OTHER INFORMATION: Primer

<400> SEQUENCE: 72
ttaactagta aattttcgtg gattatgctt taaaatag                                 38

<210> SEQ ID NO 73
<211> LENGTH: 41
<212> TYPE: DNA
<213> ORGANISM: Artificial
<220> FEATURE:
<223> OTHER INFORMATION: Primer

<400> SEQUENCE: 73
ttagcggccg catcgtccaa tggacaaata aacgatattg c                             41

<210> SEQ ID NO 74
<211> LENGTH: 75
<212> TYPE: DNA
<213> ORGANISM: Artificial
<220> FEATURE:
<223> OTHER INFORMATION: Primer

<400> SEQUENCE: 74
ttaaagcttg cggccgcgga tccactagtc aattgagatc ttctagagga gacgtggaag         60
gacataccgc ttttg                                                          75

<210> SEQ ID NO 75
<211> LENGTH: 33
<212> TYPE: DNA
<213> ORGANISM: Artificial
<220> FEATURE:
<223> OTHER INFORMATION: Primer

<400> SEQUENCE: 75
ttagaattct ctagacagtc cggaagcgac ttg                                      33
```

```
<210> SEQ ID NO 76
<211> LENGTH: 28
<212> TYPE: DNA
<213> ORGANISM: Artificial
<220> FEATURE:
<223> OTHER INFORMATION: Primer

<400> SEQUENCE: 76
ttaggatcct acagagcttt atatcacc                                      28

<210> SEQ ID NO 77
<211> LENGTH: 36
<212> TYPE: DNA
<213> ORGANISM: Artificial
<220> FEATURE:
<223> OTHER INFORMATION: Primer

<400> SEQUENCE: 77
ttaggatcct gtttctatat tatctttgta ctaaag                              36

<210> SEQ ID NO 78
<211> LENGTH: 28
<212> TYPE: DNA
<213> ORGANISM: Artificial
<220> FEATURE:
<223> OTHER INFORMATION: Primer

<400> SEQUENCE: 78
ttagaattct acagagcttt atatcacc                                      28

<210> SEQ ID NO 79
<211> LENGTH: 36
<212> TYPE: DNA
<213> ORGANISM: Artificial
<220> FEATURE:
<223> OTHER INFORMATION: Primer

<400> SEQUENCE: 79
ttagaattct gtttctatat tatctttgta ctaaag                              36

<210> SEQ ID NO 80
<211> LENGTH: 33
<212> TYPE: DNA
<213> ORGANISM: Artificial
<220> FEATURE:
<223> OTHER INFORMATION: Primer

<400> SEQUENCE: 80
ttagaattcc ccacacacca tagcttcaaa atg                                 33

<210> SEQ ID NO 81
<211> LENGTH: 31
<212> TYPE: DNA
<213> ORGANISM: Artificial
<220> FEATURE:
<223> OTHER INFORMATION: Primer

<400> SEQUENCE: 81
ttagaattct cagtcctgct cctcggccac g                                   31

<210> SEQ ID NO 82
<211> LENGTH: 607
<212> TYPE: DNA
<213> ORGANISM: Ogataea polymorpha

<400> SEQUENCE: 82
```

```
ggagacgtgg aaggacatac cgcttttgag aagcgtgttt gaaaatagtt cttttctctgg    60 tttatatcgt ttatgaagtg atgagatgaa aagctgaaat agcgagtata ggaaaattta   120
atgaaaatta aattaaatat tttcttaggc tattagtcac cttcaaaatg ccggccgctt   180
ctaagaacgt tgtcatgatc gacaactacg actcgtttac ctggaacctg tacgagtacc   240
tgtgtcagga gggagccaat gtcgaggttt tcaggaacga tcagatcacc attccggaga   300
ttgagcagct caagccggac gttgtggtga tatccctgg tcctggccat ccaagaacag   360
actcgggaat atctcgcgac gtgatcagcc attttaaagg caagattcct gtctttggtg   420
tctgtatggg ccagcagtgt atcttcgagg agtttggcgg agacgtcgag tatgcgggcg   480
agattgtcca tggaaaaacg tccactgtta agcacgacaa caagggaatg ttcaaaaacg   540
ttccgcaaga tgttgctgtc accagatacc actcgctggc cggaacgctc aagtcgcttc   600
cggactg                                                              607

<210> SEQ ID NO 83
<211> LENGTH: 284
<212> TYPE: DNA
<213> ORGANISM: Ogataea polymorpha

<400> SEQUENCE: 83
tacagagctt tatatcacct tactgaacgc tagagtagac ccaattcccg gctcacacca    60
cccttacatg cagagctaac caataaggta attaattaac actatatagc tcgtggtgaa   120
cactggcccg gagtagtcat acgtgtaggt ttttggcgtg atgaaaatca ggtggcgcac   180
gacttttcgt aaagttcggg agggagtgct gcaaacggca tataaggacc agttttttctc   240 gcacattatc aattgctctt tagtacaaag ataatataga aaca                    284

<210> SEQ ID NO 84
<211> LENGTH: 2104
<212> TYPE: DNA
<213> ORGANISM: Artificial
<220> FEATURE:
<223> OTHER INFORMATION: Synthetic Construct

<400> SEQUENCE: 84
aagcttgcgg ccgcggatcc tacagagctt tatatcacct tactgaacgc tagagtagac    60
ccaattcccg gctcacacca cccttacatg cagagctaac caataaggta attaattaac   120
actatatagc tcgtggtgaa cactggcccg gagtagtcat acgtgtaggt ttttggcgtg   180
atgaaaatca ggtggcgcac gacttttcgt aaagttcggg agggagtgct gcaaacggca   240
tataaggacc agttttttctc gcacattatc aattgctctt tagtacaaag ataatataga   300
aacaggatcc actagtcaat tctacagagc tttatatcac cttactgaac gctagagtag   360
acccaattcc cggctcacac cacccttaca tgcagagcta accaataagg taattaatta   420
acactatata gctcgtggtg aacactggcc cggagtagtc atacgtgtag gttttttggcg   480 tgatgaaaat caggtggcgc acgacttttc gtaaagttcg ggagggagtg ctgcaaacgg   540
catataagga ccagttttttc tcgcacatta tcaattgctc tttagtacaa agataatata   600
gaaacagaat tgagatcttc tagaggagac gtggaaggac ataccgcttt tgagaagcgt   660
gtttgaaaat agttcttttt ctggtttata tcgtttatga agtgatgaga tgaaaagctg   720
aaatagcgag tataggaaaa tttaatgaaa attaaattaa atatttttctt aggctattag   780 tcaccttcaa aatgccggcc gcttctaaga acgttgtcat gatcgacaac tacgactcgt   840
```

```
ttacctggaa cctgtacgag tacctgtgtc aggagggagc caatgtcgag gttttcagga      900
acgatcagat caccattccg gagattgagc agctcaagcc ggacgttgtg gtgatatccc      960
ctggtcctgg ccatccaaga acagactcgg gaatatctcg cgacgtgatc agccatttta     1020
aaggcaagat tcctgtcttt ggtgtctgta tgggccagca gtgtatcttc gaggagtttg     1080
gcggagacgt cgagtatgcg ggcgagattg tccatggaaa acgtccact  gttaagcacg     1140 acaacaaggg aatgttcaaa acgttccgc  aagatgttgc tgtcaccaga taccactcgc     1200
tggccggaac gctcaagtcg cttccggact gtctagagaa ttctcagtcc tgctcctcgg     1260
ccacgaagtg cacgcagttg ccggccgggt cgcgcagggc gaactcccgc ccccacggct     1320
gctcgccgat ctcggtcatg gccggcccgg aggcgtcccg gaagttcgtg gacacgacct     1380
ccgaccactc ggcgtacagc tcgtccaggc cgcgcaccca cacccaggcc agggtgttgt     1440
ccggcaccac ctggtcctgg accgcgctga tgaacagggt cacgtcgtcc cggaccacac     1500
cggcgaagtc gtcctccacg aagtcccggg agaacccgag ccggtcggtc cagaactcga     1560
ccgctccggc gacgtcgcgc gcggtgagca ccggaacggc actggtcaac ttggccatgg     1620
tttagttcct caccttgtcg tattatacta tgccgatata ctatgccgat gattaattgt     1680
caacaccgcc ccttagatta gattgctatg ctttctttct aatgaacaag aagtaaaaaa     1740
agttgtaata gaacaagaaa aatgaaactg aaacttgaga aattgaagac cgtttattaa     1800
cttaaatatc aatggaggtc actgaaagag aaaaaaacta aaaaaaaaaa tttcaagaaa     1860
aagaaacgtg ataaaaattt ttattgcctt tttcgacgaa gaaaaagaaa cgaggcggtc     1920 tctttttct  tttccaaacc tttagtacgg gtaattaacg acaccctaga ggaagaaaga     1980
gggaaaattt agtatgctgt gcttgggtgt tttgaagtgg tacggcgatg cgcggagtcc     2040
gagaaaatct ggaagagtaa aaaaggagta gaaacatttt gaagctatgg tgtgtgggga     2100
attc                                                                  2104

<210> SEQ ID NO 85
<211> LENGTH: 111
<212> TYPE: DNA
<213> ORGANISM: Komagataella pastoris

<400> SEQUENCE: 85
gaatatttcc tttacacttt acaatttctg aaatagcgtt gcattgttat gctgccatac       60
cgcagcccat ccacaaatca ttgcttcgcg caagtcacct tgtttgattg g               111

<210> SEQ ID NO 86
<211> LENGTH: 218
<212> TYPE: DNA
<213> ORGANISM: Komagataella pastoris

<400> SEQUENCE: 86
aaattttcgt ggattatgct ttaaaataga ttaagagcca cttgaggcgc acctgaacat       60
gattgcctcg aaacatatta gctgtacatc cgttttagat cttctagtta gcctctgaga      120
gtggttctat cttttgaaga aatagtactt actctacatt atcaatgtct tttatttcgc      180
gctgccgtgt aagcaagtat tggtcgatct ttaggtcc                              218
```